(12) United States Patent
Blankman et al.

(10) Patent No.: US 11,034,674 B2
(45) Date of Patent: Jun. 15, 2021

(54) METHODS OF TREATING INFLAMMATION OR NEUROPATHIC PAIN

(71) Applicant: H. Lundbeck A/S, Valby (DK)

(72) Inventors: Jacqueline Lorayne Blankman, San Diego, CA (US); Jason Robert Clapper, San Diego, CA (US); R. Alan B. Ezekowitz, Princeton, NJ (US); Iain Peter Fraser, Scotch Plains, NJ (US); Cheryl A. Grice, Encinitas, CA (US); Todd K. Jones, Solana Beach, CA (US); Gary Paul O'Neill, San Diego, CA (US); Archie Wayne Thurston, Jr., O'Fallon, MO (US); Channing Rodney Beals, San Diego, CA (US)

(73) Assignee: H. LUNDBECK A/S, Valby (DK)

( * ) Notice: Subject to any disclaimer, the term of this patent is extended or adjusted under 35 U.S.C. 154(b) by 0 days.

(21) Appl. No.: 16/563,733

(22) Filed: Sep. 6, 2019

(65) Prior Publication Data
US 2020/0055841 A1 Feb. 20, 2020

Related U.S. Application Data

(63) Continuation of application No. 15/573,272, filed as application No. PCT/US2016/031668 on May 10, 2016, now Pat. No. 10,450,302.

(60) Provisional application No. 62/297,670, filed on Feb. 19, 2016, provisional application No. 62/159,770, filed on May 11, 2015.

(51) Int. Cl.
*A61K 31/497* (2006.01)
*C07D 403/10* (2006.01)
*A61K 31/495* (2006.01)
*C07D 295/205* (2006.01)
*A61P 29/00* (2006.01)

(52) U.S. Cl.
CPC .......... *C07D 403/10* (2013.01); *A61K 31/495* (2013.01); *A61P 29/00* (2018.01); *C07D 295/205* (2013.01)

(58) Field of Classification Search
CPC ..................................................... A61K 31/496
USPC ..................................................... 514/254.01
See application file for complete search history.

(56) References Cited

U.S. PATENT DOCUMENTS 4,327,725 A 5/1982 Cortese et al.
4,624,848 A 11/1986 Lee
(Continued)

FOREIGN PATENT DOCUMENTS

DE 1802739 A1 6/1969
JP S6183073 A 4/1986
(Continued)

OTHER PUBLICATIONS

Pellkofer et al. "The major brain endocannabinoid 2-AG controls neuropathic pain and mechanical hyperalgesia in patiens with neuromyelitis optica," PLOS One, 2013, vol. 8, Issue 8, e71500 . . . (Year: 2013).*

(Continued)

*Primary Examiner* — Shengjun Wang
(74) *Attorney, Agent, or Firm* — Wilson Sonsini Goodrich & Rosati

(57) ABSTRACT

Provided herein are methods of treating inflammation or neuropathic pain using an effective dose of a monoacylglycerol lipase inhibitor or a composition thereof.

11 Claims, 8 Drawing Sheets

(56) References Cited

U.S. PATENT DOCUMENTS

| | | | |
|---|---|---|---|
| 4,968,509 A | 11/1990 | Radebaugh et al. |
| 5,323,907 A | 6/1994 | Kalvelage |
| 5,456,923 A | 10/1995 | Nakamichi et al. |
| 5,461,140 A | 10/1995 | Heller et al. |
| 5,516,527 A | 5/1996 | Curatolo |
| 5,622,721 A | 4/1997 | Dansereau et al. |
| 5,686,105 A | 11/1997 | Kelm et al. |
| 5,700,410 A | 12/1997 | Nakamichi et al. |
| 5,977,175 A | 11/1999 | Lin |
| 6,465,014 B1 | 10/2002 | Moroni et al. |
| 6,932,983 B1 | 8/2005 | Straub et al. |
| 9,133,148 B2 | 9/2015 | Cisar et al. |
| 9,487,495 B2 | 11/2016 | Cisar et al. |
| 9,957,242 B2 | 5/2018 | Cisar et al. |
| 10,450,302 B2 | 10/2019 | Blankman et al. |
| 2008/0214524 A1 | 9/2008 | Lee et al. |
| 2010/0015225 A1 | 1/2010 | Diederich et al. |
| 2011/0275650 A1 | 11/2011 | Cravatt et al. |
| 2014/0163068 A1 | 6/2014 | Verwijs et al. |
| 2014/0357693 A1 | 12/2014 | Shaul et al. |
| 2015/0018335 A1 | 1/2015 | Cisar et al. |
| 2015/0313843 A1 | 11/2015 | Shaw et al. |
| 2018/0208568 A1 | 7/2018 | Cisar et al. |

FOREIGN PATENT DOCUMENTS

| | | |
|---|---|---|
| JP | 2000500448 A | 1/2000 |
| JP | 2008500270 A | 1/2008 |
| JP | 2008521768 A | 6/2008 |
| JP | 2009523729 A | 6/2009 |
| JP | 2010513447 A | 4/2010 |
| RU | 2167150 C2 | 5/2001 |
| WO | WO-8911794 A1 | 12/1989 |
| WO | WO-9311097 A1 | 6/1993 |
| WO | WO-9517439 A2 | 6/1995 |
| WO | WO-9800408 A1 | 1/1998 |
| WO | WO-0125188 A1 | 4/2001 |
| WO | WO-0234382 A1 | 5/2002 |
| WO | WO-2005063698 A1 | 7/2005 |
| WO | WO-2005070910 A2 | 8/2005 |
| WO | WO-2005080363 A1 | 9/2005 |
| WO | WO-2008106047 A2 | 9/2008 |
| WO | WO-2009141238 A1 | 11/2009 |
| WO | WO-2010009207 A1 | 1/2010 |
| WO | WO-2010063802 A1 | 6/2010 |
| WO | WO-2010111050 A1 | 9/2010 |
| WO | WO-2010129497 A1 | 11/2010 |
| WO | WO-2011054795 A1 | 5/2011 |
| WO | WO-2011151808 A1 | 12/2011 |
| WO | WO-2013102431 A1 | 7/2013 |
| WO | WO-2013103973 A1 | 7/2013 |
| WO | WO-2013142307 A1 | 9/2013 |
| WO | WO-2013159095 A1 | 10/2013 |
| WO | WO-2015179559 A2 | 11/2015 |
| WO | WO-2016183097 A1 | 11/2016 |
| WO | WO-2018093946 A1 | 5/2018 |
| WO | WO-2018093947 A1 | 5/2018 |
| WO | WO-2018093950 A1 | 5/2018 |
| WO | WO-2018093953 A1 | 5/2018 |

OTHER PUBLICATIONS

Alhouayek et al. Increasing endogenous 2-arachidonoylglycerol levels counteracts colitis and related systemic inflammation. FASEB 25(8):2711-2721 (2011).

Ameloot et al. Endocannabinoid control of gastric sensorimotor function in man. Aliment Pharmacol Ther 31(10):1123-1131 (2010).

Anderson et al. Actions of the dual FAAH/MAGL inhibitor JZL195 in a murine inflammatory pain model. Neuropharmacology 81:224-230 (2013).

Berge et al. Pharmaceutical Salts. Journal of Pharmaceutical Sciences 66(1):1-19 (Jan. 1977).

Blake et al. Preliminary assessment of the efficacy, tolerability and safety of a cannabis-based medicine (Sativex) in the treatment of pain caused by rheumatoid arthritis. Rheumatology (Oxford) 45(1):50-52 (2006).

Blankman et al. A comprehensive profile of brain enzymes that hydrolyze the endocannabinoid 2-arachidonoylglycerol. Chem. Biol. 14:1347-1356 (2007).

Burckhardt et al. The fibromyalgia impact questionnaire: development and validation. J Rheumatol 18(5):728-733 (1991).

Chang et al. Highly Selective Inhibitors of Monoacylglycerol Lipase Bearing a Reactive Group that is Bioisosteric with Endocannabinoid Substrates. ChemBiol 19(5):579-588 (2012).

Chang et al. Proteome-wide reactivity profiling identifies diverse carbamate chemotypes tuned for serine hydrolase inhibition. ACS Chem Biol 8:1590-1599 (2013).

Chen et al. Monoacylglycerol lipase is a therapeutic target for Alzheimer's disease. Cell Rep. 2(5):1329-1339 (2012).

Collin et al. A double-blind, randomized, placebo-controlled, parallel-group study of Sativex, in subjects with symptoms of spasticity due to multiple sclerosis. Neurol Res 32(5):451-459 (2010).

Collin et al. Randomized controlled trial of cannabis-based medicine in spasticity caused by multiple sclerosis. Eur J Neurol 14(3):290-296 (2007).

Fiz et al. Cannabis use in patients with fibromyalgia: effect on symptoms relief and health-related quality of life. PLoS One 6(4):e18440 (2011).

Fowler. Monoacylglycerol lipase—a target for drug development? Br Pharmacol. 166:1568-1585 (2012).

Guindon et al. Alterations in endocannabinoid tone following chemotherapy-induced peripheral neuropathy: effects of endocannabinoid deactivation inhibitors targeting fatty-acid amide hydrolase and monoacylglycerol lipase in comparison to reference analgesics following cisplatin treatment. Pharmacol Res 67(1):94-109 (2013).

Hanlon et al. Circadian rhythm of circulating levels of the endocannabinoid 2-arachidonoylglycerol. J Clin Endocrinol Metab 100:220-226 (2015).

Hill. Medical Marijuana for Treatment of Chronic Pain and Other Medical and Psychiatric Problems: A Clinical Review. JAMA 313(24):2474-2483 (2015).

Howard et al. Cannabis use in sickle cell disease: a questionnaire study. Br J Haematol 131(1):123-128 (2005).

Hruba et al. Simultaneous Inhibition of Fatty Acid Amide Hydrolase and Monoacylglycerol Lipase Shares Discriminative Stimulus Effects with delta9-Tetarhydrocannabinol in Mice. The Journal of Pharmacology and Experimental Therapeutics 353:261-268 (2015).

Jiang et al. (+)—Borneol alleviates mechanical hyperalgesia in models of chronic inflammatory and neuropathic pain in mice. EurJ Pharmacol 757:53-58 (2015).

Khasabova et al. Increasing 2-arachidonoyl glycerol signaling in the periphery attenuates mechanical hyperalgesia in a model of bone cancer pain. Pharmacol Res 64(1):60-67 (2011).

King et al. URB602 inhibits monoacylglycerol lipase and selectively blocks 2-arachidonoylglycerol degradation in intact brain slices. Chem Biol 14(12):1357-1365 (2007).

Kinsey et al. Blockade of Endocannabinoid-Degrading Enzymes Attenuates Neuropathic Pain. J Pharmacol Exp Ther 330(3):902-910 (2009).

Kohli et al. Pain-related behaviors and neurochemical alterations in mice expressing sickle hemoglobin: modulation by cannabinoids. Blood 116(3):456-465 (2010).

Korhonen et al. Piperazine and piperidine carboxamides and carbamates as inhibitors of fatty acid amide hydrolase (FAAH) and monoacylglycerol lipase (MAGL). Bioorg Med Chem 22(23):6694-6705 (2014).

Labar et al. A review on the monoacylglycerol lipase: at the interface between fat and endocannabinoid signalling. Curr Med Chem 17(24):2588-2607 (2010).

Langford et al. A double-blind, randomized, placebo-controlled, parallel-group study of THC/CBD oromucosal spray in combination with the existing treatment regimen, in the relief of central neuropathic pain in patients with multiple sclerosis. J Neurol 260(4):984-997 (2013).

(56) References Cited

OTHER PUBLICATIONS

Long et al. Characterization of tunable piperidine and piperazine carbamates as inhibitors of endocannabinoid hydrolases. J Med chem 53(4):1830-1842 (2010).
Long et al. Selective blockade of 2-arachidonoylglycerol hydrolysis produces cannabinoid behavioral effects. Nat Chem Biol. 5(1):37-44 (2009).
Ly et al. Increased cerebral cannabinoid-1 receptor availability is a stable feature of functional dyspepsia: a [F]MK-9470 PET study. Psychother Psychosom 84(3):149-158 (2015).
Malik et al. Dronabinol increases pain threshold in patients with functional chest pain: a pilot double-blind placebo-controlled trial. Dis Esophagus 30(2):1-8 (2017).
Meanwell et al. Synopsis of some recent tactical application of bioisosteres in drug design. J Med Chem 54(8):2529-2591 (2011).
Mease et al. A randomized, double-blind, placebo-controlled, phase III trial of pregabalin in the treatment of patients with fibromyalgia. J Rheumatol 35(3):502-514 (2008).
Mukhamadieva et al. Search for New Drugs Synthesis and Biological Activity of O-Carbamoylated 1,1,1,3,3,3-Hexafluoroisopropanols as New Specific Inhibitors of Carboxylesterase. Pharmaceutical Chemistry Journal 46(8):461-464 (2012).
Muller-Vahl et al. Treatment of Tourette Syndrome with Delta-9-Tetrahydrocannbinol (delta9-THC): No Influence on Neuropsychological Performance. Neuropsychopharmacology 28:384-388 (2003).
Müller-Vahl et al. Treatment of Tourette's syndrome with Delta 9-tetrahydrocannabinol (THC): a randomized crossover trial. Pharmacopsychiatry 35(2):57-61 (2002).
Nomura et al. Endocannabinoid hydrolysis generates brain prostaglandins that promote neuroinflammation. Science 334(6057):809-813 (2011).
Patani et al. Bioisosterism: A Rational Approach in Drug Design. Chem. Rev. 96:3147-3176 (1996).
PCT/US2013/020551 International Preliminary Report on Patentability dated Jul. 17, 2014.
PCT/US2013/020551 International Search Report dated May 21, 2013.
PCT/US2016/031668 International Preliminary Report on Patentability dated Nov. 23, 2017.
PCT/US2016/031668 International Search Report and Written Opinion dated Aug. 11, 2016.
Piro et al. A dysregulated endocannabinoid-eicosanoid network supports pathogenesis in a mouse model of Alzheimer's disease. Cell Rep. 1(6):617-623 (2012).
Porsteinsson et al. Effect of citalopram on agitation in Alzheimer disease: the CitAD randomized clinical trial. JAMA 311(7):682-691 (2014).
PubChem CID 17217128 http://pubchem.ncbi.nlm.nih.gov/summary/summary.cgi?cid=17217128 Retrieved Apr. 30, 2013 Create Date: Nov. 13, 2007 (3 pgs.).
PubChem CID 3469875. Compound Summary downloaded at https://pubchem.ncbi.nlm.nih.gov/compound/3469875 on Jun. 5, 2019,pp. 1-8 (2019).
PubChem CID 3469875. http://pubchem.ncbi.nlm.nih.gov/summary/summary.cgi?cid=3469875Retrieved Mar. 4, 2013 Create Date: Sep. 8, 2005 (11 pgs.).
PubChem CID 669902 http://pubchem.ncbi.nlm.nih.gov/summary/summary.cgi?cid=669902 Retrieved May 1, 2013 Create Date: Jul. 8, 2005 (4 pgs.).
Rautio et al. Prodrugs: design and clinical applications. Nat Rev Drug Discov 7(3):255-270 (2008).
Rhyne et al. Effects of Medical Marijuana on Migraine Headache Frequency in an Adult Population. Pharmacotherapy 36:505-510 (2016).
Richardson et al. Characterisation of the cannabinoid receptor system in synovial tissue and fluid in patients with osteoarthritis and rheumatoid arthritis. Arthritis Res Ther 10(2):R43 (2008).
Rog et al. Randomized, controlled trial of cannabis-based medicine in central pain in multiple sclerosis. Neurology 65(6):812-819 (2005).
Sarchielli et al. Endocannabinoids in chronic migraine: CSF findings suggest a system failure. Neuropsychopharmacology 32(6):1384-1390 (2007).
Science IP Report dated Dec. 11, 2014 (126 pgs.).
Skrabek et al. Nabilone for the treatment of pain in fibromyalgia. J Pain 9(2):164-173 (2008).
South. Synthesis and Reactions of Halogenated Thiazole Isocyanates. Journal of Heterocyclic Chemistry 28:1003-1011 (1991).
Studnev et al. Synthesis, Antibacterial and Immunotropic Activity of Poly(fluoroalkyl-N-arylcarbamates. Pharmaceutical Chemistry Journal 36(12):654-657 (2002).
Thornber. Isosterism and molecular modification in drug design. Chem Soc Rev 8:563-580 (1979).
Turcotte et al. Nabilone as an adjunctive to gabapentin for multiple sclerosis-induced neuropathic pain: a randomized controlled trial. Pain Med 16(1):149-159 (2015).
U.S. Appl. No. 14/369,982 Office Action dated Mar. 8, 2016.
U.S. Appl. No. 14/369,982 Office Action dated Oct. 22, 2015.
U.S. Appl. No. 14/599,105 Office Action dated Apr. 8, 2015.
U.S. Appl. No. 15/272,313 Office Action dated Apr. 10, 2017.
U.S. Appl. No. 15/272,313 Office Action dated Aug. 25, 2017.
U.S. Appl. No. 15/573,272 Office Action dated Dec. 14, 2018.
U.S. Appl. No. 15/925,517 Office Action dated Jun. 20, 2019.
Urry et al. Free-radical chain addition reactions of aldehydes with perfluoro ketones and chloro perfluoro ketones. J Org Chem 32(2):347-352 (1967).
Volicer et al. Effects of dronabinol on anorexia and disturbed behavior in patients with Alzheimer's disease. Int J Geriatr Psychiatry 12(9):913-919 (1997).
Walther et al. Randomized, controlled crossover trial of dronabinol, 2.5 mg, for agitation in 2 patients with dementia. J Clin Psychopharmacol 31(2):256-258 (2011).
Ware et al. The effects of nabilone on sleep in fibromyalgia: results of a randomized controlled trial. Anesth Analg 110(2):604-610 (2010).
Whiting et al. Cannabinoids for Medical Use: A Systematic Review and Meta-analysis. JAMA 313(24):2456-2473 (2015).
Zajicek et al. Cannabinoids for treatment of spasticity and other symptoms related to multiple sclerosis (CAMS study): multicentre randomised placebo-controlled trial. Lancet 362(9395):1517-1526 (2003).
Bernstein. Crystal Structure Prediction and Polymorphism. ACA Transactions 39:14-23 (2004).
Braga et al. Making crystals from crystals: a green route to crystal engineering and polymorphism. Chemical Communications (29):3635-45 (2005).
Jones et al. Pharmaceutical Cocrystals: An Emerging Approach to Physical Property Enhancement. MRS Bulletin 31:875-879 (2006).
Liberman et al. Pharmaceutical Dosage Forms. 2nd Ed. 1:209-214 (1990).
PCT/US2017/061871 International Search Report and Written Opinion dated Feb. 7, 2018.
PCT/US2017/061875 International Search Report and Written Opinion dated Feb. 7, 2018.
Price. The computational prediction of pharmaceutical crystal structures and polymorphism. Advanced Drug Delivery Reviews 56:301-319 (2004).
PubChem CID 71657619 Create date: Aug. 19, 2013 (12 pgs).

\* cited by examiner

METHODS OF TREATING INFLAMMATION OR NEUROPATHIC PAIN

CROSS-REFERENCE

This application is a continuation of U.S. application Ser. No. 15/573,272, filed Nov. 10, 2017, which is a U.S. National Stage Entry of International Application Number PCT/US2016/031668, filed May 10, 2016, which claims the benefit of priority from U.S. Provisional Application No. 62/297,670, filed Feb. 19, 2016, and also claims the benefit of priority from U.S. Provisional Application No. 62/159,770, filed May 11, 2015, all of which are incorporated herein by reference in their entirety.

BACKGROUND

Monoacylglycerol lipase (MGLL or MAGL) is an enzyme responsible for hydrolyzing endocannabinoids such as 2-AG (2-arachidonoylglycerol), an arachidonate based lipid, in the nervous system.

SUMMARY OF THE INVENTION

Disclosed herein are methods of treating inflammation or neuropathic pain in a patient in need thereof, comprising administering to the patient in need thereof an effective dose of 1,1,1,3,3,3-hexafluoropropan-2-yl 4-(2-(pyrrolidin-1-yl)-4-(trifluoromethyl)benzyl)piperazine-1-carboxylate (Compound 1), or a pharmaceutically acceptable salt thereof, wherein the effective dose is from about 1 mg to about 500 mg.

Further disclosed herein are methods of treating inflammation or neuropathic pain in a patient in need thereof, comprising administering to the patient in need thereof an effective dose of Compound 1, or a pharmaceutically acceptable salt thereof, wherein the concentration of plasma 2-AG of the patient increases at least 2-fold after administration of the effective dose.

Further disclosed herein are methods of treating inflammation or neuropathic pain in a patient in need thereof, comprising administering to the patient in need thereof an effective dose of Compound 1, or a pharmaceutically acceptable salt thereof, wherein a fragment of Compound 1 is covalently attached to at least 30% of MGLL in PBMCs from the patient after administration of the effective dose.

Further disclosed herein are methods of treating inflammation or neuropathic pain in a patient in need thereof, comprising administering to the patient in need thereof an effective dose of Compound 1, or a pharmaceutically acceptable salt thereof, wherein the plasma $AUC_{0-inf}$ of Compound 1 is at least 0.05 μM·hr after administration of the effective dose. Further disclosed herein are methods of treating inflammation or neuropathic pain in a patient in need thereof, comprising administering to the patient in need thereof an effective dose of Compound 1, or a pharmaceutically acceptable salt thereof, wherein the plasma $AUC_{0-inf}$ of Compound 1 is at least 0.1 μM·hr after administration of the effective dose. Further disclosed herein are methods of treating inflammation or neuropathic pain in a patient in need thereof, comprising administering to the patient in need thereof an effective dose of Compound 1, or a pharmaceutically acceptable salt thereof, wherein the plasma $AUC_{0-inf}$ of Compound 1 is at least 0.2 μM·hr after administration of the effective dose.

Further disclosed herein are methods of treating inflammation or neuropathic pain in a patient in need thereof, comprising administering to the patient in need thereof an effective dose of Compound 1, or a pharmaceutically acceptable salt thereof, wherein the steady state plasma $AUC_{0-inf}$ of Compound 1 is at least 0.05 μM·hr after administration of the effective dose. Further disclosed herein are methods of treating inflammation or neuropathic pain in a patient in need thereof, comprising administering to the patient in need thereof an effective dose of Compound 1, or a pharmaceutically acceptable salt thereof, wherein the steady state plasma $AUC_{0-inf}$ of Compound 1 is at least 0.1 μM·hr after administration of the effective dose. Further disclosed herein are methods of treating inflammation or neuropathic pain in a patient in need thereof, comprising administering to the patient in need thereof an effective dose of Compound 1, or a pharmaceutically acceptable salt thereof, wherein the steady state plasma $AUC_{0-inf}$ of Compound 1 is at least 0.2 μM·hr after administration of the effective dose.

Further disclosed herein are methods of treating inflammation or neuropathic pain in a patient in need thereof, comprising administering to the patient in need thereof an effective dose of Compound 1, or a pharmaceutically acceptable salt thereof, wherein after administration of the effective dose: (a) the concentration of plasma 2-AG of the patient increases at least 2-fold; and (b) a fragment of Compound 1 is covalently attached to at least 30% of MGLL in PBMCs from the patient.

Disclosed herein is also 1,1,1,3,3,3-hexafluoropropan-2-yl 4-(2-(pyrrolidin-1-yl)-4-(trifluoromethyl)benzyl)piperazine-1-carboxylate (Compound 1) or a pharmaceutically acceptable salt thereof, for use as a medicament. Further disclosed herein is Compound 1 or a pharmaceutically acceptable salt thereof, for use in a method of treating inflammation, pain, or neuropathic pain of the human or animal body; wherein the effective dose is from about 1 mg to about 500 mg; or wherein the concentration of plasma 2-AG of the patient increases at least 2-fold after administration of the effective dose; or wherein a fragment of Compound 1 is covalently attached to at least 30% of MGLL in PBMCs from the patient after administration of the effective dose; or wherein the plasma $AUC_{0-inf}$ of Compound 1 is at least 0.05 μM·hr after administration of the effective dose; or wherein the plasma $AUC_{0-inf}$ of Compound 1 is at least 0.1 μM·hr after administration of the effective dose; or wherein the plasma $AUC_{0-inf}$ of Compound 1 is at least 0.2 μM·hr after administration of the effective dose; or wherein the steady state plasma $AUC_{0-inf}$ of Compound 1 is at least 0.05 μM·hr after administration of the effective dose; or wherein the steady state plasma $AUC_{0-inf}$ of Compound 1 is at least 0.1 μM·hr after administration of the effective dose; or wherein the steady state plasma $AUC_{0-inf}$ of Compound 1 is at least 0.2 μM·hr after administration of the effective dose; or wherein after administration of the effective dose: (a) the concentration of plasma 2-AG of the patient increases at least 2-fold; and (b) a fragment of Compound 1 is covalently attached to at least 30% of MGLL in PBMCs from the patient.

Further disclosed herein are methods of treating Epilepsy/Seizure Disorder, Multiple Sclerosis, Neuromyelitis Optica (NMO), Tourette Syndrome, Alzheimer Disease, or abdominal pain associated with Irritable Bowel Syndrome in a patient in need thereof, comprising administering to the patient in need thereof an effective dose of 1,1,1,3,3,3-hexafluoropropan-2-yl 4-(2-(pyrrolidin-1-yl)-4-(trifluoromethyl)benzyl)piperazine-1-carboxylate (Compound 1), or a pharmaceutically acceptable salt thereof, wherein the effective dose is from about 1 mg to about 100 mg.

Further disclosed herein are methods of treating acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia in a patient in need thereof, comprising administering to the patient in need thereof an effective dose of 1,1,1,3,3,3-hexafluoropropan-2-yl 4-(2-(pyrrolidin-1-yl)-4-(trifluoromethyl)benzyl)piperazine-1-carboxylate (Compound 1), or a pharmaceutically acceptable salt thereof, wherein the effective dose is from about 1 mg to about 100 mg.

Further disclosed herein is also Compound 1 or a pharmaceutically acceptable salt thereof, for use in a method of treating Epilepsy/Seizure Disorder, Multiple Sclerosis, Neuromyelitis Optica (NMO), Tourette Syndrome, Alzheimer Disease, abdominal pain associated with Irritable Bowel Syndrome, acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia, wherein the effective dose is from about 1 mg to about 100 mg.

In some embodiments of the methods and medical uses described herein, the concentration of plasma 2-AG of the patient increases at least 3-fold after administration of the effective dose. In some embodiments of the methods and medical uses described herein, the concentration of plasma 2-AG of the patient increases at least 4-fold after administration of the effective dose. In some embodiments of the methods and medical uses described herein, the concentration of plasma 2-AG of the patient increases at least 5-fold after administration of the effective dose. In some embodiments of the methods and medical uses described herein, the concentration of plasma 2-AG of the patient increases at least 6-fold after administration of the effective dose. In some embodiments of the methods and medical uses described herein, the concentration of plasma 2-AG of the patient increases at least 7-fold after administration of the effective dose. In some embodiments of the methods and medical uses described herein, the concentration of plasma 2-AG of the patient increases at least 8-fold after administration of the effective dose. In some embodiments of the methods and medical uses described herein, the concentration of plasma 2-AG of the patient increases at least 9-fold after administration of the effective dose. In some embodiments of the methods and medical uses described herein, the concentration of plasma 2-AG of the patient increases at least 10-fold after administration of the effective dose. In some embodiments of the methods and medical uses described herein, the concentration of plasma 2-AG of the patient is measured in an in vitro assay.

In some embodiments of the methods and medical uses described herein, a fragment of Compound 1 is covalently attached to at least 40% of MGLL in PBMCs from the patient after administration of the effective dose. In some embodiments of the methods and medical uses described herein, a fragment of Compound 1 is covalently attached to at least 50% of MGLL in PBMCs from the patient after administration of the effective dose. In some embodiments of the methods and medical uses described herein, a fragment of Compound 1 is covalently attached to at least 60% of MGLL in PBMCs from the patient after administration of the effective dose. In some embodiments of the methods and medical uses described herein, a fragment of Compound 1 is covalently attached to at least 70% of MGLL in PBMCs from the patient after administration of the effective dose. In some embodiments of the methods and medical uses described herein, a fragment of Compound 1 is covalently attached to at least 80% of MGLL in PBMCs from the patient after administration of the effective dose. In some embodiments of the methods and medical uses described herein, a fragment of Compound 1 is covalently attached to at least 90% of MGLL in PBMCs from the patient after administration of the effective dose. In some embodiments of the methods and medical uses described herein, measurement of fragments of Compound 1 covalently attached to MGLL in PBMCs from the patient is performed using an in vitro assay.

In some embodiments of the methods and medical uses described herein, the plasma $AUC_{0-inf}$ of Compound 1 is at least 0.3 µM·hr after administration of the effective dose. In some embodiments of the methods and medical uses described herein, the plasma $AUC_{0-inf}$ of Compound 1 is at least 0.4 µM·hr after administration of the effective dose. In some embodiments of the methods and medical uses described herein, the plasma $AUC_{0-inf}$ of Compound 1 is at least 0.5 µM·hr after administration of the effective dose. In some embodiments of the methods and medical uses described herein, the plasma $AUC_{0-inf}$ of Compound 1 is at least 0.6 µM·hr after administration of the effective dose. In some embodiments of the methods and medical uses described herein, the plasma $AUC_{0-inf}$ of Compound 1 is at least 0.7 µM·hr after administration of the effective dose. In some embodiments of the methods and medical uses described herein, the plasma $AUC_{0-inf}$ of Compound 1 is at least 0.8 µM·hr after administration of the effective dose. In some embodiments of the methods and medical uses described herein, the plasma $AUC_{0-inf}$ of Compound 1 is at least 0.9 µM·hr after administration of the effective dose. In some embodiments of the methods and medical uses described herein, the plasma $AUC_{0-inf}$ of Compound 1 is at least 1.0 µM·hr after administration of the effective dose.

In some embodiments of the methods and medical uses described herein, the steady state plasma $AUC_{0-inf}$ of Compound 1 is at least 0.3 µM·hr after administration of the effective dose. In some embodiments of the methods and medical uses described herein, the steady state plasma $AUC_{0-inf}$ of Compound 1 is at least 0.4 µM·hr after administration of the effective dose. In some embodiments of the methods and medical uses described herein, the steady state plasma $AUC_{0-inf}$ of Compound 1 is at least 0.5 µM·hr after administration of the effective dose. In some embodiments of the methods and medical uses described herein, the steady state plasma $AUC_{0-inf}$ of Compound 1 is at least 0.6 µM·hr after administration of the effective dose. In some embodiments of the methods and medical uses described herein, the steady state plasma $AUC_{0-inf}$ of Compound 1 is at least 0.7 µM·hr after administration of the effective dose. In some embodiments of the methods and medical uses described herein, the steady state plasma $AUC_{0-inf}$ of Compound 1 is at least 0.8 µM·hr after administration of the effective dose. In some embodiments of the methods and medical uses described herein, the steady state plasma $AUC_{0-inf}$ of Compound 1 is at least 0.9 µM·hr after administration of the effective dose. In some embodiments of the methods and medical uses described herein, the steady state plasma $AUC_{0-inf}$ of Compound 1 is at least 1.0 µM·hr after administration of the effective dose.

In some embodiments of the methods and medical uses described herein, the effective dose is from about 1 mg to about 500 mg. In some embodiments of the methods and medical uses described herein, the effective dose is from about 2 mg to about 400 mg. In some embodiments of the methods and medical uses described herein, the effective dose is from about 10 mg to about 160 mg. In some embodiments of the methods and medical uses described herein, the effective dose is from about 2 mg to about 100 mg. In some embodiments of the methods and medical uses described herein, the effective dose is from about 2 mg to about 50 mg. In some embodiments of the methods and medical uses described herein, the effective dose is from about 2 mg to about 20 mg.

In some embodiments of the methods and medical uses described herein, Compound 1 is administered orally. In some embodiments of the methods and medical uses described herein, the effective dose is taken with food. In some embodiments of the methods and medical uses described herein, the effective dose is taken without food. In some embodiments of the methods and medical uses described herein, the effective dose is administered to the patient once per day. In some embodiments of the methods and medical uses described herein, the effective dose is administered to the patient twice per day. In some embodiments of the methods and medical uses described herein, the effective dose is administered to the patient three times per day.

Further disclosed herein are methods of treating inflammation or neuropathic pain in a patient in need thereof, comprising administering to the patient in need thereof a composition comprising Compound 1, or a pharmaceutically acceptable salt thereof, wherein administration of the composition provides a plasma $AUC_{0-inf}$ of at least 0.05 µM·hr. Further disclosed herein are methods of treating inflammation or neuropathic pain in a patient in need thereof, comprising administering to the patient in need thereof a composition comprising Compound 1, or a pharmaceutically acceptable salt thereof, wherein administration of the composition provides a plasma $AUC_{0-inf}$ of at least 0.1 µM·hr. Further disclosed herein are methods of treating inflammation or neuropathic pain in a patient in need thereof, comprising administering to the patient in need thereof a composition comprising Compound 1, or a pharmaceutically acceptable salt thereof, wherein administration of the composition provides a plasma $AUC_{0-inf}$ of at least 0.2 µM·hr.

Further disclosed herein are methods of treating inflammation or neuropathic pain in a patient in need thereof, comprising administering to the patient in need thereof a composition comprising Compound 1, or a pharmaceutically acceptable salt thereof, wherein administration of the composition increases the concentration of plasma 2-AG in the patient by at least 2-fold.

Further disclosed herein are methods of treating inflammation or neuropathic pain in a patient in need thereof, comprising administering to the patient in need thereof a composition comprising Compound 1, or a pharmaceutically acceptable salt thereof, wherein administration of the composition provides at least 30% of MGLL in PBMCs from the patient to be covalently attached to a fragment of Compound 1.

Further disclosed herein is also a composition comprising Compound 1, or a pharmaceutically acceptable salt thereof, for use in a method of treating inflammation or neuropathic pain of the human or animal body; wherein administration of the composition provides a plasma $AUC_{0-inf}$ of at least 0.05 µM·hr; or wherein administration of the composition provides a plasma $AUC_{0-inf}$ of at least 0.1 µM·hr; or wherein administration of the composition provides a plasma $AUC_{0-inf}$ of at least 0.2 µM·hr; or wherein administration of the composition increases the concentration of plasma 2-AG in the patient by at least 2-fold; or wherein administration of the composition provides at least 30% of MGLL in PBMCs from the patient to be covalently attached to a fragment of Compound 1.

Further disclosed herein are methods of treating Epilepsy/Seizure Disorder, Multiple Sclerosis, Neuromyelitis Optica (NMO), Tourette Syndrome, Alzheimer Disease, or abdominal pain associated with Irritable Bowel Syndrome in a patient in need thereof, comprising administering to the patient in need thereof a composition comprising Compound 1, or a pharmaceutically acceptable salt thereof, wherein administration of the composition provides a plasma $AUC_{0-inf}$ of at least 0.05 µM·hr. Further disclosed herein are methods of treating Epilepsy/Seizure Disorder, Multiple Sclerosis, Neuromyelitis Optica (NMO), Tourette Syndrome, Alzheimer Disease, or abdominal pain associated with Irritable Bowel Syndrome in a patient in need thereof, comprising administering to the patient in need thereof a composition comprising Compound 1, or a pharmaceutically acceptable salt thereof, wherein administration of the composition provides a plasma $AUC_{0-inf}$ of at least 0.1 µM·hr. Further disclosed herein are methods of treating Epilepsy/Seizure Disorder, Multiple Sclerosis, Neuromyelitis Optica (NMO), Tourette Syndrome, Alzheimer Disease, or abdominal pain associated with Irritable Bowel Syndrome in a patient in need thereof, comprising administering to the patient in need thereof a composition comprising Compound 1, or a pharmaceutically acceptable salt thereof, wherein administration of the composition provides a plasma $AUC_{0-inf}$ of at least 0.2 µM·hr.

Further disclosed herein are methods of treating acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia in a patient in need thereof, comprising administering to the patient in need thereof a composition comprising Compound 1, or a pharmaceutically acceptable salt thereof, wherein administration of the composition provides a plasma $AUC_{0-inf}$ of at least 0.05 µM·hr. Further disclosed herein are methods of treating acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia in a patient in need thereof, comprising administering to the patient in need thereof a composition comprising Compound 1, or a pharmaceutically acceptable salt thereof, wherein administration of the composition provides a plasma $AUC_{0-inf}$ of at least 0.1 µM·hr. Further disclosed herein are methods of treating acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia in a patient in need thereof, comprising administering to the patient in need thereof a composition comprising Compound 1, or a pharmaceutically acceptable salt thereof, wherein administration of the composition provides a plasma $AUC_{0-inf}$ of at least 0.2 µM·hr.

Further disclosed herein is also a composition comprising Compound 1, or a pharmaceutically acceptable salt thereof, for use in a method of treating Epilepsy/Seizure Disorder, Multiple Sclerosis, Neuromyelitis Optica (NMO), Tourette Syndrome, Alzheimer Disease, abdominal pain associated with Irritable Bowel Syndrome, acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia; wherein administration of the composition provides a plasma $AUC_{0\text{-}inf}$ of at least 0.05 µM·hr. Further disclosed herein is also a composition comprising Compound 1, or a pharmaceutically acceptable salt thereof, for use in a method of treating Epilepsy/Seizure Disorder, Multiple Sclerosis, Neuromyelitis Optica (NMO), Tourette Syndrome, Alzheimer Disease, abdominal pain associated with Irritable Bowel Syndrome, acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia; wherein administration of the composition provides a plasma $AUC_{0\text{-}inf}$ of at least 0.1 µM·hr. Further disclosed herein is also a composition comprising Compound 1, or a pharmaceutically acceptable salt thereof, for use in a method of treating Epilepsy/Seizure Disorder, Multiple Sclerosis, Neuromyelitis Optica (NMO), Tourette Syndrome, Alzheimer Disease, abdominal pain associated with Irritable Bowel Syndrome, acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia; wherein administration of the composition provides a plasma $AUC_{0\text{-}inf}$ of at least 0.2 µM·hr.

Further disclosed herein are methods of treating Epilepsy/Seizure Disorder, Multiple Sclerosis, Neuromyelitis Optica (NMO), Tourette Syndrome, Alzheimer Disease, or abdominal pain associated with Irritable Bowel Syndrome in a patient in need thereof, comprising administering to the patient in need thereof a composition comprising Compound 1, or a pharmaceutically acceptable salt thereof, wherein administration of the composition provides at least 30% of MGLL in PBMCs from the patient to be covalently attached to a fragment of Compound 1.

Further disclosed herein are methods of treating acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia in a patient in need thereof, comprising administering to the patient in need thereof a composition comprising Compound 1, or a pharmaceutically acceptable salt thereof, wherein administration of the composition provides at least 30% of MGLL in PBMCs from the patient to be covalently attached to a fragment of Compound 1.

Further disclosed herein is also thereof a composition comprising Compound 1, or a pharmaceutically acceptable salt thereof, for use in a method of treating Epilepsy/Seizure Disorder, Multiple Sclerosis, Neuromyelitis Optica (NMO), Tourette Syndrome, Alzheimer Disease, abdominal pain associated with Irritable Bowel Syndrome, acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia; wherein administration of the composition provides at least 30% of MGLL in PBMCs from the patient to be covalently attached to a fragment of Compound 1.

Further disclosed herein are methods and medical uses of increasing the concentration of plasma 2-AG in a subject using an effective dose of Compound 1, or a pharmaceutically acceptable salt thereof, wherein the concentration of plasma 2-AG in a subject is increased by at least 2-fold. In some embodiments, the concentration of plasma 2-AG in a subject is increased by at least 3-fold. In some embodiments, the concentration of plasma 2-AG in a subject is increased by at least 4-fold. In some embodiments, the concentration of plasma 2-AG in a subject is increased by at least 5-fold. In some embodiments, the concentration of plasma 2-AG in a subject is increased by at least 6-fold. In some embodiments, the concentration of plasma 2-AG in a subject is increased by at least 7-fold. In some embodiments, the concentration of plasma 2-AG in a subject is increased by at least 8-fold. In some embodiments, the concentration of plasma 2-AG in a subject is increased by at least 9-fold. In some embodiments, the concentration of plasma 2-AG in a subject is increased by at least 10-fold.

Further disclosed herein are methods of binding MGLL with Compound 1 in PBMCs in a subject after administration of an effective dose of Compound 1, or a pharmaceutically acceptable salt thereof, to the subject, wherein a fragment of Compound 1 is covalently attached to at least 30% MGLL in PBMCs. Further disclosed herein is Compound 1 or a pharmaceutically acceptable salt thereof, for use in any one of the methods of therapy disclosed herein, wherein after administration of an effective dose of Compound 1, a fragment of Compound 1 is covalently attached to at least 30% MGLL in PBMCs of a subject. In some embodiments, a fragment of Compound 1 is covalently attached to at least 40% of MGLL in PBMCs from the subject after administration of the effective dose. In some embodiments, a fragment of Compound 1 is covalently attached to at least 50% of MGLL in PBMCs from the subject after administration of the effective dose. In some embodiments, a fragment of Compound 1 is covalently attached to at least 60% of MGLL in PBMCs from the subject after administration of the effective dose. In some embodiments, a fragment of Compound 1 is covalently attached to at least 70% of MGLL in PBMCs from the subject after administration of the effective dose. In some embodiments, a fragment of Compound 1 is covalently attached to at least 80% of MGLL in PBMCs from the subject after administration of the effective dose. In some embodiments, a fragment of Compound 1 is covalently attached to at least 90% of MGLL in PBMCs from the subject after administration of the effective dose. In some embodiments, the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg. In some embodiments, Compound 1 is administered orally.

Further disclosed herein are pharmaceutical compositions comprising an effective dose of Compound 1, or a pharmaceutically acceptable salt thereof, and a pharmaceutically acceptable excipient, wherein the effective dose is from about 1 mg to about 500 mg. Further disclosed herein are pharmaceutical compositions for the treatment of inflammation or neuropathic pain, wherein the pharmaceutical composition comprises an effective dose of Compound 1, or a pharmaceutically acceptable salt thereof, and a pharmaceutically acceptable excipient, wherein the effective dose is from about 1 mg to about 500 mg. Further disclosed herein are pharmaceutical compositions for use in a method of treatment of inflammation or neuropathic pain of the human or animal body, wherein the pharmaceutical composition comprises an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Further disclosed herein are pharmaceutical compositions for the treatment of Epilepsy/Seizure Disorder, Multiple Sclerosis, Neuromyelitis Optica (NMO), Tourette Syndrome, Alzheimer Disease, or abdominal pain associated with Irritable Bowel Syndrome, wherein the pharmaceutical composition comprises an effective dose of Compound 1, or a pharmaceutically acceptable salt thereof, and a pharmaceutically acceptable excipient, wherein the effective dose is from about 1 mg to about 500 mg. Further disclosed herein are pharmaceutical compositions for use in a method of treatment of Epilepsy/Seizure Disorder, Multiple Sclerosis, Neuromyelitis Optica (NMO), Tourette Syndrome, Alzheimer Disease, or abdominal pain associated with Irritable Bowel Syndrome, wherein the pharmaceutical composition comprises an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Further disclosed herein are pharmaceutical compositions for the treatment of acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia, wherein the pharmaceutical composition comprises an effective dose of Compound 1, or a pharmaceutically acceptable salt thereof, and a pharmaceutically acceptable excipient, wherein the effective dose is from about 1 mg to about 500 mg. Further disclosed herein are pharmaceutical compositions for use in a method of treatment of acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia, wherein the pharmaceutical composition comprises an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

BRIEF DESCRIPTION OF THE DRAWINGS

The novel features of the invention are set forth with particularity in the appended claims. The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings re the following figures:

DETAILED DESCRIPTION OF THE INVENTION

Figure 1:
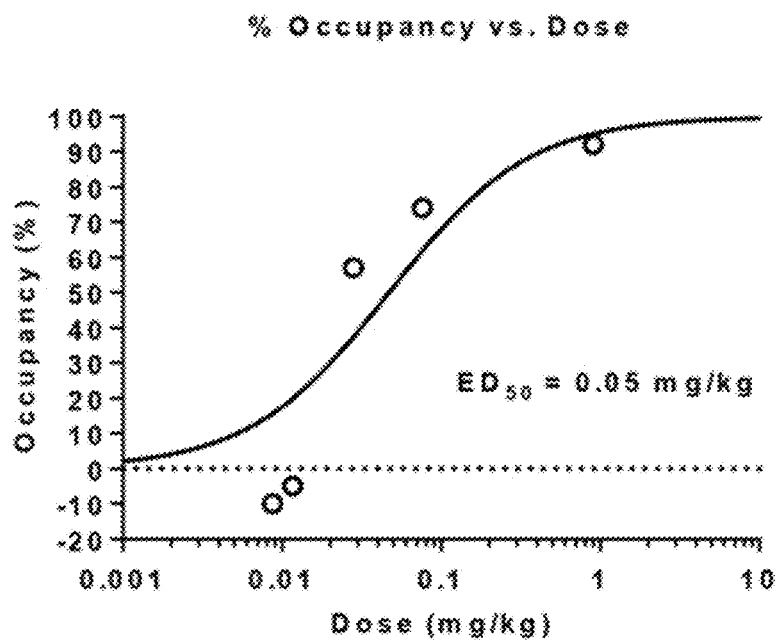
FIG. 1 shows the MGLL target engagement in the rhesus brain as a function of Compound 1 administered dose (IV administration).

MGLL is an enzyme that catalyzes the hydrolysis of the endocannabinoid 2-arachidonoylglycerol (2-AG), an endogenous ligand of the cannabinoid receptors $CB_1$ and $CB_2$, which are the molecular targets of the psychoactive component of Cannabis sativa, $\Delta^9$-tetrahydrocannabinol (THC). In rodents, MGLL is the major 2-AG hydrolase in the CNS as well as in most peripheral tissues and is the primary enzyme controlling the levels of 2-AG available to signal through $CB_{1,2}$.

$CB_1$ is the primary cannabinoid receptor in the nervous system and is widely distributed throughout the brain and at lower levels in peripheral tissues. Activation of $CB_1$ accounts for most of the neurobehavioral effects of THC and other exogenous cannabinoids (exocannabinoids) in rodents and humans. $CB_2$ is expressed primarily on immune cells and mediates the immunosuppressive effects of exocannabinoids. Direct activation of cannabinoid receptors by Cannabis preparations (e.g., Sativex®), THC (e.g., Marinol®), and cannabinoid agonists (e.g., Cesamet®) elicits therapeutically beneficial effects on pain, spasticity, sleep, appetite, and nausea.

The product of 2-AG hydrolysis, AA, is the metabolic precursor for the prostanoid family of signaling lipids. MGLL contributes to AA and prostanoid production in the rodent nervous system and select peripheral tissues, including the liver and lung. Genetic or pharmacologic inactivation of MGLL in mice reduces neuroinflammation in models of neurodegeneration through mechanisms independent of cannabinoid receptors, suggesting involvement of prostanoid suppression (Nomura, Science, 2011; Chen, Cell Reports, 2012; Piro, Cell Reports, 2012).

This disclosure is directed, at least in part, to methods of treating inflammation or neuropathic pain in a patient in need thereof, comprising administration to the patient in need thereof an effective dose of 1,1,1,3,3,3-hexafluoropropan-2-yl 4-(2-(pyrrolidin-1-yl)-4-(trifluoromethyl)benzyl) piperazine-1-carboxylate (Compound 1), or a pharmaceutically acceptable salt thereof. Further disclosed herein is Compound 1 or a pharmaceutically acceptable salt thereof, for use in a method of treating inflammation or neuropathic pain of the human or animal body. In another aspect, disclosed herein are methods of treating Epilepsy/Seizure Disorder, Multiple Sclerosis, Neuromyelitis Optica (NMO), Tourette Syndrome, Alzheimer Disease, or abdominal pain associated with Irritable Bowel Syndrome in a patient in need thereof, comprising administration to the patient in need thereof an effective dose of 1,1,1,3,3,3-hexafluoropropan-2-yl 4-(2-(pyrrolidin-1-yl)-4-(trifluoromethyl)benzyl) piperazine-1-carboxylate (Compound 1), or a pharmaceutically acceptable salt thereof. Further disclosed herein is Compound 1 or a pharmaceutically acceptable salt thereof, for use in a method of treating Epilepsy/Seizure Disorder, Multiple Sclerosis, Neuromyelitis Optica (NMO), Tourette Syndrome, Alzheimer Disease, or abdominal pain associated with Irritable Bowel Syndrome. In another aspect, disclosed herein are methods and medical uses to increase the concentration of plasma 2-arachidonoylglycerol (2-AG) in a subject at least 2- to 10-fold after administration to the subject an effective dose of Compound 1, or a pharmaceutically acceptable salt thereof. In another aspect, disclosed herein are methods and medical uses to bind at least 50% of MGLL in PBMCs in a subject using an effective dose of Compound 1, or a pharmaceutically acceptable salt thereof. In some embodiments, the methods and medical uses disclosed herein require an effective dose of Compound 1 ranging from about 1 mg to about 500 mg. In some embodiments, the methods and medical uses disclosed herein require an effective dose of Compound 1 ranging from about 1 mg to about 100 mg. In some embodiments, the methods and medical uses disclosed herein require an effective dose of Compound 1 ranging from about 2 mg to about 20 mg. In some embodiments, the methods and medical uses disclosed herein require a composition comprising Compound 1 which provides a plasma $AUC_{0-inf}$ of about 0.2 µM·hr to about 2.5 µM·hr in a subject after administration of Compound 1 to the subject.

Definitions

As used in the specification and appended claims, unless specified to the contrary, the following terms have the meaning indicated below.

The singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, use, or process, or the like, described herein, may "consist of" or "consist essentially of" the described features.

"Optional" or "optionally" means that a subsequently described event or circumstance may or may not occur and that the description includes instances when the event or circumstance occurs and instances in which it does not. For example, "optionally substituted aryl" means that the aryl radical is or is not be substituted and that the description includes both substituted aryl radicals and aryl radicals having no substitution.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

In some embodiments, "subject" and "patient" are used interchangeably. In some embodiments, "subject" refers to a healthy individual. In other embodiments, "subject" refers to a patient in need of treatment. In some embodiments, "subject" refers to a human or an animal, particularly a mammal. In some embodiments, "subject" refers to a human. In some embodiments, "subject" refers to a non-human mammal.

A "subject group" has a sufficient number of subjects to provide a statistically significant average measurement of a relevant pharmacokinetic parameter.

1,1,1,3,3,3-Hexafluoropropan-2-yl 4-(2-(pyrrolidin-1-yl)-4-(trifluoromethyl)benzyl)piperazine-1-carboxylate (Compound 1) is an irreversible inhibitor of MGLL. Alternate names include, but are not limited to, the following: 1-piperazinecarboxylic acid, 4-[[2-(1-pyrrolidinyl)-4-(trifluoromethyl)phenyl]methyl]-,2,2,2-trifluoro-1-(trifluoromethyl) ethyl ester; 1,1,1,3,3,3-hexafluoropropan-2-yl 4-{[2-(pyrrolidin-1-yl)-4-(trifluoromethyl) phenyl] methyl}piperazine-1-carboxylate; and 2,2,2-trifluoro-1-(trifluoromethyl)ethyl 4-{[2-(1-pyrrolidinyl)-4-(trifluoromethyl)phenyl]methyl}-1-piperazinecarboxylate. Compound 1 has the structure represented by:

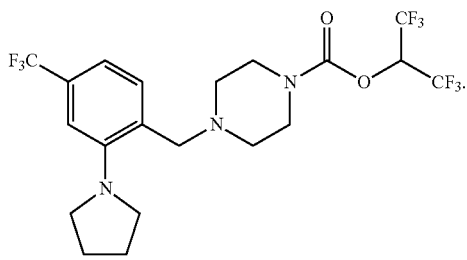 [SMILES: O=C(OC(C(F)(F)F)C(F)(F)F)N1CCN(Cc2ccc(C(F)(F)F)cc2N2CCCC2)CC1]

The preparation of Compound 1 was disclosed in WO 2013/103973, the content of which is incorporated by reference in its entirety.

In some embodiments, a pharmaceutically acceptable salt of Compound 1 is a hydrochloride salt. In further embodiments, the pharmaceutically acceptable salt of Compound 1 is a mono-hydrochloride salt.

In some embodiments, a fragment of Compound 1 is covalently attached to MGLL. In some embodiments, the fragment is:

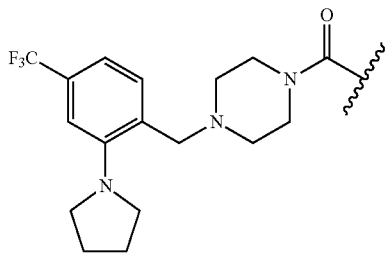

Methods
Neuropathic Pain and Inflammation

MGLL inhibitors are efficacious in several rodent models of pain including models of neuropathic pain (Kinsey, JPET, 2009). MGLL inhibitors also reduce disease and inflammation in multiple preclinical models. In the mouse experimental autoimmune encephalomyelitis model of multiple sclerosis, MGLL inhibition reduced disease severity, prevented demyelination and reduced inflammation (Bernal-Chico, Glia, 2015).

Disclosed herein are methods of treating pain or inflammation in a patient in need thereof, comprising administering to the patient in need thereof an effective dose of Compound 1, or a pharmaceutically acceptable salt thereof, wherein the effective dose is from about 1 mg to about 500 mg. In some embodiments, the method of treatment is for pain. In some embodiments, the method of treatment is for neuropathic pain. In some embodiments, the method of treatment is for inflammation. In some embodiments, the effective dose is from about 2 mg to about 400 mg. In some embodiments, the effective dose is from about 10 mg to about 160 mg. In some embodiments, the effective dose is from about 2 mg to about 20 mg. In some embodiments, the effective dose is selected from a group described herein. In some embodiments, the effective dose is administered orally.

Disclosed herein are methods of treating inflammation or neuropathic pain in a patient in need thereof, comprising administering to the patient in need thereof an effective dose of Compound 1, or a pharmaceutically acceptable salt thereof, wherein the effective dose is from about 1 mg to about 500 mg. In some embodiments, the method of treatment is for neuropathic pain. In some embodiments, the method of treatment is for inflammation. In some embodiments, the effective dose is from about 2 mg to about 400 mg. In some embodiments, the effective dose is from about 10 mg to about 160 mg. In some embodiments, the effective dose is from about 2 mg to about 20 mg. In some embodiments, the effective dose is selected from a group described herein. In some embodiments, the effective dose is administered orally.

Also disclosed herein are methods of treating inflammation or neuropathic pain in a patient in need thereof, comprising administering to the patient in need thereof an effective dose Compound 1, or a pharmaceutically acceptable salt thereof, wherein the concentration of plasma 2-AG of the patient increases at least 2-fold after administration of the effective dose. In some embodiments, the concentration of plasma 2-AG of the patient increases at least 3-fold after administration of the effective dose. In some embodiments, the concentration of plasma 2-AG of the patient increases at least 4-fold after administration of the effective dose. In some embodiments, the concentration of plasma 2-AG of the patient increases at least 5-fold after administration of the effective dose. In some embodiments, the concentration of plasma 2-AG of the patient increases at least 6-fold after administration of the effective dose. In some embodiments, the concentration of plasma 2-AG of the patient increases at least 7-fold after administration of the effective dose. In some embodiments, the concentration of plasma 2-AG of the patient increases at least 8-fold after administration of the effective dose. In some embodiments, the concentration of plasma 2-AG of the patient increases at least 9-fold after administration of the effective dose. In some embodiments, the concentration of plasma 2-AG of the patient increases at least 10-fold after administration of the effective dose. In some embodiments, the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 20 mg. In some embodiments, the effective dose is selected from a group described herein. In some embodiments, the method of treatment is for neuropathic pain. In some embodiments, the method of treatment is for inflammation. In some embodiments, the effective dose is administered orally.

Also disclosed herein are methods of treating inflammation or neuropathic pain in a patient in need thereof, comprising administering to the patient in need thereof an effective dose of Compound 1, or a pharmaceutically acceptable salt thereof, wherein a fragment of Compound 1 is covalently attached to at least 30% of MGLL in PBMCs from the patient after administration of the effective dose. In some embodiments, a fragment of Compound 1 is covalently attached to at least 40% of MGLL in PBMCs from the patient after administration of the effective dose. In some embodiments, a fragment of Compound 1 is covalently attached to at least 50% of MGLL in PBMCs from the patient after administration of the effective dose. In some embodiments, a fragment of Compound 1 is covalently attached to at least 60% of MGLL in PBMCs from the patient after administration of the effective dose. In some embodiments, a fragment of Compound 1 is covalently attached to at least 70% of MGLL in PBMCs from the patient after administration of the effective dose. In some embodiments, a fragment of Compound 1 is covalently attached to at least 80% of MGLL in PBMCs from the patient after administration of the effective dose. In some embodiments, a fragment of Compound 1 is covalently attached to at least 90% of MGLL in PBMCs from the patient after administration of the effective dose. In some embodiments, a fragment of Compound 1 is covalently attached to at least 95% of MGLL in PBMCs from the patient after administration of the effective dose. In some embodiments, the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg. In some embodiments, the effective dose is selected from a group described herein. In some embodiments, the method of treatment is for neuropathic pain. In some embodiments, the method of treatment is for inflammation. In some embodiments, the effective dose is administered orally.

Also disclosed herein are methods treating inflammation or neuropathic pain in a patient in need thereof, comprising administering to the patient in need thereof an effective dose of Compound 1, or a pharmaceutically acceptable salt thereof, wherein the plasma $AUC_{0-inf}$ of Compound 1 is at least 0.05 µM·hr after administration of the effective dose. Also disclosed herein are methods treating inflammation or neuropathic pain in a patient in need thereof, comprising administering to the patient in need thereof an effective dose of Compound 1, or a pharmaceutically acceptable salt thereof, wherein the plasma $AUC_{0-inf}$ of Compound 1 is at least 0.01 µM·hr after administration of the effective dose. Also disclosed herein are methods treating inflammation or neuropathic pain in a patient in need thereof, comprising administering to the patient in need thereof an effective dose of Compound 1, or a pharmaceutically acceptable salt thereof, wherein the plasma $AUC_{0-inf}$ of Compound 1 is at least 0.1 µM·hr after administration of the effective dose. Also disclosed herein are methods treating inflammation or neuropathic pain in a patient in need thereof, comprising administering to the patient in need thereof an effective dose of Compound 1, or a pharmaceutically acceptable salt thereof, wherein the plasma $AUC_{0-inf}$ of Compound 1 is at least 0.2 µM·hr after administration of the effective dose. In some embodiments, the plasma $AUC_{0-inf}$ of Compound 1 is at least 0.3 µM·hr after administration of the effective dose. In some embodiments, the plasma $AUC_{0-inf}$ of Compound 1 is at least 0.4 µM·hr after administration of the effective dose. In some embodiments, the plasma $AUC_{0-inf}$ of Compound 1 is at least 0.5 µM·hr after administration of the effective dose. In some embodiments, the plasma $AUC_{0-inf}$ of Compound 1 is at least 0.6 µM·hr after administration of the effective dose. In some embodiments, the plasma $AUC_{0-inf}$ of Compound 1 is at least 0.7 µM·hr after administration of the effective dose. In some embodiments, the plasma $AUC_{0-inf}$ of Compound 1 is at least 0.8 µM·hr after administration of the effective dose. In some embodiments, the plasma $AUC_{0-inf}$ of Compound 1 is at least 0.9 µM·hr after administration of the effective dose. In some embodiments, the plasma $AUC_{0-inf}$ of Compound 1 is at least 1.0 µM·hr after administration of the effective dose. In some embodiments, the plasma $AUC_{0-inf}$ of Compound 1 is at least 1.5 µM·hr after administration of the effective dose. In some embodiments, the plasma $AUC_{0-inf}$ of Compound 1 is at least 2.0 µM·hr after administration of the effective dose. In some embodiments, the plasma $AUC_{0-inf}$ of Compound 1 is at least 2.5 µM·hr after administration of the effective dose. In some embodiments, the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg. In some embodiments, the effective dose is selected from a group described herein. In some embodiments, the method of treatment is for neuropathic pain. In some embodiments, the method of treatment is for inflammation. In some embodiments, the effective dose is administered orally.

Also disclosed herein are methods treating inflammation or neuropathic pain in a patient in need thereof, comprising administering to the patient in need thereof an effective dose of Compound 1, or a pharmaceutically acceptable salt thereof, wherein the steady state plasma $AUC_{0-inf}$ of Compound 1 is at least 0.05 µM·hr after administration of the effective dose. Also disclosed herein are methods treating inflammation or neuropathic pain in a patient in need thereof, comprising administering to the patient in need thereof an effective dose of Compound 1, or a pharmaceutically acceptable salt thereof, wherein the steady state plasma $AUC_{0-inf}$ of Compound 1 is at least 0.01 µM·hr after administration of the effective dose. Also disclosed herein are methods treating inflammation or neuropathic pain in a patient in need thereof, comprising administering to the patient in need thereof an effective dose of Compound 1, or a pharmaceutically acceptable salt thereof, wherein the steady state plasma $AUC_{0-inf}$ of Compound 1 is at least 0.1 µM·hr after administration of the effective dose. Also disclosed herein are methods treating inflammation or neuropathic pain in a patient in need thereof, comprising administering to the patient in need thereof an effective dose of Compound 1, or a pharmaceutically acceptable salt thereof, wherein the steady state plasma $AUC_{0-inf}$ of Compound 1 is at least 0.2 µM·hr after administration of the effective dose. In some embodiments, the steady state plasma $AUC_{0-inf}$ of Compound 1 is at least 0.3 µM·hr after administration of the effective dose. In some embodiments, the steady state plasma $AUC_{0-inf}$ of Compound 1 is at least 0.4 µM·hr after administration of the effective dose. In some embodiments, the steady state plasma $AUC_{0-inf}$ of Compound 1 is at least 0.5 µM·hr after administration of the effective dose. In some embodiments, the steady state plasma $AUC_{0-inf}$ of Compound 1 is at least 0.6 µM·hr after administration of the effective dose. In some embodiments, the steady state plasma $AUC_{0-inf}$ of Compound 1 is at least 0.7 µM·hr after administration of the effective dose. In some embodiments, the steady state plasma $AUC_{0-inf}$ of Compound 1 is at least 0.8 µM·hr after administration of the effective dose. In some embodiments, the steady state plasma $AUC_{0-inf}$ of Compound 1 is at least 0.9 µM·hr after administration of the effective dose. In some embodiments, the steady state plasma $AUC_{0-inf}$ of Compound 1 is at least 1.0 µM·hr after administration of the effective dose. In some embodiments, the steady state plasma $AUC_{0-inf}$ of Compound 1 is at least 1.5 µM·hr after administration of the effective dose. In some embodiments, the steady state plasma $AUC_{0-inf}$ of Compound 1 is at least 2.0 µM·hr after administration of the effective dose. In some embodiments, the steady state plasma $AUC_{0-inf}$ of Compound 1 is at least 2.5 µM·hr after administration of the effective dose. In some embodiments, the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg. In some embodiments, the effective dose is selected from a group described herein. In some embodiments, the method of treatment is for neuropathic pain. In some embodiments, the method of treatment is for inflammation. In some embodiments, the effective dose is administered orally.

Also disclosed herein are methods treating inflammation or neuropathic pain in a patient in need thereof, comprising administering to the patient in need thereof an effective dose of Compound 1, or a pharmaceutically acceptable salt thereof, wherein after administration of the effective dose: (a) the concentration of plasma 2-AG of the patient increases at least 2-fold; and (b) a fragment of Compound 1 is covalently attached to at least 30% of MGLL in PBMCs from the patient. In some embodiments, the concentration of plasma 2-AG of the patient increases at least 3-fold after administration of the effective dose. In some embodiments, the concentration of plasma 2-AG of the patient increases at least 4-fold after administration of the effective dose. In some embodiments, the concentration of plasma 2-AG of the patient increases at least 5-fold after administration of the effective dose. In some embodiments, the concentration of plasma 2-AG of the patient increases at least 6-fold after administration of the effective dose. In some embodiments, the concentration of plasma 2-AG of the patient increases at least 7-fold after administration of the effective dose. In some embodiments, the concentration of plasma 2-AG of the patient increases at least 8-fold after administration of the effective dose. In some embodiments, the concentration of plasma 2-AG of the patient increases at least 9-fold after administration of the effective dose. In some embodiments, the concentration of plasma 2-AG of the patient increases at least 10-fold after administration of the effective dose. In some embodiments, a fragment of Compound 1 is covalently attached to at least 40% of MGLL in PBMCs from the patient after administration of the effective dose. In some embodiments, a fragment of Compound 1 is covalently attached to at least 50% of MGLL in PBMCs from the patient after administration of the effective dose. In some embodiments, a fragment of Compound 1 is covalently attached to at least 60% of MGLL in PBMCs from the patient after administration of the effective dose. In some embodiments, a fragment of Compound 1 is covalently attached to at least 70% of MGLL in PBMCs from the patient after administration of the effective dose. In some embodiments, a fragment of Compound 1 is covalently attached to at least 80% of MGLL in PBMCs from the patient after administration of the effective dose. In some embodiments, a fragment of Compound 1 is covalently attached to at least 90% of MGLL in PBMCs from the patient after administration of the effective dose. In some embodiments, a fragment of Compound 1 is covalently attached to at least 95% of MGLL in PBMCs from the patient after administration of the effective dose. In some embodiments, the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg. In some embodiments, the effective dose is selected from a group described herein. In some embodiments, the method of treatment is for neuropathic pain. In some embodiments, the method of treatment is for inflammation. In some embodiments, the effective dose is administered orally.

Also disclosed herein are methods of treating inflammation or neuropathic pain in a patient in need thereof, comprising administering to the patient in need thereof a composition comprising an effective dose of Compound 1, or a pharmaceutically acceptable salt thereof, wherein the effective dose is from about 1 mg to about 500 mg. In some embodiments, the method of treatment is for neuropathic pain. In some embodiments, the method of treatment is for inflammation. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg. In some embodiments, the effective dose is selected from a group described herein. In some embodiments, the composition is administered orally.

Also disclosed herein are methods of treating inflammation or neuropathic pain in a patient in need thereof, comprising administering to the patient in need thereof a composition comprising Compound 1, or a pharmaceutically acceptable salt thereof, wherein administration of the composition provides a plasma $AUC_{0-inf}$ of at least 0.05 µM·hr. Also disclosed herein are methods of treating inflammation or neuropathic pain in a patient in need thereof, comprising administering to the patient in need thereof a composition comprising Compound 1, or a pharmaceutically acceptable salt thereof, wherein administration of the composition provides a plasma $AUC_{0-inf}$ of at least 0.01 µM·hr. Also disclosed herein are methods of treating inflammation or neuropathic pain in a patient in need thereof, comprising administering to the patient in need thereof a composition comprising Compound 1, or a pharmaceutically acceptable salt thereof, wherein administration of the composition provides a plasma $AUC_{0-inf}$ of at least 0.1 µM·hr. Also disclosed herein are methods of treating inflammation or neuropathic pain in a patient in need thereof, comprising administering to the patient in need thereof a composition comprising Compound 1, or a pharmaceutically acceptable salt thereof, wherein administration of the composition provides a plasma $AUC_{0-inf}$ of at least 0.2 µM·hr. In some embodiments, administration of the composition provides a plasma $AUC_{0-inf}$ of at least 0.3 µM·hr, at least 0.4 µM·hr, at least 0.5 µM·hr, at least 0.6 µM·hr, at least 0.7 µM·hr, at least 0.8 µM·hr, at least 0.9 µM·hr, at least 1.0 µM·hr, at least 1.1 µM·hr, at least 1.2 µM·hr, at least 1.3 µM·hr, at least 1.4 µM·hr, at least 1.5 µM·hr, at least 1.6 µM·hr, at least 1.7 µM·hr, at least 1.8 µM·hr, at least 1.9 µM·hr, at least 2.0 µM·hr, at least 2.1 µM·hr, at least 2.2 µM·hr, at least 2.3 µM·hr, at least 2.4 µM·hr, at least 2.5 µM·hr, at least 2.6 µM·hr, at least 2.7 µM·hr, at least 2.8 µM·hr, at least 2.9 µM·hr, or at least 3.0 µM·hr. In some embodiments, the composition comprises from about 1 mg to about 500 mg of Compound 1, or a pharmaceutically acceptable salt thereof. In some embodiments, the composition comprises from about 2 mg to about 400 mg of Compound 1, or a pharmaceutically acceptable salt thereof. In some embodiments, the composition comprises from about 10 mg to about 160 mg of Compound 1, or a pharmaceutically acceptable salt thereof. In some embodiments, the composition comprises from about 2 mg to about 20 mg of Compound 1, or a pharmaceutically acceptable salt thereof. In some embodiments, the composition is administered orally.

Also described herein are methods of treating inflammation or neuropathic pain in a patient in need thereof, comprising administering to the patient in need thereof a composition comprising Compound 1, or a pharmaceutically acceptable salt thereof, wherein administration of the composition increases the concentration of plasma 2-AG in the patient by at least 2-fold. In some embodiments, administration of the composition increases the concentration of plasma 2-AG in the patient by at least 3-fold, at least 4-fold, at least 5-fold, at least 6-fold, at least 7-fold, at least 8-fold, at least 9-fold, or at least 10-fold. In some embodiments, the composition comprises from about 1 mg to about 500 mg of Compound 1, or a pharmaceutically acceptable salt thereof. In some embodiments, the composition comprises from about 2 mg to about 400 mg of Compound 1, or a pharmaceutically acceptable salt thereof. In some embodiments, the composition comprises from about 10 mg to about 160 mg of Compound 1, or a pharmaceutically acceptable salt thereof. In some embodiments, the composition comprises from about 2 mg to about 20 mg of Compound 1, or a pharmaceutically acceptable salt thereof. In some embodiments, the composition is administered orally.

Also disclosed herein are methods of treating inflammation or neuropathic pain in a patient in need thereof, comprising administering to the patient in need thereof a composition comprising Compound 1, or a pharmaceutically acceptable salt thereof, wherein administration of the composition provides at least 30% of MGLL in PBMCs from the patient to be covalently attached to a fragment of Compound 1. In some embodiments, administration of the composition provides at least 40%, at least 50%, at least 60%, at least 70%, at least 80%, at least 90%, or at least 95%, of MGLL in PBMCs from the patient to be covalently attached to a fragment of Compound 1. In some embodiments, the composition comprises from about 1 mg to about 500 mg of Compound 1, or a pharmaceutically acceptable salt thereof. In some embodiments, the composition comprises from about 2 mg to about 400 mg of Compound 1, or a pharmaceutically acceptable salt thereof. In some embodiments, the composition comprises from about 10 mg to about 160 mg of Compound 1, or a pharmaceutically acceptable salt thereof. In some embodiments, the composition comprises from about 2 mg to about 20 mg of Compound 1, or a pharmaceutically acceptable salt thereof. In some embodiments, the composition is administered orally.

Also described herein are methods of treating inflammation or neuropathic pain in a patient in need thereof, comprising administering to the patient in need thereof a composition comprising Compound 1, or a pharmaceutically acceptable salt thereof, wherein administration of the composition (a) increases the concentration of plasma 2-AG in the patient by at least 2-fold and (b) provides at least 30% of MGLL in PBMCs from the patient to be covalently attached to a fragment of Compound 1.

Also described herein are methods of treating inflammation or neuropathic pain in a patient in need thereof, comprising administering to the patient in need thereof a composition comprising Compound 1, or a pharmaceutically acceptable salt thereof, wherein administration of the composition (a) provides a plasma $AUC_{0-inf}$ of at least 0.05 µM·hr; (b) increases the concentration of plasma 2-AG in the patient by at least 2-fold; and (c) provides at least 30% of MGLL in PBMCs from the patient to be covalently attached to a fragment of Compound 1. Also described herein are methods of treating inflammation or neuropathic pain in a patient in need thereof, comprising administering to the patient in need thereof a composition comprising Compound 1, or a pharmaceutically acceptable salt thereof, wherein administration of the composition (a) provides a plasma $AUC_{0-inf}$ of at least 0.01 µM·hr; (b) increases the concentration of plasma 2-AG in the patient by at least 2-fold; and (c) provides at least 30% of MGLL in PBMCs from the patient to be covalently attached to a fragment of Compound 1. Also described herein are methods of treating inflammation or neuropathic pain in a patient in need thereof, comprising administering to the patient in need thereof a composition comprising Compound 1, or a pharmaceutically acceptable salt thereof, wherein administration of the composition (a) provides a plasma $AUC_{0-inf}$ of at least 0.1 µM·hr; (b) increases the concentration of plasma 2-AG in the patient by at least 2-fold; and (c) provides at least 30% of MGLL in PBMCs from the patient to be covalently attached to a fragment of Compound 1. Also described herein are methods of treating inflammation or neuropathic pain in a patient in need thereof, comprising administering to the patient in need thereof a composition comprising Compound 1, or a pharmaceutically acceptable salt thereof, wherein administration of the composition (a) provides a plasma $AUC_{0-inf}$ of at least 0.2 µM·hr; (b) increases the concentration of plasma 2-AG in the patient by at least 2-fold; and (c) provides at least 30% of MGLL in PBMCs from the patient to be covalently attached to a fragment of Compound 1.

Acute Pain, Inflammatory Pain, Cancer Pain, and Pain Caused by Peripheral Neuropathy MGLL inhibitors have shown efficacy in several rodent models of pain including models of acute pain (Long, Nature Chemical Biology, 2009), inflammatory pain (Anderson, Neuropharmacology, 2013), cancer pain (Khasabova, Pharmacology Research, 2011), and pain caused by chemotherapy-induced peripheral neuropathy (Guindon, Pharmacology Research, 2013).

In some embodiments, disclosed herein is a method of treating acute pain, in a patient in need thereof, comprising administering to the patient in need thereof an effective dose of Compound 1, or a pharmaceutically acceptable salt thereof. In some embodiments is a method of treating acute pain, in a patient in need thereof, comprising administering to the patient in need thereof an effective dose of Compound 1, or a pharmaceutically acceptable salt thereof, wherein the effective dose is from about 1 mg to about 100 mg. In some embodiments, disclosed herein is a method of treating inflammatory pain, in a patient in need thereof, comprising administering to the patient in need thereof an effective dose of Compound 1, or a pharmaceutically acceptable salt thereof. In some embodiments is a method of treating inflammatory pain, in a patient in need thereof, comprising administering to the patient in need thereof an effective dose of Compound 1, or a pharmaceutically acceptable salt thereof, wherein the effective dose is from about 1 mg to about 100 mg. In some embodiments, disclosed herein is a method of treating cancer pain, in a patient in need thereof, comprising administering to the patient in need thereof an effective dose of Compound 1, or a pharmaceutically acceptable salt thereof. In some embodiments is a method of treating cancer pain, in a patient in need thereof, comprising administering to the patient in need thereof an effective dose of Compound 1, or a pharmaceutically acceptable salt thereof, wherein the effective dose is from about 1 mg to about 100 mg. In some embodiments, disclosed herein is a method of treating pain caused by peripheral neuropathy, in a patient in need thereof, comprising administering to the patient in need thereof an effective dose of Compound 1, or a pharmaceutically acceptable salt thereof. In some embodiments is a method of treating pain caused by peripheral neuropathy, in a patient in need thereof, comprising administering to the patient in need thereof an effective dose of Compound 1, or a pharmaceutically acceptable salt thereof, wherein the effective dose is from about 1 mg to about 100 mg. Disclosed also herein is Compound 1, or a pharmaceutically acceptable salt thereof, for use in a method of treating acute pain, optionally comprising administering a dose from about 1 mg to about 100 mg.

Central Pain

Central pain is neuropathic pain caused by lesion or dysfunction of the central nervous system, for example, post-stroke, multiple sclerosis, neuromyelitis optica, idiopathic inflammatory transverse myelitis, spinal cord injury, brachial-radial pain syndrome, and central craniofacial pain. Exocannabinoids have demonstrated activity in central pain associated with multiple sclerosis. A 4-week randomized double-blind placebo-controlled parallel group trial with MS and central pain using an oromucosal spray, THC/CBD, containing the $CB_1$ agonist delta-9-tetrahydrocannabinol and cannabidiol (another *Cannabis*-derived alcohol) showed that the active agent was superior to placebo in reducing the mean intensity of pain (NRS-11) and of sleep disturbance (Rog, Neurology, 2005, 65(6), 812-9). The same THC/CBD preparation was studied in a larger group of MS patients with central neuropathic pain utilizing a two-stage design; in the second phase of this study, the time to treatment failure (primary endpoint) statistically favored THC/CBD, as did an improvement in the Pain NRS-11 and sleep quality (Langford, J Neurol, 2013, 260(4), 984-97). Additionally, nabilone, a synthetic $CB_1$ agonist structurally related to THC, showed efficacy in MS-induced central neuropathic pain (Turcotte, Pain Med, 2015, 16(1), 149-59). Several studies of exocannabinoids in central pain have indicated activity, suggesting MGLL inhibitors may also have efficacy in treatment of central pain.

In some embodiments, disclosed herein is a method of treating central pain, in a patient in need thereof, comprising administering to the patient in need thereof an effective dose of Compound 1, or a pharmaceutically acceptable salt thereof. In some embodiments is a method of treating central pain, in a patient in need thereof, comprising administering to the patient in need thereof an effective dose of Compound 1, or a pharmaceutically acceptable salt thereof, wherein the effective dose is from about 1 mg to about 100 mg. Disclosed also herein is Compound 1, or a pharmaceutically acceptable salt thereof, for use in a method of treating central pain, optionally comprising administering a dose from about 1 mg to about 100 mg.

Fibromyalgia

Fibromyalgia (FM) is a common, chronic, idiopathic condition characterized by diffuse body pain and the presence of pressure allodynia. Duloxetine and pregabalin are specifically labeled for the treatment of pain in FM, and tricyclic antidepressants like amitriptyline, while not specifically labeled for FM treatment, are first-line agents. There is no clear pathological understanding of FM, and no validated preclinical model. However, several studies of exocannabinoids in FM have indicated activity, suggesting MGLL inhibitors may also have efficacy in treatment of FM. Measures of pain (e.g., NRS-11, Pain VAS) and the Fibromyalgia Impact Questionnaire (FIQ), which measures limitations in several activities of daily living impacted by FM, have demonstrated activity of drugs in FM clinical trials (Burckhardt, J Rheumatol, 1991, 18(5), 728-33; Mease, J Rheumatol, 2008, 35(3), 502-14). A survey of Spanish FM patients who were cannabis users and non-users was performed to identify the effects of cannabis on a range of disease symptoms such as pain, stiffness, well-being, relaxation and drowsiness; perceived relief was common for pain, sleep disturbances, stiffness mood disorders and anxiety (Fiz, PLoS One, 2011, 6(4), e18440). In an 8-week, 40-patient study, compared with placebo the exocannabinoid nabilone improved pain measured on a 10 cm VAS, and improved the FIQ domain of anxiety and the FIQ total score (Skrabek, J Pain, 2008, 9(2), 164-73). In a 31-patient study, compared with amitriptyline nabilone improved the index of sleep (Insomnia Severity Index) and was judged non-inferior on measures of pain (McGill Pain Questionnaire) and the FIQ (Ware, Anesth Analg, 2010, 110(2), 604-10).

In some embodiments, disclosed herein is a method of treating fibromyalgia, in a patient in need thereof, comprising administering to the patient in need thereof an effective dose of Compound 1, or a pharmaceutically acceptable salt thereof. In some embodiments is a method of treating fibromyalgia, in a patient in need thereof, comprising administering to the patient in need thereof an effective dose of Compound 1, or a pharmaceutically acceptable salt thereof, wherein the effective dose is from about 1 mg to about 100 mg. Disclosed also herein is Compound 1, or a pharmaceutically acceptable salt thereof, for use in a method of treating fibromyalgia, optionally comprising administering a dose from about 1 mg to about 100 mg.

Migraine

Migraine is a common episodic disorder of head and facial pain. Migraine attacks can be acutely treated with NSAIDs, acetaminophen, a variety of triptans (e.g., sumatriptan), and antiemetics, but some migraine sufferers have pain unresponsive to existing treatment options. Data suggests that endocannabinoid pathways may be relevant in migraine. In patients with chronic migraine and probable analgesic-overuse headache, CSF samples showed higher levels of the endocannabinoid palmitoylethanolamide and lower levels of anandamide compared with healthy controls (Sarchielli, Neuropsychopharmacology, 2007, 32(6), 1384-90). In addition, a retrospective chart review of patients attending a medical marijuana clinic with a primary diagnosis of migraine headaches found a decrease in the frequency of migraine headaches after initiating marijuana therapy (Rhyne, Pharmacotherapy, 2016), suggesting MGLL inhibitors may also have efficacy in treatment of migraine.

In some embodiments, disclosed herein is a method of treating migraine, in a patient in need thereof, comprising administering to the patient in need thereof an effective dose of Compound 1, or a pharmaceutically acceptable salt thereof. In some embodiments is a method of treating migraine, in a patient in need thereof, comprising administering to the patient in need thereof an effective dose of Compound 1, or a pharmaceutically acceptable salt thereof, wherein the effective dose is from about 1 mg to about 100 mg. Disclosed also herein is Compound 1, or a pharmaceutically acceptable salt thereof, for use in a method of treating migraine, optionally comprising administering a dose from about 1 mg to about 100 mg.

Vasoocclusive Painful Crisis in Sickle Cell Disease

Vasoocclusive painful crisis is believed to be the result of altered rheology of red blood cells (RBC) with occlusion of microcapillaries and ischemic pain in patients with sickle cell disease (SCD), a hereditary condition due to mutations in the adult hemoglobin beta gene. Vasoocclusive painful crisis in SCD is typically treated with oral or intravenous opioid analgesics; chronic opioids may be used in half of adult patients. Neuropathic pain can occur with greater age, manifest by hyperalgesia and allodynia; medicines for chronic neuropathic pain are sometimes used in these patients. A survey of patients with SCD in London identified 36% of questionnaire respondents had used cannabis in the previous year to relieve symptoms (chiefly pain) associated with SCD (Howard, Br J Haematol, 2005, 131(1), 123-8). Additionally, pain-related behaviors and neurochemical alterations in mice expressing human sickle hemoglobin were markedly improved by the cannabinoid receptor agonist CP-55940 (Kohli, Blood, 2010, 116(3), 456-65). This data suggests that MGLL inhibitors are potential therapeutic agents for treating vasoocclusive painful crisis in SCD.

In some embodiments, disclosed herein is a method of treating vasoocclusive painful crisis in sickle cell disease, in a patient in need thereof, comprising administering to the patient in need thereof an effective dose of Compound 1, or a pharmaceutically acceptable salt thereof. In some embodiments is a method of treating vasoocclusive painful crisis in sickle cell disease, in a patient in need thereof, comprising administering to the patient in need thereof an effective dose of Compound 1, or a pharmaceutically acceptable salt thereof, wherein the effective dose is from about 1 mg to about 100 mg. Disclosed also herein is Compound 1, or a pharmaceutically acceptable salt thereof, for use in a method of treating vasoocclusive painful crisis in cickel cell disease, optionally comprising administering a dose from about 1 mg to about 100 mg.

Multiple Sclerosis Symptomatic Treatment

Nearly all multiple sclerosis (MS) patients of all subtypes have one or more symptoms of spasticity, pain, disturbed sleep, bladder dysfunction, and fatigue. Disease modifying therapies do not improve symptoms. Spasticity affects over 80% of MS patients; 34% have moderate, severe, or total spasticity. Severe spasticity is related to cost and level of care, and is independently related to quality of life in MS. Two recent reviews support the use of exocannabinoids for the treatment of MS spasticity and pain (Whiting, JAMA, 2015, 313(24), 2456-2473; Hill, JAMA, 2015, 313(24), 2474-83).

An exocannabinoid preparation is an approved treatment for spasticity associated with multiple sclerosis. Sativex, an oromucosal spray mixture of the $CB_1$ agonist THC and another cannabis plant derived alcohol, cannabidiol, was shown to decrease self-reported spasticity related symptoms. In a pivotal trial of Sativex using a randomized withdrawal design, there was improvement with continuing Sativex in spasm frequency, sleep disruption by spasticity, subject global impression of change, carer global impression of change, and physician global impression of change. Other clinical trials have shown activity of a variety of exocannabinoids in spasticity due to multiple sclerosis (Zajicek, Lancet, 2003, 362(9395), 1517-26; Collin, Eur J Neurol, 2007, 14(3), 290-6; Collin, Neurol Res, 2010. 32(5); 451-9). These parallel group studies exemplify the clinical trial design and endpoints that could be used to show a MGLL benefits spasticity in MS.

In some embodiments, disclosed herein is a method of treating spasticity or pain associated with multiple sclerosis, in a patient in need thereof, comprising administering to the patient in need thereof an effective dose of Compound 1, or a pharmaceutically acceptable salt thereof. In some embodiments is a method of treating spasticity or pain associated with multiple sclerosis, in a patient in need thereof, comprising administering to the patient in need thereof an effective dose of Compound 1, or a pharmaceutically acceptable salt thereof, wherein the effective dose is from about 1 mg to about 100 mg. Disclosed also herein is Compound 1, or a pharmaceutically acceptable salt thereof, for use in a method of treating spasticity or pain associated with multiple sclerosis, optionally comprising administering a dose from about 1 mg to about 100 mg.

Functional Chest Pain

Functional chest pain, sometimes called non-GERD, non-cardiac chest pain, is a functional gastrointestinal disorder where discomfort of upper GI structures is perceived in the chest. In addition to consuming medical resources to rule out other treatable conditions, functional chest pain causes distress for patients. It may be treated with tricyclic antidepressants or serotonin norepinephrine reuptake inhbitiros, but not all patients respond. In patients with functional chest pain, a syndrome ascribed to GI hypersensitivity, the exocannabinoid dronabinol improved chest pain symptoms and raised sensory threshold for balloon distension of the esophagus in a placebo-controlled 4 week study (Malik, Dis Esophagus, 2016, online pub. DOI: 10.1111/dote. 12455), suggesting MGLL inhibitors may also have efficacy in treatment of functional chest pain.

In some embodiments, disclosed herein is a method of treating functional chest pain, in a patient in need thereof, comprising administering to the patient in need thereof an effective dose of Compound 1, or a pharmaceutically acceptable salt thereof. In some embodiments is a method of treating functional chest pain, in a patient in need thereof, comprising administering to the patient in need thereof an effective dose of Compound 1, or a pharmaceutically acceptable salt thereof, wherein the effective dose is from about 1 mg to about 100 mg. Disclosed also herein is Compound 1, or a pharmaceutically acceptable salt thereof, for use in a method of treating functional chest pain, optionally comprising administering a dose from about 1 mg to about 100 mg.

Rheumatoid Arthritis and Osteoarthritis $CB_1$ and $CB_2$ receptors were found to be present in the synovia of rheumatoid arthritis (RA) and osteoarthritis (OA) patients. The endocannabinoids anandamide and 2-AG were identified in synovial fluid of RA and OA patients, but not in normal volunteers (Richardson, Arthritis Res Ther, 2008, 10(2), R43). In addition, a small RA patient trial with nabiximols (THC/CBD oromucosal spray) showed improved pain on movement at rest, improved sleep, and an improvement in the standard RA Disease Activity Score in 28 joints (DAS28) (Blake, Rheumatology (Oxford), 2006, 45(1), 50-2). These data predict that MGLL may be an important therapeutic target for the treatment of pain and inflammation in RA and OA.

In some embodiments, disclosed herein is a method of treating rheumatoid arthritis or osteoarthritis, in a patient in need thereof, comprising administering to the patient in need thereof an effective dose of Compound 1, or a pharmaceutically acceptable salt thereof. In some embodiments is a method of treating rheumatoid arthritis or osteoarthritis, in a patient in need thereof, comprising administering to the patient in need thereof an effective dose of Compound 1, or a pharmaceutically acceptable salt thereof, wherein the effective dose is from about 1 mg to about 100 mg. In some embodiments, disclosed herein is a method of treating rheumatoid arthritis pain or osteoarthritis pain, in a patient in need thereof, comprising administering to the patient in need thereof an effective dose of Compound 1, or a pharmaceutically acceptable salt thereof. In some embodiments is a method of treating rheumatoid arthritis pain or osteoarthritis pain, in a patient in need thereof, comprising administering to the patient in need thereof an effective dose of Compound 1, or a pharmaceutically acceptable salt thereof, wherein the effective dose is from about 1 mg to about 100 mg. Disclosed also herein is Compound 1, or a pharmaceutically acceptable salt thereof, for use in a method of treating rheumatoid arthritis or osteoarthritis, optionally comprising administering a dose from about 1 mg to about 100 mg.

Alzheimer's Disease

Alzheimer's disease (AD) is the most common cause of dementia, affecting ~5.3 million people in the US. Agitation and aggression are risk factors for institutionalization of patients with dementia. The exocannabinoid dronabinol improved anorexia and decreased agitation in AD patients (Volicer, Int J Geriatr Psychiatry, 1997, 12(9), 913-9) and reduced nighttime agitation in AD patients (Walther, J Clin Psychopharmacol, 2011, 31(2), 256-8). A MGLL inhibitor could be tested in either a parallel group or a crossover study of selected AD patients with dementia and agitation. As an example, the CIT-AD trial measured agitation in patients randomized to psychosocial intervention plus either placebo or citalopram for 9 weeks (Porsteinsson, JAMA, 2014, 311(7), 682-91).

In some embodiments, disclosed herein is a method of treating agitation or agression associated with Alzheimer's disease, in a patient in need thereof, comprising administering to the patient in need thereof an effective dose of Compound 1, or a pharmaceutically acceptable salt thereof. In some embodiments is a method of treating agitation or agression associated with Alzheimer's disease, in a patient in need thereof, comprising administering to the patient in need thereof an effective dose of Compound 1, or a pharmaceutically acceptable salt thereof, wherein the effective dose is from about 1 mg to about 100 mg. Disclosed also herein is Compound 1, or a pharmaceutically acceptable salt thereof, for use in a method of treating agitation or aggression associated with Alzheimer's disease, optionally comprising administering a dose from about 1 mg to about 100 mg.

Functional Dyspepsia

Functional dyspepsia (FD) is one of the most common gastrointestinal disorders encountered in clinical practice. Several pathophysiological mechanisms have been proposed to underlie symptom generation in FD, including visceral hypersensitivity due to central or peripheral sensitization, low-grade inflammatory states, altered secretion of gastrointestinal hormones, genetic predisposition, and abnormal gastric emptying or accommodation. Gastric accommodation in healthy humans is inhibited by administration of the $CB_1$ receptor antagonist rimonabant (Ameloot, Aliment Pharmacol Ther, 2010, 31(10), 1123-31). In addition, research supports the hypothesis that the function of the endocannabinoid system is altered in FD patients; hence, it is inferred that MGLL inhibition, by elevating 2-AG, in turn activating the $CB_1$ receptor, will increase gastric accommodation and lessen symptoms of functional dyspepsia (Ly, Psychother Psychosom, 2015, 84(3), 149-58).

In some embodiments, disclosed herein is a method of treating functional dyspepsia, in a patient in need thereof, comprising administering to the patient in need thereof an effective dose of Compound 1, or a pharmaceutically acceptable salt thereof. In some embodiments is a method of treating functional dyspepsia, in a patient in need thereof, comprising administering to the patient in need thereof an effective dose of Compound 1, or a pharmaceutically acceptable salt thereof, wherein the effective dose is from about 1 mg to about 100 mg. Disclosed also herein is Compound 1, or a pharmaceutically acceptable salt thereof, for use in a method of treating functional dyspepsia, optionally comprising administering a dose from about 1 mg to about 100 mg.

Inflammatory Bowel Disease

Inflammatory bowel disease (IBD) involves chronic inflammation of all or part of the digestive tract. IBD primarily includes ulcerative colitis and Crohn's disease. Both usually involve severe diarrhea, pain, fatigue and weight loss. IBD can be debilitating and sometimes leads to life-threatening complications. MGLL inhibition was protective in a mouse model of IBD (Alhouayek, FASEB, 2011, 2711-2721).

In some embodiments, disclosed herein is a method of treating inflammatory bowel disease, in a patient in need thereof, comprising administering to the patient in need thereof an effective dose of Compound 1, or a pharmaceutically acceptable salt thereof. In some embodiments is a method of treating inflammatory bowel disease, in a patient in need thereof, comprising administering to the patient in need thereof an effective dose of Compound 1, or a pharmaceutically acceptable salt thereof, wherein the effective dose is from about 1 mg to about 100 mg. Disclosed also herein is Compound 1, or a pharmaceutically acceptable salt thereof, for use in a method of treating inflammatory bowel disease, optionally comprising administering a dose from about 1 mg to about 100 mg.

Skeletal Muscle Contusion

Skeletal muscle contusion indicates a direct, blunt, compressive force to a muscle. Contusions are one of the most common sports-related injuries. The severity of contusions ranges from simple skin contusions to muscle and bone contusions to internal organ contusions. MGLL inhibition demonstrated anti-inflammatory effects in a rat skeletal muscle contusion model (Jiang, European Journal of Pharmacology, 2015, online pub. dx.doi.org/10.1016).

In some embodiments, disclosed herein is a method of treating a skeletal muscle contusion, in a patient in need thereof, comprising administering to the patient in need thereof an effective dose of Compound 1, or a pharmaceutically acceptable salt thereof. In some embodiments is a method of treating a skeletal muscle contusion, in a patient in need thereof, comprising administering to the patient in need thereof an effective dose of Compound 1, or a pharmaceutically acceptable salt thereof, wherein the effective dose is from about 1 mg to about 100 mg. Disclosed also herein is Compound 1, or a pharmaceutically acceptable salt thereof, for use in a method of treating a skeletal muscle contusion of the human or animal body, optionally comprising administering a dose from about 1 mg to about 100 mg.

Additional Methods

Disclosed herein are methods of optimizing therapeutic efficacy for treatment of inflammation or neuropathic pain in a patient in need thereof, comprising (a) administering to the patient in need thereof a composition comprising Compound 1, or a pharmaceutically acceptable salt thereof; (b) measuring the concentration of plasma 2-AG in the patient; and (c) administering an increased or decreased amount of Compound 1 as indicated by the concentration of plasma 2-AG. Disclosed also herein is Compound 1 or a pharmaceutically acceptable salt thereof, for use in a method for optimizing therapeutic efficacy of a treatment of inflammation or neuropathic pain in a patient, said method comprising (a) administering to the patient in need thereof a composition comprising Compound 1, or a pharmaceutically acceptable salt thereof; (b) measuring the concentration of plasma 2-AG in the patient; and (c) administering an increased or decreased amount of Compound 1 as indicated by the concentration of plasma 2-AG.

Disclosed herein are methods of optimizing therapeutic efficacy for treatment of inflammation or neuropathic pain in a patient in need thereof, comprising (a) administering to the patient in need thereof a composition comprising Compound 1, or a pharmaceutically acceptable salt thereof; (b) measuring the percentage of MGLL covalently attached to a fragment of Compound 1 in PBMCs from the patient; and (c) administering an increased or decreased amount of Compound 1 as indicated by the percentage of MGLL covalently attached to a fragment of Compound 1 in plasma. Disclosed also herein is Compound 1 or a pharmaceutically acceptable salt thereof, for use in a method for optimizing therapeutic efficacy of a treatment of inflammation or neuropathic pain in a patient, said method comprising (a) administering to the patient in need thereof a composition comprising Compound 1, or a pharmaceutically acceptable salt thereof; (b) measuring the percentage of MGLL covalently attached to a fragment of Compound 1 in PBMCs from the patient; and (c) administering an increased or decreased amount of Compound 1 as indicated by the percentage of MGLL covalently attached to a fragment of Compound 1 in plasma.

Disclosed herein are methods of increasing the concentration of plasma 2-AG in a subject using an effective dose of Compound 1, or a pharmaceutically acceptable salt thereof, wherein the concentration of plasma 2-AG in a subject is increased by at least 2-fold. Disclosed also herein is Compound 1 or a pharmaceutically acceptable salt thereof, for use in a method of therapy of increasing the concentration of plasma 2-AG in a subject, by administering an effective dose of Compound 1 or a pharmaceutically acceptable salt thereof, wherein the concentration of plasma 2-AG in the subject is increased by at least 2-fold. In some embodiments, the concentration of plasma 2-AG in a subject is increased by at least 3-fold, at least 4-fold, at least 5-fold, at least 6-fold, at least 7-fold, at least 8-fold, at least 9-fold, or at least 10-fold. In some embodiments, the effective dose is from about 1 mg to about 500 mg of Compound 1, or a pharmaceutically acceptable salt thereof. In some embodiments, the effective dose is from about 2 mg to about 400 mg of Compound 1, or a pharmaceutically acceptable salt thereof. In some embodiments, the effective dose is about 10 mg to about 160 mg of Compound 1, or a pharmaceutically acceptable salt thereof. In some embodiments, the effective dose is about 2 mg to about 20 mg of Compound 1, or a pharmaceutically acceptable salt thereof. In some embodiments, the effective dose is administered orally.

Also disclosed herein are methods of binding MGLL with Compound 1 in PBMCs in a subject after administration of an effective dose of Compound 1, or a pharmaceutically acceptable salt thereof, to the subject, wherein a fragment of Compound 1 is covalently attached to at least 30% MGLL in PBMCs. Disclosed also herein is Compound 1 or a pharmaceutically acceptable salt thereof, for use in any one of the methods of therapy disclosed herein, wherein after administration in a subject of an effective dose of Compound 1, or a pharmaceutically acceptable salt thereof, a fragment of Compound 1 is covalently attached to at least 30% MGLL in PBMCs of the subject. In some embodiments, a fragment of Compound 1 is covalently attached to at least 40%, at least 50%, at least 60%, at least 70%, at least 80%, at least 90%, or at least 95%, MGLL in PBMCs. In some embodiments, the effective dose is from about 1 mg to about 500 mg of Compound 1, or a pharmaceutically acceptable salt thereof. In some embodiments, the effective dose is from about 2 mg to about 400 mg of Compound 1, or a pharmaceutically acceptable salt thereof. In some embodiments, the effective dose is about 10 mg to about 160 mg of Compound 1, or a pharmaceutically acceptable salt thereof. In some embodiments, the effective dose is about 2 mg to about 20 mg of Compound 1, or a pharmaceutically acceptable salt thereof. In some embodiments, the effective dose is administered orally.

Dosage and Plasma AUC

In some embodiments, an effective dose of Compound 1, or a pharmaceutically acceptable salt thereof, administered in the methods and medical uses disclosed herein is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg, including increments therein.

In some embodiments, an effective dose of Compound 1, or a pharmaceutically acceptable salt thereof, administered in the methods and medical uses disclosed herein is from about 1 mg to about 500 mg. In some embodiments, an effective dose of Compound 1, or a pharmaceutically acceptable salt thereof, administered in the methods and medical uses disclosed herein is from about 1 mg to about 450 mg. In some embodiments, an effective dose of Compound 1, or a pharmaceutically acceptable salt thereof, administered in the methods and medical uses disclosed herein is from about 1 mg to about 400 mg. In some embodiments, an effective dose of Compound 1, or a pharmaceutically acceptable salt thereof, administered in the methods and medical uses disclosed herein is from about 1 mg to about 350 mg. In some embodiments, an effective dose of Compound 1, or a pharmaceutically acceptable salt thereof, administered in the methods and medical uses disclosed herein is from about 1 mg to about 300 mg. In some embodiments, an effective dose of Compound 1, or a pharmaceutically acceptable salt thereof, administered in the methods and medical uses disclosed herein is from about 1 mg to about 250 mg. In some embodiments, an effective dose of Compound 1, or a pharmaceutically acceptable salt thereof, administered in the methods and medical uses disclosed herein is from about 1 mg to about 200 mg. In some embodiments, an effective dose of Compound 1, or a pharmaceutically acceptable salt thereof, administered in the methods and medical uses disclosed herein is from about 1 mg to about 150 mg. In some embodiments, an effective dose of Compound 1, or a pharmaceutically acceptable salt thereof, administered in the methods and medical uses disclosed herein is from about 1 mg to about 100 mg. In some embodiments, an effective dose of Compound 1, or a pharmaceutically acceptable salt thereof, administered in the methods and medical uses disclosed herein is from about 1 mg to about 50 mg. In some embodiments, an effective dose of Compound 1, or a pharmaceutically acceptable salt thereof, administered in the methods and medical uses disclosed herein is from about 1 mg to about 25 mg. In some embodiments, an effective dose of Compound 1, or a pharmaceutically acceptable salt thereof, administered in the methods and medical uses disclosed herein is from about 1 mg to about 15 mg. In some embodiments, an effective dose of Compound 1, or a pharmaceutically acceptable salt thereof, administered in the methods and medical uses disclosed herein is from about 2 mg to about 400 mg. In some embodiments, an effective dose of Compound 1, or a pharmaceutically acceptable salt thereof, administered in the methods and medical uses disclosed herein is from about 2 mg to about 350 mg. In some embodiments, an effective dose of Compound 1, or a pharmaceutically acceptable salt thereof, administered in the methods and medical uses disclosed herein is from about 2 mg to about 300 mg. In some embodiments, an effective dose of Compound 1, or a pharmaceutically acceptable salt thereof, administered in the methods and medical uses disclosed herein is from about 2 mg to about 250 mg. In some embodiments, an effective dose of Compound 1, or a pharmaceutically acceptable salt thereof, administered in the methods and medical uses disclosed herein is from about 2 mg to about 200 mg. In some embodiments, an effective dose of Compound 1, or a pharmaceutically acceptable salt thereof, administered in the methods and medical uses disclosed herein is from about 2 mg to about 150 mg. In some embodiments, an effective dose of Compound 1, or a pharmaceutically acceptable salt thereof, administered in the methods and medical uses disclosed herein is from about 2 mg to about 100 mg. In some embodiments, an effective dose of Compound 1, or a pharmaceutically acceptable salt thereof, administered in the methods and medical uses disclosed herein is from about 2 mg to about 50 mg. In some embodiments, an effective dose of Compound 1, or a pharmaceutically acceptable salt thereof, administered in the methods and medical uses disclosed herein is from about 2 mg to about 25 mg. In some embodiments, an effective dose of Compound 1, or a pharmaceutically acceptable salt thereof, administered in the methods and medical uses disclosed herein is from about 10 mg to about 300 mg. In some embodiments, an effective dose of Compound 1, or a pharmaceutically acceptable salt thereof, administered in the methods and medical uses disclosed herein is from about 10 mg to about 250 mg. In some embodiments, an effective dose of Compound 1, or a pharmaceutically acceptable salt thereof, administered in the methods and medical uses disclosed herein is from about 10 mg to about 200 mg. In some embodiments, an effective dose of Compound 1, or a pharmaceutically acceptable salt thereof, administered in the methods and medical uses disclosed herein is from about 10 mg to about 160 mg. In some embodiments, an effective dose of Compound 1, or a pharmaceutically acceptable salt thereof, administered in the methods and medical uses disclosed herein is from about 10 mg to about 100 mg. In some embodiments, an effective dose of Compound 1, or a pharmaceutically acceptable salt thereof, administered in the methods and medical uses disclosed herein is from about 10 mg to about 75 mg. In some embodiments, an effective dose of Compound 1, or a pharmaceutically acceptable salt thereof, administered in the methods and medical uses disclosed herein is from about 10 mg to about 50 mg. In some embodiments, an effective dose of Compound 1, or a pharmaceutically acceptable salt thereof, administered in the methods and medical uses disclosed herein is from about 10 mg to about 25 mg.

In some embodiments, an effective dose of Compound 1, or a pharmaceutically acceptable salt thereof, administered in the methods and medical uses disclosed herein is administered orally. In some embodiments, the effective dose is taken with food. In some embodiments, the effective dose is taken without food. In some embodiments, an effective dose of Compound 1, or a pharmaceutically acceptable salt thereof, administered in the methods and medical uses disclosed herein is administered once per day. In some embodiments, an effective dose of Compound 1, or a pharmaceutically acceptable salt thereof, administered in the methods and medical uses disclosed herein is administered twice per day. In some embodiments, an effective dose of Compound 1, or a pharmaceutically acceptable salt thereof, administered in the methods and medical uses disclosed herein is administered three times per day. In some embodiments, an effective dose of Compound 1, or a pharmaceutically acceptable salt thereof, administered in the methods and medical uses disclosed herein is administered four times per day. In some embodiments, an effective dose of Compound 1, or a pharmaceutically acceptable salt thereof, administered in the methods and medical uses disclosed herein is administered once every two days. In some embodiments, an effective dose of Compound 1, or a pharmaceutically acceptable salt thereof, administered in the methods and medical uses disclosed herein is administered once every three days. In some embodiments, an effective dose of Compound 1, or a pharmaceutically acceptable salt thereof, administered in the methods and medical uses disclosed herein is administered once every four days. In some embodiments, an effective dose of Compound 1, or a pharmaceutically acceptable salt thereof, administered in the methods and medical uses disclosed herein is administered once every five days. In some embodiments, an effective dose of Compound 1, or a pharmaceutically acceptable salt thereof, administered in the methods and medical uses disclosed herein is administered once every six days. In some embodiments, an effective dose of Compound 1, or a pharmaceutically acceptable salt thereof, administered in the methods and medical uses disclosed herein is administered once per week.

In some embodiments, a blood sample is collected from a subject after administration of Compound 1, or a pharmaceutically acceptable salt thereof. In some embodiments, the blood sample is analyzed for Compound 1 quantification.

In some embodiments, administration of Compound 1, or a pharmaceutically acceptable salt thereof, to a subject provides a plasma $AUC_{0\text{-}inf}$ of Compound 1 is at least 0.05 µM·hr. In some embodiments, administration of Compound 1, or a pharmaceutically acceptable salt thereof, to a subject provides a plasma $AUC_{0\text{-}inf}$ of Compound 1 is at least 0.01 µM·hr. In some embodiments, administration of Compound 1, or a pharmaceutically acceptable salt thereof, to a subject provides a plasma $AUC_{0\text{-}inf}$ of Compound 1 is at least 0.1 µM·hr. In some embodiments, administration of Compound 1, or a pharmaceutically acceptable salt thereof, to a subject provides a plasma $AUC_{0\text{-}inf}$ of Compound 1 is at least 0.2 µM·hr. In some embodiments, administration of Compound 1, or a pharmaceutically acceptable salt thereof, to a subject provides a plasma $AUC_{0\text{-}inf}$ of Compound 1 is at least 0.3 µM·hr. In some embodiments, administration of Compound 1, or a pharmaceutically acceptable salt thereof, to a subject provides a plasma $AUC_{0\text{-}inf}$ of Compound 1 is at least 0.4 µM·hr. In some embodiments, administration of Compound 1, or a pharmaceutically acceptable salt thereof, to a subject provides a plasma $AUC_{0\text{-}inf}$ of Compound 1 is at least 0.5 µM·hr. In some embodiments, administration of Compound 1, or a pharmaceutically acceptable salt thereof, to a subject provides a plasma $AUC_{0\text{-}inf}$ of Compound 1 is at least 0.6 µM·hr. In some embodiments, administration of Compound 1, or a pharmaceutically acceptable salt thereof, to a subject provides a plasma $AUC_{0\text{-}inf}$ of Compound 1 is at least 0.7 µM·hr. In some embodiments, administration of Compound 1, or a pharmaceutically acceptable salt thereof, to a subject provides a plasma $AUC_{0\text{-}inf}$ of Compound 1 is at least 0.8 µM·hr. In some embodiments, administration of Compound 1, or a pharmaceutically acceptable salt thereof, to a subject provides a plasma $AUC_{0\text{-}inf}$ of Compound 1 is at least 0.9 µM·hr. In some embodiments, administration of Compound 1, or a pharmaceutically acceptable salt thereof, to a subject provides a plasma $AUC_{0\text{-}inf}$ of Compound 1 is at least 1.0 µM·hr. In some embodiments, administration of Compound 1, or a pharmaceutically acceptable salt thereof, to a subject provides a plasma $AUC_{0\text{-}inf}$ of Compound 1 is at least 1.2 µM·hr. In some embodiments, administration of Compound 1, or a pharmaceutically acceptable salt thereof, to a subject provides a plasma $AUC_{0\text{-}inf}$ of Compound 1 is at least 1.4 µM·hr. In some embodiments, administration of Compound 1, or a pharmaceutically acceptable salt thereof, to a subject provides a plasma $AUC_{0\text{-}inf}$ of Compound 1 is at least 1.6 µM·hr. In some embodiments, administration of Compound 1, or a pharmaceutically acceptable salt thereof, to a subject provides a plasma $AUC_{0\text{-}inf}$ of Compound 1 is at least 1.8 µM·hr. In some embodiments, administration of Compound 1, or a pharmaceutically acceptable salt thereof, to a subject provides a plasma $AUC_{0\text{-}inf}$ of Compound 1 is at least 2.0 µM·hr. In some embodiments, administration of Compound 1, or a pharmaceutically acceptable salt thereof, to a subject provides a plasma $AUC_{0\text{-}inf}$ of Compound 1 is at least 2.2 µM·hr. In some embodiments, administration of Compound 1, or a pharmaceutically acceptable salt thereof, to a subject provides a plasma $AUC_{0\text{-}inf}$ of Compound 1 is at least 2.4 µM·hr. In some embodiments, administration of Compound 1, or a pharmaceutically acceptable salt thereof, to a subject provides a plasma $AUC_{0\text{-}inf}$ of Compound 1 is at least 2.6 µM·hr. In some embodiments, administration of Compound 1, or a pharmaceutically acceptable salt thereof, to a subject provides a plasma $AUC_{0\text{-}inf}$ of Compound 1 is at least 2.8 µM·hr. In some embodiments, administration of Compound 1, or a pharmaceutically acceptable salt thereof, to a subject provides a plasma $AUC_{0\text{-}inf}$ of Compound 1 is at least 3.0 µM·hr.

In some embodiments, administration of Compound 1, or a pharmaceutically acceptable salt thereof, to a subject provides a plasma AUC0-inf of Compound 1 is about 0.01 µM·hr to about 3.0 µM·hr. In some embodiments, administration of Compound 1, or a pharmaceutically acceptable salt thereof, to a subject provides a plasma AUC0-inf of Compound 1 is about 0.05 µM·hr to about 3.0 µM·hr. In some embodiments, administration of Compound 1, or a pharmaceutically acceptable salt thereof, to a subject provides a plasma AUC0-inf of Compound 1 is about 0.1 µM·hr to about 3.0 µM·hr. In some embodiments, administration of Compound 1, or a pharmaceutically acceptable salt thereof, to a subject provides a plasma AUC0-inf of Compound 1 is about 0.15 µM·hr to about 3.0 µM·hr. In some embodiments, administration of Compound 1, or a pharmaceutically acceptable salt thereof, to a subject provides a plasma AUC0-inf of Compound 1 is about 0.2 µM·hr to about 3.0 µM·hr. In some embodiments, administration of Compound 1, or a pharmaceutically acceptable salt thereof, to a subject provides a plasma AUC0-inf of Compound 1 is about 0.3 µM·hr to about 3.0 µM·hr. In some embodiments, administration of Compound 1, or a pharmaceutically acceptable salt thereof, to a subject provides a plasma $AUC_{0\text{-}inf}$ of Compound 1 is about 0.4 µM·hr to about 3.0 µM·hr. In some embodiments, administration of Compound 1, or a pharmaceutically acceptable salt thereof, to a subject provides a plasma $AUC_{0\text{-}inf}$ of Compound 1 is about 0.5 µM·hr to about 3.0 µM·hr. In some embodiments, administration of Compound 1, or a pharmaceutically acceptable salt thereof, to a subject provides a plasma $AUC_{0\text{-}inf}$ of Compound 1 is about 0.7 µM·hr to about 3.0 µM·hr. In some embodiments, administration of Compound 1, or a pharmaceutically acceptable salt thereof, to a subject provides a plasma $AUC_{0\text{-}inf}$ of Compound 1 is about 1.0 M·hr to about 3.0 µM·hr. In some embodiments, administration of Compound 1, or a pharmaceutically acceptable salt thereof, to a subject provides a plasma $AUC_{0\text{-}inf}$ of Compound 1 is about 0.01 µM·hr to about 2.5 µM·hr. In some embodiments, administration of Compound 1, or a pharmaceutically acceptable salt thereof, to a subject provides a plasma $AUC_{0\text{-}inf}$ of Compound 1 is about 0.05 µM·hr to about 2.5 µM·hr. In some embodiments, administration of Compound 1, or a pharmaceutically acceptable salt thereof, to a subject provides a plasma $AUC_{0\text{-}inf}$ of Compound 1 is about 0.1 µM·hr to about 2.5 µM·hr. In some embodiments, administration of Compound 1, or a pharmaceutically acceptable salt thereof, to a subject provides a plasma $AUC_{0\text{-}inf}$ of Compound 1 is about 0.15 µM·hr to about 2.5 µM·hr. In some embodiments, administration of Compound 1, or a pharmaceutically acceptable salt thereof, to a subject provides a plasma $AUC_{0\text{-}inf}$ of Compound 1 is about 0.2 µM·hr to about 2.5

µM·hr. In some embodiments, administration of Compound 1, or a pharmaceutically acceptable salt thereof, to a subject provides a plasma $AUC_{0-inf}$ of Compound 1 is about 0.3 µM·hr to about 2.5 µM·hr. In some embodiments, administration of Compound 1, or a pharmaceutically acceptable salt thereof, to a subject provides a plasma $AUC_{0-inf}$ of Compound 1 is about 0.4 µM·hr to about 2.5 µM·hr. In some embodiments, administration of Compound 1, or a pharmaceutically acceptable salt thereof, to a subject provides a plasma $AUC_{0-inf}$ of Compound 1 is about 0.5 µM·hr to about 2.5 µM·hr. In some embodiments, administration of Compound 1, or a pharmaceutically acceptable salt thereof, to a subject provides a plasma $AUC_{0-inf}$ of Compound 1 is about 0.7 µM·hr to about 2.5 µM·hr. In some embodiments, administration of Compound 1, or a pharmaceutically acceptable salt thereof, to a subject provides a plasma $AUC_{0-inf}$ of Compound 1 is about 1.0 µM·hr to about 2.5 µM·hr. In some embodiments, administration of Compound 1, or a pharmaceutically acceptable salt thereof, to a subject provides a plasma $AUC_{0-inf}$ of Compound 1 is about 0.01 µM·hr to about 2.0 µM·hr. In some embodiments, administration of Compound 1, or a pharmaceutically acceptable salt thereof, to a subject provides a plasma $AUC_{0-inf}$ of Compound 1 is about 0.05 µM·hr to about 2.0 µM·hr. In some embodiments, administration of Compound 1, or a pharmaceutically acceptable salt thereof, to a subject provides a plasma $AUC_{0-inf}$ of Compound 1 is about 0.1 µM·hr to about 2.0 µM·hr. In some embodiments, administration of Compound 1, or a pharmaceutically acceptable salt thereof, to a subject provides a plasma $AUC_{0-inf}$ of Compound 1 is about 0.15 µM·hr to about 2.0 µM·hr. In some embodiments, administration of Compound 1, or a pharmaceutically acceptable salt thereof, to a subject provides a plasma $AUC_{0-inf}$ of Compound 1 is about 0.2 µM·hr to about 2.0 µM·hr. In some embodiments, administration of Compound 1, or a pharmaceutically acceptable salt thereof, to a subject provides a plasma $AUC_{0-inf}$ of Compound 1 is about 0.3 µM·hr to about 2.0 µM·hr. In some embodiments, administration of Compound 1, or a pharmaceutically acceptable salt thereof, to a subject provides a plasma $AUC_{0-inf}$ of Compound 1 is about 0.4 µM·hr to about 2.0 µM·hr. In some embodiments, administration of Compound 1, or a pharmaceutically acceptable salt thereof, to a subject provides a plasma $AUC_{0-inf}$ of Compound 1 is about 0.5 µM·hr to about 2.0 µM·hr. In some embodiments, administration of Compound 1, or a pharmaceutically acceptable salt thereof, to a subject provides a plasma $AUC_{0-inf}$ of Compound 1 is about 0.7 µM·hr to about 2.0 µM·hr. In some embodiments, administration of Compound 1, or a pharmaceutically acceptable salt thereof, to a subject provides a plasma $AUC_{0-inf}$ of Compound 1 is about 1.0 µM·hr to about 2.0 µM·hr.

In some embodiments, administration of Compound 1, or a pharmaceutically acceptable salt thereof, to a subject provides a steady state plasma $AUC_{0-inf}$ of Compound 1 is at least 0.05 µM·hr. In some embodiments, administration of Compound 1, or a pharmaceutically acceptable salt thereof, to a subject provides a steady state plasma $AUC_{0-inf}$ of Compound 1 is at least 0.01 µM·hr. In some embodiments, administration of Compound 1, or a pharmaceutically acceptable salt thereof, to a subject provides a steady state plasma $AUC_{0-inf}$ of Compound 1 is at least 0.1 µM·hr. In some embodiments, administration of Compound 1, or a pharmaceutically acceptable salt thereof, to a subject provides a steady state plasma $AUC_{0-inf}$ of Compound 1 is at least 0.2 µM·hr. In some embodiments, administration of Compound 1, or a pharmaceutically acceptable salt thereof, to a subject provides a steady state plasma $AUC_{0-inf}$ of Compound 1 is at least 0.3 µM·hr. In some embodiments, administration of Compound 1, or a pharmaceutically acceptable salt thereof, to a subject provides a steady state plasma $AUC_{0-inf}$ of Compound 1 is at least 0.4 µM·hr. In some embodiments, administration of Compound 1, or a pharmaceutically acceptable salt thereof, to a subject provides a steady state plasma $AUC_{0-inf}$ of Compound 1 is at least 0.5 µM·hr. In some embodiments, administration of Compound 1, or a pharmaceutically acceptable salt thereof, to a subject provides a steady state plasma $AUC_{0-inf}$ of Compound 1 is at least 0.6 µM·hr. In some embodiments, administration of Compound 1, or a pharmaceutically acceptable salt thereof, to a subject provides a steady state plasma $AUC_{0-inf}$ of Compound 1 is at least 0.7 µM·hr. In some embodiments, administration of Compound 1, or a pharmaceutically acceptable salt thereof, to a subject provides a steady state plasma $AUC_{0-inf}$ of Compound 1 is at least 0.8 µM·hr. In some embodiments, administration of Compound 1, or a pharmaceutically acceptable salt thereof, to a subject provides a steady state plasma $AUC_{0-inf}$ of Compound 1 is at least 0.9 µM·hr. In some embodiments, administration of Compound 1, or a pharmaceutically acceptable salt thereof, to a subject provides a steady state plasma $AUC_{0-inf}$ of Compound 1 is at least 1.0 µM·hr. In some embodiments, administration of Compound 1, or a pharmaceutically acceptable salt thereof, to a subject provides a steady state plasma $AUC_{0-inf}$ of Compound 1 is at least 1.2 µM·hr. In some embodiments, administration of Compound 1, or a pharmaceutically acceptable salt thereof, to a subject provides a steady state plasma $AUC_{0-inf}$ of Compound 1 is at least 1.4 µM·hr. In some embodiments, administration of Compound 1, or a pharmaceutically acceptable salt thereof, to a subject provides a steady state plasma $AUC_{0-inf}$ of Compound 1 is at least 1.6 µM·hr. In some embodiments, administration of Compound 1, or a pharmaceutically acceptable salt thereof, to a subject provides a steady state plasma $AUC_{0-inf}$ of Compound 1 is at least 1.8 µM·hr. In some embodiments, administration of Compound 1, or a pharmaceutically acceptable salt thereof, to a subject provides a steady state plasma $AUC_{0-inf}$ of Compound 1 is at least 2.0 µM·hr. In some embodiments, administration of Compound 1, or a pharmaceutically acceptable salt thereof, to a subject provides a steady state plasma $AUC_{0-inf}$ of Compound 1 is at least 2.2 µM·hr. In some embodiments, administration of Compound 1, or a pharmaceutically acceptable salt thereof, to a subject provides a steady state plasma $AUC_{0-inf}$ of Compound 1 is at least 2.4 µM·hr. In some embodiments, administration of Compound 1, or a pharmaceutically acceptable salt thereof, to a subject provides a steady state plasma $AUC_{0-inf}$ of Compound 1 is at least 2.6 µM·hr. In some embodiments, administration of Compound 1, or a pharmaceutically acceptable salt thereof, to a subject provides a steady state plasma $AUC_{0-inf}$ of Compound 1 is at least 2.8 µM·hr. In some embodiments, administration of Compound 1, or a pharmaceutically acceptable salt thereof, to a subject provides a steady state plasma $AUC_{0-inf}$ of Compound 1 is at least 3.0 µM·hr.

In some embodiments, administration of Compound 1, or a pharmaceutically acceptable salt thereof, to a subject provides a steady state plasma $AUC_{0-inf}$ of Compound 1 is about 0.01 µM·hr to about 3.0 µM·hr. In some embodiments, administration of Compound 1, or a pharmaceutically acceptable salt thereof, to a subject provides a steady state plasma $AUC_{0-inf}$ of Compound 1 is about 0.05 µM·hr to about 3.0 µM·hr. In some embodiments, administration of Compound 1, or a pharmaceutically acceptable salt thereof, to a subject provides a steady state plasma $AUC_{0-inf}$ of Compound 1 is about 0.1 µM·hr to about 3.0 µM·hr. In some embodiments, administration of Compound 1, or a pharmaceutically acceptable salt thereof, to a subject provides a steady state plasma $AUC_{0-inf}$ of Compound 1 is about 0.15 µM·hr to about 3.0 µM·hr. In some embodiments, administration of Compound 1, or a pharmaceutically acceptable salt thereof, to a subject provides a steady state plasma $AUC_{0-inf}$ of Compound 1 is about 0.2 M·hr to about 3.0 µM·hr. In some embodiments, administration of Compound 1, or a pharmaceutically acceptable salt thereof, to a subject provides a steady state plasma $AUC_{0-inf}$ of Compound 1 is about 0.3 µM·hr to about 3.0 µM·hr. In some embodiments, administration of Compound 1, or a pharmaceutically acceptable salt thereof, to a subject provides a steady state plasma $AUC_{0-inf}$ of Compound 1 is about 0.4 µM·hr to about 3.0 µM·hr. In some embodiments, administration of Compound 1, or a pharmaceutically acceptable salt thereof, to a subject provides a steady state plasma $AUC_{0-inf}$ of Compound 1 is about 0.5 µM·hr to about 3.0 µM·hr. In some embodiments, administration of Compound 1, or a pharmaceutically acceptable salt thereof, to a subject provides a steady state plasma $AUC_{0-inf}$ of Compound 1 is about 0.7 M·hr to about 3.0 µM·hr. In some embodiments, administration of Compound 1, or a pharmaceutically acceptable salt thereof, to a subject provides a steady state plasma $AUC_{0-inf}$ of Compound 1 is about 1.0 µM·hr to about 3.0 µM·hr. In some embodiments, administration of Compound 1, or a pharmaceutically acceptable salt thereof, to a subject provides a steady state plasma $AUC_{0-inf}$ of Compound 1 is about 0.01 µM·hr to about 2.5 µM·hr. In some embodiments, administration of Compound 1, or a pharmaceutically acceptable salt thereof, to a subject provides a steady state plasma $AUC_{0-inf}$ of Compound 1 is about 0.05 µM·hr to about 2.5 µM·hr. In some embodiments, administration of Compound 1, or a pharmaceutically acceptable salt thereof, to a subject provides a steady state plasma $AUC_{0-inf}$ of Compound 1 is about 0.1 M·hr to about 2.5 µM·hr. In some embodiments, administration of Compound 1, or a pharmaceutically acceptable salt thereof, to a subject provides a steady state plasma $AUC_{0-inf}$ of Compound 1 is about 0.15 µM·hr to about 2.5 µM·hr. In some embodiments, administration of Compound 1, or a pharmaceutically acceptable salt thereof, to a subject provides a steady state plasma $AUC_{0-inf}$ of Compound 1 is about 0.2 µM·hr to about 2.5 µM·hr. In some embodiments, administration of Compound 1, or a pharmaceutically acceptable salt thereof, to a subject provides a steady state plasma $AUC_{0-inf}$ of Compound 1 is about 0.3 µM·hr to about 2.5 µM·hr. In some embodiments, administration of Compound 1, or a pharmaceutically acceptable salt thereof, to a subject provides a steady state plasma $AUC_{0-inf}$ of Compound 1 is about 0.4 M·hr to about 2.5 µM·hr. In some embodiments, administration of Compound 1, or a pharmaceutically acceptable salt thereof, to a subject provides a steady state plasma $AUC_{0-inf}$ of Compound 1 is about 0.5 µM·hr to about 2.5 µM·hr. In some embodiments, administration of Compound 1, or a pharmaceutically acceptable salt thereof, to a subject provides a steady state plasma $AUC_{0-inf}$ of Compound 1 is about 0.7 µM·hr to about 2.5 µM·hr. In some embodiments, administration of Compound 1, or a pharmaceutically acceptable salt thereof, to a subject provides a steady state plasma $AUC_{0-inf}$ of Compound 1 is about 1.0 µM·hr to about 2.5 µM·hr. In some embodiments, administration of Compound 1, or a pharmaceutically acceptable salt thereof, to a subject provides a steady state plasma $AUC_{0-inf}$ of Compound 1 is about 0.01 M·hr to about 2.0 µM·hr. In some embodiments, administration of Compound 1, or a pharmaceutically acceptable salt thereof, to a subject provides a steady state plasma $AUC_{0-inf}$ of Compound 1 is about 0.05 µM·hr to about 2.0 µM·hr. In some embodiments, administration of Compound 1, or a pharmaceutically acceptable salt thereof, to a subject provides a steady state plasma $AUC_{0-inf}$ of Compound 1 is about 0.1 µM·hr to about 2.0 µM·hr. In some embodiments, administration of Compound 1, or a pharmaceutically acceptable salt thereof, to a subject provides a steady state plasma $AUC_{0-inf}$ of Compound 1 is about 0.15 µM·hr to about 2.0 µM·hr. In some embodiments, administration of Compound 1, or a pharmaceutically acceptable salt thereof, to a subject provides a steady state plasma $AUC_{0-inf}$ of Compound 1 is about 0.2 M·hr to about 2.0 µM·hr. In some embodiments, administration of Compound 1, or a pharmaceutically acceptable salt thereof, to a subject provides a steady state plasma $AUC_{0-inf}$ of Compound 1 is about 0.3 µM·hr to about 2.0 µM·hr. In some embodiments, administration of Compound 1, or a pharmaceutically acceptable salt thereof, to a subject provides a steady state plasma $AUC_{0-inf}$ of Compound 1 is about 0.4 µM·hr to about 2.0 µM·hr. In some embodiments, administration of Compound 1, or a pharmaceutically acceptable salt thereof, to a subject provides a steady state plasma $AUC_{0-inf}$ of Compound 1 is about 0.5 µM·hr to about 2.0 µM·hr. In some embodiments, administration of Compound 1, or a pharmaceutically acceptable salt thereof, to a subject provides a steady state plasma $AUC_{0-inf}$ of Compound 1 is about 0.7 M·hr to about 2.0 µM·hr. In some embodiments, administration of Compound 1, or a pharmaceutically acceptable salt thereof, to a subject provides a steady state plasma $AUC_{0-inf}$ of Compound 1 is about 1.0 µM·hr to about 2.0 µM·hr.

In some embodiments, administration of Compound 1, or a pharmaceutically acceptable salt thereof, in the methods and medical uses disclosed herein produce in a human subject group an average plasma $AUC_{0-inf}$ of Compound 1 of at least 0.05 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of at least 0.01 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of at least 0.1 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of at least 0.2 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of at least 0.3 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of at least 0.4 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of at least 0.5 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 0.6 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 0.7 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 0.8 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 0.9 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 1.0 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 1.2 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 1.4 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 1.6 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 1.8 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 2.0 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 2.2 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 2.4 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 2.6 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 2.8 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of at least 3.0 µM·hr.

In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.01 µM·hr to about 3.0 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.05 µM·hr to about 3.0 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.1 µM·hr to about 3.0 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.15 µM·hr to about 3.0 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.2 µM·hr to about 3.0 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.3 µM·hr to about 3.0 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.4 µM·hr to about 3.0 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.5 µM·hr to about 3.0 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.7 µM·hr to about 3.0 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 1.0 µM·hr to about 3.0 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.01 µM·hr to about 2.5 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.05 µM·hr to about 2.5 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.1 µM·hr to about 2.5 µM·hr. In some embodiments, administration of Compound 1, or a pharmaceutically acceptable salt thereof, in the methods and medical uses disclosed herein produce in a human subject group an average plasma $AUC_{0\text{-}inf}$ of Compound 1 of about 0.15 µM·hr to about 2.5 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.2 µM·hr to about 2.5 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.3 µM·hr to about 2.5 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.4 µM·hr to about 2.5 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.5 µM·hr to about 2.5 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.7 µM·hr to about 2.5 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 1.0 µM·hr to about 2.5 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.01 µM·hr to about 2.0 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.05 µM·hr to about 2.0 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.1 µM·hr to about 2.0 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.15 µM·hr to about 2.0 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.2 µM·hr to about 2.0 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.3 µM·hr to about 2.0 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.4 µM·hr to about 2.0 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.5 µM·hr to about 2.0 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 0.7 µM·hr to about 2.0 µM·hr. In some embodiments, administration of Compound 1, or a pharmaceutically acceptable salt thereof, in the methods and medical uses disclosed herein produce in a human subject group an average plasma $AUC_{0-inf}$ of Compound 1 of about 1.0 µM·hr to about 2.0 µM·hr.

In some embodiments, administration of Compound 1, or a pharmaceutically acceptable salt thereof, in the methods and medical uses disclosed herein produce in a human subject group an average plasma $AUC_{0-inf}$ of about 0.01 µM·hr, 0.05 µM·hr, 0.1 µM·hr, 0.15 µM·hr, about 0.2 µM·hr, about 0.3 µM·hr, about 0.4 µM·hr, about 0.5 µM·hr, about 0.6 µM·hr, about 0.7 µM·hr, about 0.8 µM·hr, about 0.9 µM·hr, about 1.0 µM·hr, about 1.1 µM·hr, about 1.2 µM·hr, about 1.3 µM·hr, about 1.4 µM·hr, about 1.5 µM·hr, about 1.6 µM·hr, about 1.7 µM·hr, about 1.8 µM·hr, about 1.9 µM·hr, about 2.0 µM·hr, about 2.1 µM·hr, about 2.2 µM·hr, about 2.3 µM·hr, about 2.4 µM·hr, about 2.5 µM·hr, about 2.6 µM·hr, about 2.7 µM·hr, about 2.8 µM·hr, about 2.9 µM·hr, about 3.0 µM·hr, about 3.1 µM·hr, about 3.2 µM·hr, about 3.3 µM·hr, about 3.4 µM·hr, about 3.5 µM·hr, about 3.6 µM·hr, about 3.7 µM·hr, about 3.8 µM·hr, about 3.9 µM·hr, or about 4.0 µM·hr after administration of Compound 1 to the subject.

In some embodiments, urine is collected from a subject after administration of Compound 1, or a pharmaceutically acceptable salt thereof. In some embodiments, the urine is analyzed for urinary Compound 1 quantification and urinary excretion characterization. In further embodiments, the urine is analyzed for qualitative metabolite characterization.

In some embodiments, administration of Compound 1, or a pharmaceutically acceptable salt thereof, in the methods and medical uses disclosed herein produce little to no effect on mood state of the subject or patient. In some embodiments, pre- and post-dose fluctuations in mood of the subject or patient are assessed using the short-version (30 items) of the Profile of Mood States (POMS Brief Form). In some embodiments, POMS data is used to evaluate potential Compound 1 dose-related effects on mood.

In some embodiments, administration of Compound 1, or a pharmaceutically acceptable salt thereof, in the methods and medical uses disclosed herein produce little to no effect on cognitive function of the subject or patient. In some embodiments, effects on cognitive function are evaluated using a battery of standardized and validated computerized tests (Cogstate Battery). This battery includes the following tests: Groton Maze Learning Test (GMLT), Detection (DET), Identification (IDN), One Card Learning (OCL), and ONB (One Back) Tasks. In some embodiments, the subject or patient performs this battery pre-dose, and at the protocol-specified intervals post-dose in order to evaluate potential Compound 1 dose-related effects on cognition, problem solving/reasoning, processing speed, attention/vigilance and visual recognition memory.

In some embodiments, administration of Compound 1, or a pharmaceutically acceptable salt thereof, in the methods and medical uses disclosed herein produce mild to no effect on the patient's or subject's Cutaneous Thermal Thresholds (CTT).

Target Engagement

In some embodiments, plasma concentration of Compound 1 is measured from a sample of blood from the subject after administration of Compound 1, or a pharmaceutically acceptable salt thereof.

In some embodiments, the blood sample from the subject is evaluated for MGLL activity. In some embodiments, MGLL activity is evaluated by measurement of plasma 2-AG concentration. 2-AG is an endogenous MGLL substrate. Inhibition of MGLL in vivo in preclinical species is associated with increases in 2-AG concentrations (in the brain, as well as in the peripheral blood). In some embodiments, plasma 2-AG concentration is measured using an in vitro assay. In some embodiments, plasma 2-AG concentration is measured using a fit-for-purpose mass spectrometry assay. In some embodiments, plasma 2-AG concentrations are measured from the same blood samples that are collected for the evaluation of Compound 1 plasma concentrations.

Since plasma 2-AG concentrations in humans are known to undergo diurnal fluctuation [Hanlon et al., "Circadian rhythm of circulating levels of the endocannabinoid 2-arachidonoylglycerol", *J. Clin. Endocrinol. Metab.* 100: 220-226, (2015)], plasma 2-AG data from both recipients of the hydrochloride salt of Compound 1 and recipients of placebo are used to evaluate the dose-related effects of the hydrochloride salt of Compound 1. In some embodiments, average plasma 2-AG concentration in an untreated subject is about ~1.8 ng/mL (~4.8 nM). In some embodiments, plasma 2-AG concentrations in untreated subjects range from about 0.5 ng/mL to about 5 ng/mL.

In some embodiments, plasma 2-AG concentration in a subject increases at least 2-fold after administration to the subject of Compound 1, or a pharmaceutical acceptable salt thereof. In some embodiments, plasma 2-AG concentration in a subject increases at least 3-fold after administration to the subject of Compound 1, or a pharmaceutical acceptable salt thereof. In some embodiments, plasma 2-AG concentration in a subject increases at least 4-fold after administration to the subject of Compound 1, or a pharmaceutical acceptable salt thereof. In some embodiments, plasma 2-AG concentration in a subject increases at least 5-fold after administration to the subject of Compound 1, or a pharmaceutical acceptable salt thereof. In some embodiments, plasma 2-AG concentration in a subject increases at least 6-fold after administration to the subject of Compound 1, or a pharmaceutical acceptable salt thereof. In some embodiments, plasma 2-AG concentration in a subject increases at least 7-fold after administration to the subject of Compound 1, or a pharmaceutical acceptable salt thereof. In some embodiments, plasma 2-AG concentration in a subject increases at least 8-fold after administration to the subject of Compound 1, or a pharmaceutical acceptable salt thereof. In some embodiments, plasma 2-AG concentration in a subject increases at least 9-fold after administration to the subject of Compound 1, or a pharmaceutical acceptable salt thereof. In some embodiments, plasma 2-AG concentration in a subject increases at least 10-fold after administration to the subject of Compound 1, or a pharmaceutical acceptable salt thereof.

In some embodiments, plasma 2-AG concentration in a subject increases about 2-fold to about 10-fold after administration to the subject of Compound 1, or a pharmaceutical acceptable salt thereof. In some embodiments, plasma 2-AG concentration in a subject increases about 2-fold to about 3-fold after administration to the subject of Compound 1, or a pharmaceutical acceptable salt thereof. In some embodiments, plasma 2-AG concentration in a subject increases about 2-fold to about 4-fold after administration to the subject of Compound 1, or a pharmaceutical acceptable salt thereof. In some embodiments, plasma 2-AG concentration in a subject increases about 2-fold to about 5-fold after administration to the subject of Compound 1, or a pharmaceutical acceptable salt thereof. In some embodiments, plasma 2-AG concentration in a subject increases about 2-fold to about 6-fold after administration to the subject of Compound 1, or a pharmaceutical acceptable salt thereof. In some embodiments, plasma 2-AG concentration in a subject increases about 2-fold to about 7-fold after administration to the subject of Compound 1, or a pharmaceutical acceptable salt thereof. In some embodiments, plasma 2-AG concentration in a subject increases about 5-fold to about 7-fold after administration to the subject of Compound 1, or a pharmaceutical acceptable salt thereof. In some embodiments, plasma 2-AG concentration in a subject increases about 5-fold to about 10-fold after administration to the subject of Compound 1, or a pharmaceutical acceptable salt thereof.

In some embodiments, plasma 2-AG concentration in a subject is about 1 ng/mL to about 10 ng/mL after administration to the subject of Compound 1, or a pharmaceutical acceptable salt thereof. In some embodiments, plasma 2-AG concentration in a subject is about 1.5 ng/mL to about 15 ng/mL after administration to the subject of Compound 1, or a pharmaceutical acceptable salt thereof. In some embodiments, plasma 2-AG concentration in a subject is about 2.6 ng/mL to about 15 ng/mL after administration to the subject of Compound 1, or a pharmaceutical acceptable salt thereof. In some embodiments, plasma 2-AG concentration in a subject is about 3.0 ng/mL to about 18.0 ng/mL after administration to the subject of Compound 1, or a pharmaceutical acceptable salt thereof. In some embodiments, plasma 2-AG concentration in a subject is about 4.0 ng/mL to about 15 ng/mL after administration to the subject of Compound 1, or a pharmaceutical acceptable salt thereof. In some embodiments, plasma 2-AG concentration in a subject is about 5.0 ng/mL to about 15 ng/mL after administration to the subject of Compound 1, or a pharmaceutical acceptable salt thereof.

In some embodiments, plasma 2-AG concentration in a subject is at least 2.6 ng/mL after administration to the subject of Compound 1, or a pharmaceutical acceptable salt thereof. In some embodiments, plasma 2-AG concentration in a subject is at least about 5.4 ng/mL after administration to the subject of Compound 1, or a pharmaceutical acceptable salt thereof. In some embodiments, plasma 2-AG concentration in a subject is at least about 7.2 ng/mL after administration to the subject of Compound 1, or a pharmaceutical acceptable salt thereof. In some embodiments, plasma 2-AG concentration in a subject is at least about 9.0 ng/mL after administration to the subject of Compound 1, or a pharmaceutical acceptable salt thereof. In some embodiments, plasma 2-AG concentration in a subject is at least about 10.8 ng/mL after administration to the subject of Compound 1, or a pharmaceutical acceptable salt thereof. In some embodiments, plasma 2-AG concentration in a subject is at least about 12.6 ng/mL after administration to the subject of Compound 1, or a pharmaceutical acceptable salt thereof. In some embodiments, plasma 2-AG concentration in a subject is at least about 14.4 ng/mL after administration to the subject of Compound 1, or a pharmaceutical acceptable salt thereof. In some embodiments, plasma 2-AG concentration in a subject is at least about 16.2 ng/mL after administration to the subject of Compound 1, or a pharmaceutical acceptable salt thereof. In some embodiments, plasma 2-AG concentration in a subject is at least about 18.0 ng/mL after administration to the subject of Compound 1, or a pharmaceutical acceptable salt thereof.

In some embodiments, the residual plasma (i.e., after completion and unblinding of the study) is assayed for the presence of one or more other endogenous lipid mediators (e.g., other monoacylglycerol lipids and anandamide (AEA), the other major endogenous cannabinoid and primary substrate of FAAH).

In some embodiments, the blood sample from the subject is evaluated for peripheral blood mononuclear cell (PBMC) MGLL activity. Previous in vitro studies have demonstrated the presence of measurable MGLL activity in PBMCs prepared from healthy human donors. In some embodiments, the pharmacologic activity of exogenously added MGLL inhibitors in these PBMC preparations is readily quantified using activity-based protein profiling (ABPP) electrophoretic techniques, or by substrate-based assays. In some embodiments, MGLL target engagement in PBMCs is measured in PBMCs collected from subjects before, and at specified time intervals after administration of study drug using a fit-for-purpose substrate assay. In some embodiments, the dose- and exposure-related effects of Compound 1 on PBMC MGLL activity is evaluated. In some embodiments, a mass spectroscopy-based substrate assay is used to evaluate MGLL activity in PBMCs.

In some embodiments, a fragment of Compound 1 is covalently attached to at least 30% of MGLL in PBMCs from a subject after administration of Compound 1 to the subject. In some embodiments, a fragment of Compound 1 is covalently attached to at least 40% of MGLL in PBMCs from a subject after administration of Compound 1 to the subject. In some embodiments, a fragment of Compound 1 is covalently attached to at least 50% of MGLL in PBMCs from a subject after administration of Compound 1 to the subject. In some embodiments, a fragment of Compound 1 is covalently attached to at least 55% of MGLL in PBMCs from a subject after administration of Compound 1 to the subject. In some embodiments, a fragment of Compound 1 is covalently attached to at least 60% of MGLL in PBMCs from a subject after administration of Compound 1 to the subject. In some embodiments, a fragment of Compound 1 is covalently attached to at least 65% of MGLL in PBMCs from a subject after administration of Compound 1 to the subject. In some embodiments, a fragment of Compound 1 is covalently attached to at least 70% of MGLL in PBMCs from a subject after administration of Compound 1 to the subject. In some embodiments, a fragment of Compound 1 is covalently attached to at least 75% of MGLL in PBMCs from a subject after administration of Compound 1 to the subject. In some embodiments, a fragment of Compound 1 is covalently attached to at least 80% of MGLL in PBMCs from a subject after administration of Compound 1 to the subject. In some embodiments, a fragment of Compound 1 is covalently attached to at least 85% of MGLL in PBMCs from a subject after administration of Compound 1 to the subject. In some embodiments, a fragment of Compound 1 is covalently attached to at least 90% of MGLL in PBMCs from a subject after administration of Compound 1 to the subject. In some embodiments, a fragment of Compound 1 is covalently attached to at least 95% of MGLL in PBMCs from a subject after administration of Compound 1 to the subject. In some embodiments, measurement of fragments of Compound 1 covalently attached to MGLL in PBMCs in a subject is performed using an in vitro assay.

In some embodiments, the residual PBMC fractions (i.e., after completion and unblinding of the study) are also assayed for target engagement using ABPP techniques. The easy accessibility of PBMC in healthy volunteers facilitates the measurement of MGLL target engagement in the peripheral blood of healthy volunteers.

In some embodiments, a blood sample from a subject is also analyzed for one or more endogenous lipids other than or in addition to 2-AG. In further embodiments, the one or more endogenous lipids include, but are not limited to, anandamide and other monoacylglycerol species. In some embodiments, the one or more endogenous lipids is anandamide.

Pharmaceutical Compositions

Disclosed herein are pharmaceutical compositions for the treatment of inflammation or neuropathic pain, wherein each of the pharmaceutical compositions comprises an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Further disclosed herein are pharmaceutical compositions for the treatment of inflammation or neuropathic pain, wherein each of the pharmaceutical compositions comprises an effective dose of Compound 1, or a pharmaceutically acceptable salt thereof, and a pharmaceutically acceptable excipient, wherein the effective dose is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg, including increments therein.

Further disclosed herein are pharmaceutical compositions for the treatment of inflammation or neuropathic pain, wherein each of the pharmaceutical compositions comprises an effective dose of Compound 1, or a pharmaceutically acceptable salt thereof, and a pharmaceutically acceptable excipient, wherein the effective dose is from about 1 mg to about 500 mg. In some embodiments, an effective dose of Compound 1, or a pharmaceutically acceptable salt thereof, administered in the methods disclosed herein is from about 1 mg to about 450 mg. In some embodiments, an effective dose of Compound 1, or a pharmaceutically acceptable salt thereof, administered in the methods disclosed herein is from about 1 mg to about 400 mg. In some embodiments, an effective dose of Compound 1, or a pharmaceutically acceptable salt thereof, administered in the methods disclosed herein is from about 1 mg to about 350 mg. In some embodiments, an effective dose of Compound 1, or a pharmaceutically acceptable salt thereof, administered in the methods disclosed herein is from about 1 mg to about 300 mg. In some embodiments, an effective dose of Compound 1, or a pharmaceutically acceptable salt thereof, administered in the methods disclosed herein is from about 1 mg to about 250 mg. In some embodiments, an effective dose of Compound 1, or a pharmaceutically acceptable salt thereof, administered in the methods disclosed herein is from about 1 mg to about 200 mg. In some embodiments, an effective dose of Compound 1, or a pharmaceutically acceptable salt thereof, administered in the methods disclosed herein is from about 1 mg to about 150 mg. In some embodiments, an effective dose of Compound 1, or a pharmaceutically acceptable salt thereof, administered in the methods disclosed herein is from about 1 mg to about 100 mg. In some embodiments, an effective dose of Compound 1, or a pharmaceutically acceptable salt thereof, administered in the methods disclosed herein is from about 1 mg to about 50 mg. In some embodiments, an effective dose of Compound 1, or a pharmaceutically acceptable salt thereof, administered in the methods disclosed herein is from about 1 mg to about 25 mg. In some embodiments, an effective dose of Compound 1, or a pharmaceutically acceptable salt thereof, administered in the methods disclosed herein is from about 1 mg to about 15 mg. In some embodiments, an effective dose of Compound 1, or a pharmaceutically acceptable salt thereof, administered in the methods disclosed herein is from about 2 mg to about 400 mg. In some embodiments, an effective dose of Compound 1, or a pharmaceutically acceptable salt thereof, administered in the methods disclosed herein is from about 2 mg to about 350 mg. In some embodiments, an effective dose of Compound 1, or a pharmaceutically acceptable salt thereof, administered in the methods disclosed herein is from about 2 mg to about 300 mg. In some embodiments, an effective dose of Compound 1, or a pharmaceutically acceptable salt thereof, administered in the methods disclosed herein is from about 2 mg to about 250 mg. In some embodiments, an effective dose of Compound 1, or a pharmaceutically acceptable salt thereof, administered in the methods disclosed herein is from about 2 mg to about 200 mg. In some embodiments, an effective dose of Compound 1, or a pharmaceutically acceptable salt thereof, administered in the methods disclosed herein is from about 2 mg to about 150 mg. In some embodiments, an effective dose of Compound 1, or a pharmaceutically acceptable salt thereof, administered in the methods disclosed herein is from about 2 mg to about 100 mg. In some embodiments, an effective dose of Compound 1, or a pharmaceutically acceptable salt thereof, administered in the methods disclosed herein is from about 2 mg to about 50 mg. In some embodiments, an effective dose of Compound 1, or a pharmaceutically acceptable salt thereof, administered in the methods disclosed herein is from about 2 mg to about 25 mg. In some embodiments, an effective dose of Compound 1, or a pharmaceutically acceptable salt thereof, administered in the methods disclosed herein is from about 10 mg to about 300 mg. In some embodiments, an effective dose of Compound 1, or a pharmaceutically acceptable salt thereof, administered in the methods disclosed herein is from about 10 mg to about 250 mg. In some embodiments, an effective dose of Compound 1, or a pharmaceutically acceptable salt thereof, administered in the methods disclosed herein is from about 10 mg to about 200 mg. In some embodiments, an effective dose of Compound 1, or a pharmaceutically acceptable salt thereof, administered in the methods disclosed herein is from about 10 mg to about 160 mg. In some embodiments, an effective dose of Compound 1, or a pharmaceutically acceptable salt thereof, administered in the methods disclosed herein is from about 10 mg to about 100 mg. In some embodiments, an effective dose of Compound 1, or a pharmaceutically acceptable salt thereof, administered in the methods disclosed herein is from about 10 mg to about 75 mg. In some embodiments, an effective dose of Compound 1, or a pharmaceutically acceptable salt thereof, administered in the methods disclosed herein is from about 10 mg to about 50 mg. In some embodiments, an effective dose of Compound 1, or a pharmaceutically acceptable salt thereof, administered in the methods disclosed herein is from about 10 mg to about 25 mg.

Disclosed herein are pharmaceutical compositions for the treatment of neuropathic pain, wherein each of the pharmaceutical compositions comprise an effective dose of Compound 1, or a pharmaceutically acceptable salt thereof, and one or more pharmaceutically acceptable excipients, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Disclosed herein are pharmaceutical compositions for the treatment of neuropathic pain, wherein each of the pharmaceutical compositions comprise an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Further disclosed herein is a pharmaceutical composition for the treatment of neuropathic pain, wherein the pharmaceutical composition comprises an effective dose of Compound 1, or a pharmaceutically acceptable salt thereof, and a pharmaceutically acceptable excipient, wherein the effective dose is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg, including increments therein.

Further disclosed herein is a pharmaceutical composition for the treatment of neuropathic pain, wherein the pharmaceutical composition comprises an effective dose of Compound 1, or a pharmaceutically acceptable salt thereof, and a pharmaceutically acceptable excipient, wherein the effective dose is from about 1 mg to about 500 mg. In some embodiments, an effective dose of Compound 1, or a pharmaceutically acceptable salt thereof, administered in the methods disclosed herein is from about 1 mg to about 450 mg. In some embodiments, an effective dose of Compound 1, or a pharmaceutically acceptable salt thereof, administered in the methods disclosed herein is from about 1 mg to about 400 mg. In some embodiments, an effective dose of Compound 1, or a pharmaceutically acceptable salt thereof, administered in the methods disclosed herein is from about 1 mg to about 350 mg. In some embodiments, an effective dose of Compound 1, or a pharmaceutically acceptable salt thereof, administered in the methods disclosed herein is from about 1 mg to about 300 mg. In some embodiments, an effective dose of Compound 1, or a pharmaceutically acceptable salt thereof, administered in the methods disclosed herein is from about 1 mg to about 250 mg. In some embodiments, an effective dose of Compound 1, or a pharmaceutically acceptable salt thereof, administered in the methods disclosed herein is from about 1 mg to about 200 mg. In some embodiments, an effective dose of Compound 1, or a pharmaceutically acceptable salt thereof, administered in the methods disclosed herein is from about 1 mg to about 150 mg. In some embodiments, an effective dose of Compound 1, or a pharmaceutically acceptable salt thereof, administered in the methods disclosed herein is from about 1 mg to about 100 mg. In some embodiments, an effective dose of Compound 1, or a pharmaceutically acceptable salt thereof, administered in the methods disclosed herein is from about 1 mg to about 50 mg. In some embodiments, an effective dose of Compound 1, or a pharmaceutically acceptable salt thereof, administered in the methods disclosed herein is from about 1 mg to about 25 mg. In some embodiments, an effective dose of Compound 1, or a pharmaceutically acceptable salt thereof, administered in the methods disclosed herein is from about 1 mg to about 15 mg. In some embodiments, an effective dose of Compound 1, or a pharmaceutically acceptable salt thereof, administered in the methods disclosed herein is from about 2 mg to about 400 mg. In some embodiments, an effective dose of Compound 1, or a pharmaceutically acceptable salt thereof, administered in the methods disclosed herein is from about 2 mg to about 350 mg. In some embodiments, an effective dose of Compound 1, or a pharmaceutically acceptable salt thereof, administered in the methods disclosed herein is from about 2 mg to about 300 mg. In some embodiments, an effective dose of Compound 1, or a pharmaceutically acceptable salt thereof, administered in the methods disclosed herein is from about 2 mg to about 250 mg. In some embodiments, an effective dose of Compound 1, or a pharmaceutically acceptable salt thereof, administered in the methods disclosed herein is from about 2 mg to about 200 mg. In some embodiments, an effective dose of Compound 1, or a pharmaceutically acceptable salt thereof, administered in the methods disclosed herein is from about 2 mg to about 150 mg. In some embodiments, an effective dose of Compound 1, or a pharmaceutically acceptable salt thereof, administered in the methods disclosed herein is from about 2 mg to about 100 mg. In some embodiments, an effective dose of Compound 1, or a pharmaceutically acceptable salt thereof, administered in the methods disclosed herein is from about 2 mg to about 50 mg. In some embodiments, an effective dose of Compound 1, or a pharmaceutically acceptable salt thereof, administered in the methods disclosed herein is from about 2 mg to about 25 mg. In some embodiments, an effective dose of Compound 1, or a pharmaceutically acceptable salt thereof, administered in the methods disclosed herein is from about 10 mg to about 300 mg. In some embodiments, an effective dose of Compound 1, or a pharmaceutically acceptable salt thereof, administered in the methods disclosed herein is from about 10 mg to about 250 mg. In some embodiments, an effective dose of Compound 1, or a pharmaceutically acceptable salt thereof, administered in the methods disclosed herein is from about 10 mg to about 200 mg. In some embodiments, an effective dose of Compound 1, or a pharmaceutically acceptable salt thereof, administered in the methods disclosed herein is from about 10 mg to about 160 mg. In some embodiments, an effective dose of Compound 1, or a pharmaceutically acceptable salt thereof, administered in the methods disclosed herein is from about 10 mg to about 100 mg. In some embodiments, an effective dose of Compound 1, or a pharmaceutically acceptable salt thereof, administered in the methods disclosed herein is from about 10 mg to about 75 mg. In some embodiments, an effective dose of Compound 1, or a pharmaceutically acceptable salt thereof, administered in the methods disclosed herein is from about 10 mg to about 50 mg. In some embodiments, an effective dose of Compound 1, or a pharmaceutically acceptable salt thereof, administered in the methods disclosed herein is from about 10 mg to about 25 mg.

Disclosed herein are pharmaceutical compositions for the treatment of inflammation, wherein each of the pharmaceutical compositions comprise an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Further disclosed herein is a pharmaceutical composition for the treatment of inflammation, wherein the pharmaceutical composition comprises an effective dose of Compound 1, or a pharmaceutically acceptable salt thereof, and a pharmaceutically acceptable excipient, wherein the effective dose is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg, including increments therein.

Further disclosed herein is a pharmaceutical composition for the treatment of inflammation, wherein the pharmaceutical composition comprises an effective dose of Compound 1, or a pharmaceutically acceptable salt thereof, and a pharmaceutically acceptable excipient, wherein the effective dose is from about 1 mg to about 500 mg. In some embodiments, an effective dose of Compound 1, or a pharmaceutically acceptable salt thereof, administered in the methods disclosed herein is from about 1 mg to about 450 mg. In some embodiments, an effective dose of Compound 1, or a pharmaceutically acceptable salt thereof, administered in the methods disclosed herein is from about 1 mg to about 400 mg. In some embodiments, an effective dose of Compound 1, or a pharmaceutically acceptable salt thereof, administered in the methods disclosed herein is from about 1 mg to about 350 mg. In some embodiments, an effective dose of Compound 1, or a pharmaceutically acceptable salt thereof, administered in the methods disclosed herein is from about 1 mg to about 300 mg. In some embodiments, an effective dose of Compound 1, or a pharmaceutically acceptable salt thereof, administered in the methods disclosed herein is from about 1 mg to about 250 mg. In some embodiments, an effective dose of Compound 1, or a pharmaceutically acceptable salt thereof, administered in the methods disclosed herein is from about 1 mg to about 200 mg. In some embodiments, an effective dose of Compound 1, or a pharmaceutically acceptable salt thereof, administered in the methods disclosed herein is from about 1 mg to about 150 mg. In some embodiments, an effective dose of Compound 1, or a pharmaceutically acceptable salt thereof, administered in the methods disclosed herein is from about 1 mg to about 100 mg. In some embodiments, an effective dose of Compound 1, or a pharmaceutically acceptable salt thereof, administered in the methods disclosed herein is from about 1 mg to about 50 mg. In some embodiments, an effective dose of Compound 1, or a pharmaceutically acceptable salt thereof, administered in the methods disclosed herein is from about 1 mg to about 25 mg. In some embodiments, an effective dose of Compound 1, or a pharmaceutically acceptable salt thereof, administered in the methods disclosed herein is from about 1 mg to about 15 mg. In some embodiments, an effective dose of Compound 1, or a pharmaceutically acceptable salt thereof, administered in the methods disclosed herein is from about 2 mg to about 400 mg. In some embodiments, an effective dose of Compound 1, or a pharmaceutically acceptable salt thereof, administered in the methods disclosed herein is from about 2 mg to about 350 mg. In some embodiments, an effective dose of Compound 1, or a pharmaceutically acceptable salt thereof, administered in the methods disclosed herein is from about 2 mg to about 300 mg. In some embodiments, an effective dose of Compound 1, or a pharmaceutically acceptable salt thereof, administered in the methods disclosed herein is from about 2 mg to about 250 mg. In some embodiments, an effective dose of Compound 1, or a pharmaceutically acceptable salt thereof, administered in the methods disclosed herein is from about 2 mg to about 200 mg. In some embodiments, an effective dose of Compound 1, or a pharmaceutically acceptable salt thereof, administered in the methods disclosed herein is from about 2 mg to about 150 mg. In some embodiments, an effective dose of Compound 1, or a pharmaceutically acceptable salt thereof, administered in the methods disclosed herein is from about 2 mg to about 100 mg. In some embodiments, an effective dose of Compound 1, or a pharmaceutically acceptable salt thereof, administered in the methods disclosed herein is from about 2 mg to about 50 mg. In some embodiments, an effective dose of Compound 1, or a pharmaceutically acceptable salt thereof, administered in the methods disclosed herein is from about 2 mg to about 25 mg. In some embodiments, an effective dose of Compound 1, or a pharmaceutically acceptable salt thereof, administered in the methods disclosed herein is from about 10 mg to about 300 mg. In some embodiments, an effective dose of Compound 1, or a pharmaceutically acceptable salt thereof, administered in the methods disclosed herein is from about 10 mg to about 250 mg. In some embodiments, an effective dose of Compound 1, or a pharmaceutically acceptable salt thereof, administered in the methods disclosed herein is from about 10 mg to about 200 mg. In some embodiments, an effective dose of Compound 1, or a pharmaceutically acceptable salt thereof, administered in the methods disclosed herein is from about 10 mg to about 160 mg. In some embodiments, an effective dose of Compound 1, or a pharmaceutically acceptable salt thereof, administered in the methods disclosed herein is from about 10 mg to about 100 mg. In some embodiments, an effective dose of Compound 1, or a pharmaceutically acceptable salt thereof, administered in the methods disclosed herein is from about 10 mg to about 75 mg. In some embodiments, an effective dose of Compound 1, or a pharmaceutically acceptable salt thereof, administered in the methods disclosed herein is from about 10 mg to about 50 mg. In some embodiments, an effective dose of Compound 1, or a pharmaceutically acceptable salt thereof, administered in the methods disclosed herein is from about 10 mg to about 25 mg.

Disclosed herein are pharmaceutical compositions for the treatment of inflammation or neuropathic pain, wherein each of the pharmaceutical compositions consist essentially of an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Disclosed herein are pharmaceutical compositions for the treatment of neuropathic pain, wherein each of the pharmaceutical compositions consist essentially of an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Disclosed herein are pharmaceutical compositions for the treatment of inflammation, wherein each of the pharmaceutical compositions consist essentially of an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Disclosed herein are pharmaceutical compositions for the treatment of Epilepsy/Seizure Disorder, Multiple Sclerosis, Neuromyelitis Optica (NMO), Tourette Syndrome, Alzheimer Disease, or abdominal pain associated with Irritable Bowel Syndrome, wherein each of the pharmaceutical compositions comprises an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Disclosed herein are pharmaceutical compositions for the treatment of Epilepsy/Seizure Disorder, Multiple Sclerosis, Neuromyelitis Optica (NMO), Tourette Syndrome, Alzheimer Disease, or abdominal pain associated with Irritable Bowel Syndrome, wherein each of the pharmaceutical compositions comprise an effective dose of Compound 1, or a pharmaceutically acceptable salt thereof, and one or more pharmaceutically acceptable excipients, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Further disclosed herein is a pharmaceutical composition for the treatment of Epilepsy/Seizure Disorder, Multiple Sclerosis, Neuromyelitis Optica (NMO), Tourette Syndrome, Alzheimer Disease, or abdominal pain associated with Irritable Bowel Syndrome, wherein the pharmaceutical composition comprises an effective dose of Compound 1, or a pharmaceutically acceptable salt thereof, and a pharmaceutically acceptable excipient, wherein the effective dose is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg, including increments therein.

Further disclosed herein is a pharmaceutical composition for the treatment of Epilepsy/Seizure Disorder, Multiple Sclerosis, Neuromyelitis Optica (NMO), Tourette Syndrome, Alzheimer Disease, or abdominal pain associated with Irritable Bowel Syndrome, wherein the pharmaceutical composition comprises an effective dose of Compound 1, or a pharmaceutically acceptable salt thereof, and a pharmaceutically acceptable excipient, wherein the effective dose is from about 1 mg to about 500 mg. In some embodiments, an effective dose of Compound 1, or a pharmaceutically acceptable salt thereof, administered in the methods disclosed herein is from about 1 mg to about 450 mg. In some embodiments, an effective dose of Compound 1, or a pharmaceutically acceptable salt thereof, administered in the methods disclosed herein is from about 1 mg to about 400 mg. In some embodiments, an effective dose of Compound 1, or a pharmaceutically acceptable salt thereof, administered in the methods disclosed herein is from about 1 mg to about 350 mg. In some embodiments, an effective dose of Compound 1, or a pharmaceutically acceptable salt thereof, administered in the methods disclosed herein is from about 1 mg to about 300 mg. In some embodiments, an effective dose of Compound 1, or a pharmaceutically acceptable salt thereof, administered in the methods disclosed herein is from about 1 mg to about 250 mg. In some embodiments, an effective dose of Compound 1, or a pharmaceutically acceptable salt thereof, administered in the methods disclosed herein is from about 1 mg to about 200 mg. In some embodiments, an effective dose of Compound 1, or a pharmaceutically acceptable salt thereof, administered in the methods disclosed herein is from about 1 mg to about 150 mg. In some embodiments, an effective dose of Compound 1, or a pharmaceutically acceptable salt thereof, administered in the methods disclosed herein is from about 1 mg to about 100 mg. In some embodiments, an effective dose of Compound 1, or a pharmaceutically acceptable salt thereof, administered in the methods disclosed herein is from about 1 mg to about 50 mg. In some embodiments, an effective dose of Compound 1, or a pharmaceutically acceptable salt thereof, administered in the methods disclosed herein is from about 1 mg to about 25 mg. In some embodiments, an effective dose of Compound 1, or a pharmaceutically acceptable salt thereof, administered in the methods disclosed herein is from about 1 mg to about 15 mg. In some embodiments, an effective dose of Compound 1, or a pharmaceutically acceptable salt thereof, administered in the methods disclosed herein is from about 2 mg to about 400 mg. In some embodiments, an effective dose of Compound 1, or a pharmaceutically acceptable salt thereof, administered in the methods disclosed herein is from about 2 mg to about 350 mg. In some embodiments, an effective dose of Compound 1, or a pharmaceutically acceptable salt thereof, administered in the methods disclosed herein is from about 2 mg to about 300 mg. In some embodiments, an effective dose of Compound 1, or a pharmaceutically acceptable salt thereof, administered in the methods disclosed herein is from about 2 mg to about 250 mg. In some embodiments, an effective dose of Compound 1, or a pharmaceutically acceptable salt thereof, administered in the methods disclosed herein is from about 2 mg to about 200 mg. In some embodiments, an effective dose of Compound 1, or a pharmaceutically acceptable salt thereof, administered in the methods disclosed herein is from about 2 mg to about 150 mg. In some embodiments, an effective dose of Compound 1, or a pharmaceutically acceptable salt thereof, administered in the methods disclosed herein is from about 2 mg to about 100 mg. In some embodiments, an effective dose of Compound 1, or a pharmaceutically acceptable salt thereof, administered in the methods disclosed herein is from about 2 mg to about 50 mg. In some embodiments, an effective dose of Compound 1, or a pharmaceutically acceptable salt thereof, administered in the methods disclosed herein is from about 2 mg to about 25 mg. In some embodiments, an effective dose of Compound 1, or a pharmaceutically acceptable salt thereof, administered in the methods disclosed herein is from about 10 mg to about 300 mg. In some embodiments, an effective dose of Compound 1, or a pharmaceutically acceptable salt thereof, administered in the methods disclosed herein is from about 10 mg to about 250 mg. In some embodiments, an effective dose of Compound 1, or a pharmaceutically acceptable salt thereof, administered in the methods disclosed herein is from about 10 mg to about 200 mg. In some embodiments, an effective dose of Compound 1, or a pharmaceutically acceptable salt thereof, administered in the methods disclosed herein is from about 10 mg to about 160 mg. In some embodiments, an effective dose of Compound 1, or a pharmaceutically acceptable salt thereof, administered in the methods disclosed herein is from about 10 mg to about 100 mg. In some embodiments, an effective dose of Compound 1, or a pharmaceutically acceptable salt thereof, administered in the methods disclosed herein is from about 10 mg to about 75 mg. In some embodiments, an effective dose of Compound 1, or a pharmaceutically acceptable salt thereof, administered in the methods disclosed herein is from about 10 mg to about 50 mg. In some embodiments, an effective dose of Compound 1, or a pharmaceutically acceptable salt thereof, administered in the methods disclosed herein is from about 10 mg to about 25 mg.

Disclosed herein are pharmaceutical compositions for the treatment of Epilepsy/Seizure Disorder, Multiple Sclerosis, Neuromyelitis Optica (NMO), Tourette Syndrome, Alzheimer Disease, or abdominal pain associated with Irritable Bowel Syndrome, wherein each of the pharmaceutical compositions consist essentially of an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Disclosed herein are pharmaceutical compositions for the treatment of acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia, wherein each of the pharmaceutical compositions comprises an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Disclosed herein are pharmaceutical compositions for the treatment of acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia, wherein each of the pharmaceutical compositions comprise an effective dose of Compound 1, or a pharmaceutically acceptable salt thereof, and one or more pharmaceutically acceptable excipients, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

Further disclosed herein is a pharmaceutical composition for the treatment of acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia, wherein the pharmaceutical composition comprises an effective dose of Compound 1, or a pharmaceutically acceptable salt thereof, and a pharmaceutically acceptable excipient, wherein the effective dose is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg, including increments therein.

Further disclosed herein is a pharmaceutical composition for the treatment of acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia, wherein the pharmaceutical composition comprises an effective dose of Compound 1, or a pharmaceutically acceptable salt thereof, and a pharmaceutically acceptable excipient, wherein the effective dose is from about 1 mg to about 500 mg. In some embodiments, an effective dose of Compound 1, or a pharmaceutically acceptable salt thereof, administered in the methods disclosed herein is from about 1 mg to about 450 mg. In some embodiments, an effective dose of Compound 1, or a pharmaceutically acceptable salt thereof, administered in the methods disclosed herein is from about 1 mg to about 400 mg. In some embodiments, an effective dose of Compound 1, or a pharmaceutically acceptable salt thereof, administered in the methods disclosed herein is from about 1 mg to about 350 mg. In some embodiments, an effective dose of Compound 1, or a pharmaceutically acceptable salt thereof, administered in the methods disclosed herein is from about 1 mg to about 300 mg. In some embodiments, an effective dose of Compound 1, or a pharmaceutically acceptable salt thereof, administered in the methods disclosed herein is from about 1 mg to about 250 mg. In some embodiments, an effective dose of Compound 1, or a pharmaceutically acceptable salt thereof, administered in the methods disclosed herein is from about 1 mg to about 200 mg. In some embodiments, an effective dose of Compound 1, or a pharmaceutically acceptable salt thereof, administered in the methods disclosed herein is from about 1 mg to about 150 mg. In some embodiments, an effective dose of Compound 1, or a pharmaceutically acceptable salt thereof, administered in the methods disclosed herein is from about 1 mg to about 100 mg. In some embodiments, an effective dose of Compound 1, or a pharmaceutically acceptable salt thereof, administered in the methods disclosed herein is from about 1 mg to about 50 mg. In some embodiments, an effective dose of Compound 1, or a pharmaceutically acceptable salt thereof, administered in the methods disclosed herein is from about 1 mg to about 25 mg. In some embodiments, an effective dose of Compound 1, or a pharmaceutically acceptable salt thereof, administered in the methods disclosed herein is from about 1 mg to about 15 mg. In some embodiments, an effective dose of Compound 1, or a pharmaceutically acceptable salt thereof, administered in the methods disclosed herein is from about 2 mg to about 400 mg. In some embodiments, an effective dose of Compound 1, or a pharmaceutically acceptable salt thereof, administered in the methods disclosed herein is from about 2 mg to about 350 mg. In some embodiments, an effective dose of Compound 1, or a pharmaceutically acceptable salt thereof, administered in the methods disclosed herein is from about 2 mg to about 300 mg. In some embodiments, an effective dose of Compound 1, or a pharmaceutically acceptable salt thereof, administered in the methods disclosed herein is from about 2 mg to about 250 mg. In some embodiments, an effective dose of Compound 1, or a pharmaceutically acceptable salt thereof, administered in the methods disclosed herein is from about 2 mg to about 200 mg. In some embodiments, an effective dose of Compound 1, or a pharmaceutically acceptable salt thereof, administered in the methods disclosed herein is from about 2 mg to about 150 mg. In some embodiments, an effective dose of Compound 1, or a pharmaceutically acceptable salt thereof, administered in the methods disclosed herein is from about 2 mg to about 100 mg. In some embodiments, an effective dose of Compound 1, or a pharmaceutically acceptable salt thereof, administered in the methods disclosed herein is from about 2 mg to about 50 mg. In some embodiments, an effective dose of Compound 1, or a pharmaceutically acceptable salt thereof, administered in the methods disclosed herein is from about 2 mg to about 25 mg. In some embodiments, an effective dose of Compound 1, or a pharmaceutically acceptable salt thereof, administered in the methods disclosed herein is from about 10 mg to about 300 mg. In some embodiments, an effective dose of Compound 1, or a pharmaceutically acceptable salt thereof, administered in the methods disclosed herein is from about 10 mg to about 250 mg. In some embodiments, an effective dose of Compound 1, or a pharmaceutically acceptable salt thereof, administered in the methods disclosed herein is from about 10 mg to about 200 mg. In some embodiments, an effective dose of Compound 1, or a pharmaceutically acceptable salt thereof, administered in the methods disclosed herein is from about 10 mg to about 160 mg. In some embodiments, an effective dose of Compound 1, or a pharmaceutically acceptable salt thereof, administered in the methods disclosed herein is from about 10 mg to about 100 mg. In some embodiments, an effective dose of Compound 1, or a pharmaceutically acceptable salt thereof, administered in the methods disclosed herein is from about 10 mg to about 75 mg. In some embodiments, an effective dose of Compound 1, or a pharmaceutically acceptable salt thereof, administered in the methods disclosed herein is from about 10 mg to about 50 mg. In some embodiments, an effective dose of Compound 1, or a pharmaceutically acceptable salt thereof, administered in the methods disclosed herein is from about 10 mg to about 25 mg.

Disclosed herein are pharmaceutical compositions for the treatment of acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia, wherein each of the pharmaceutical compositions consist essentially of an effective dose of Compound 1, or a pharmaceutically acceptable salt thereof, and a pharmaceutically acceptable excipient, wherein the effective dose is from about 1 mg to about 500 mg. In some embodiments, the effective dose is from about 2 mg to about 400 mg. In some embodiments, the effective dose is from about 10 mg to about 160 mg. In some embodiments, the effective dose is from about 2 mg to about 100 mg. In some embodiments, the effective dose is from about 2 mg to about 50 mg. In some embodiments, the effective dose is from about 2 mg to about 20 mg.

The following examples are provided merely as illustrative of various embodiments and shall not be construed to limit the invention in any way.

EXAMPLES

Example 1. In Vitro Pharmacology

Compound 1 was a potent inhibitor of human, mouse, rat, and dog MGLL with an $IC_{50}$<30 nM in all species. In vitro potency was determined using activity-based protein profiling (ABPP) which is a functional proteomic technology that uses chemical probes to covalently modify enzyme active sites in an activity-dependent manner (e.g., only catalytically active enzymes will react and become labeled with the ABPP probe). Identification of the proteins that were labeled by the probes was accomplished using polyacrylamide gel electrophoresis or mass spectrometry. In vitro treatment of tissue or cell homogenates with Compound 1 followed by incubation with probe, gel electrophoresis, and fluorescence imaging, allowed for the direct visualization and quantitation of the targets of Compound 1.

The inhibitory potency of Compound 1 towards MGLL in mouse, rat, dog, and human brain tissue and in lysates prepared from 2 human cell lines (PC3 prostate cancer cells and human embryo kidney [HEK]293T cells expressing recombinant hMGLL) was calculated as the $IC_{50}$ following a 30-minute pre-incubation. The $IC_{50}$ values are summarized in Table 1. MGLL migrates as multiple molecular weight species of approximately 34 kDa by gel electrophoresis. Compound 1 displays equivalent inhibitory potency against all MGLL isoforms.

TABLE 1

In vitro potency of Compound 1 against MGLL in mouse, rat, dog, and human tissue and cell homogenates determined by ABPP

| Species | Source | MGLL $IC_{50}$ (µM) |
|---|---|---|
| Mouse | Brain* | 0.027 ± 0.003 |
| Rat | Prefrontal Cortex† | 0.026 ± 0.006 |
| Dog | Prefrontal Cortex† | 0.012 ± 0.002 |
| Human | PC3 Cells† | 0.014 ± 0.005 |
|  | Prefrontal Cortex† | 0.021 ± 0.004 |
|  | Recombinant‡ | 0.008 ± 0.005 |

Abbreviations:
ABPP = activity-based protein profiling is a functional proteomic technology that uses chemical probes that react with mechanistically related classes of enzymes;
$IC_{50}$ = concentration producing 50% inhibition;
MGLL = monoacylglycerol lipase.
Additional information: Compound 1 (0-10 µM) was pre-incubated with the listed source material for 30 min at 37° C. prior to ABPP analysis. Data represent mean ± standard error of the mean (SEM) from several independent experiments: *n = 10, †n = 3, ‡n = 2.

The activity of Compound 1 was also assessed in human brain tissue using a mass spectrometry (MS)-based 2-AG substrate assay. In homogenates prepared from a human brain cortex sample, Compound 1 inhibited 94% of the conversion of 2-AG into AA with an $IC_{50}$ of 1.7 nM. Cellular potency was evaluated by gel-based ABPP in intact human PC3 prostate cancer cells where Compound 1 inhibited MGLL activity with an $IC_{50}$ of 2.2 nM.

Example 2. In Vivo Pharmacology

A. Relationship Among MGLL Target Engagement, 2-AG Concentrations, and Compound 1 Concentrations Occupancy and inhibition of protein active sites by small molecules is referred to as target engagement (i.e., a proximal marker of or how robustly a drug interacts with the target). Target engagement of MGLL by Compound 1 was measured using PET in non-human primates and ABPP in rodents and dogs. MGLL target engagement inhibits the hydrolysis of 2-AG, elevating tissue 2-AG concentrations, which can be measured in rodent tissues and fluids by MS. Elevation of 2-AG results in enhanced cannabinoid receptor signaling and physiological responses. The objective of these studies was to measure MGLL target engagement, 2-AG concentrations, and Compound 1 concentrations following Compound 1 administration in animals.

MGLL target engagement in the brain of rhesus monkeys was evaluated using a labeled form of a MGLL inhibitor. In rhesus monkeys, this labeled MGLL inhibitor demonstrated brain penetrance and regional distribution consistent with the known expression of MGLL in $CB_1$-containing neurons. MGLL occupancy by Compound 1 in the rhesus brain was evaluated using a blockade protocol comparing the labeled MGLL inhibitor binding at baseline and again following administration of Compound 1. Single-dose IV administration of Compound 1 (0.01-1 mg/kg, 90 min prior to PET tracer, 2 animals) engaged MGLL in the rhesus brain with an $ED_{50}$ of 0.047±0.025 mg/kg (see FIG. 1).

An oral-equivalent $ED_{50}$ dose for target engagement (but not for efficacy) was calculated from single-dose intravenous administration using a fraction absorbed factor of 0.2 (20% bioavailability).

ABPP analysis of tissues and cells from rodents treated with Compound 1 allowed direct visualization and quantitation of MGLL inhibition in vivo. Single-dose oral gavage (PO) administration of Compound 1 (up to 30 mg/kg, 4 hours, n=3-10, 4 independent experiments) to rats inhibited MGLL activity in the brain with an average $ED_{50}$ of 0.6 mg/kg. Dose-dependent inhibition of MGLL activity was also observed in rat liver ($ED_{50}$ of 0.1 mg/kg), heart ($ED_{50}$ of 0.08 mg/kg), and PBMC ($ED_{50}$ of 0.1 mg/kg).

Inhibition of MGLL causes accumulation of 2-AG in the rodent brain and periphery. Rat forebrain 2-AG concentrations increased ≥10-fold over control levels following single oral doses of Compound 1 (up to 30 mg/kg, 4 hours, n=3-10, 3 independent experiments) and were inversely related to brain MGLL activity. Brain 2-AG concentrations increased with an average $ED_{50}$ value of 1.3 mg/kg. The reduced potency for 2-AG accumulation ($ED_{50}$ of 1.3 mg/kg) versus MGLL inhibition ($ED_{50}$ value of 0.6 mg/kg) reflects the observation that inhibition of MGLL activity by approximately 50% is required before 2-AG accumulation is observed. Rat brain levels of the endocannabinoid anandamide were not elevated by Compound 1, suggesting that Compound 1 at these concentrations does not inhibit FAAH the primary anandamide hydrolase. Concentration of 2-AG in rat plasma and liver increased by 7-fold and approximately 3- to 5-fold, respectively, following single oral doses of Compound 1. Brain, liver, and blood Compound 1 concentrations increased with increasing doses of Compound 1 and were positively associated with MGLL inhibition and 2-AG concentrations.

Compound 1 caused similar dose-dependent effects on MGLL activity, 2-AG concentrations, and Compound 1 concentrations in mice. Single-dose PO administration of Compound 1 (2-32 mg/kg, 4 hours, n=3) inhibited MGLL activity in the mouse brain and liver with $ED_{50}$ values of 1.4 mg/kg and 0.5 mg/kg, respectively. Mouse brain 2-AG concentrations increased up to 30-fold following Compound 1 treatment.

Using fixed exponent allometric scaling, the projected human oral $ED_{50}$-equivalent dose based on the rat and monkey $ED_{50}$ data, ranges from 4.4 to 8.6 mg.

Figure 2A:
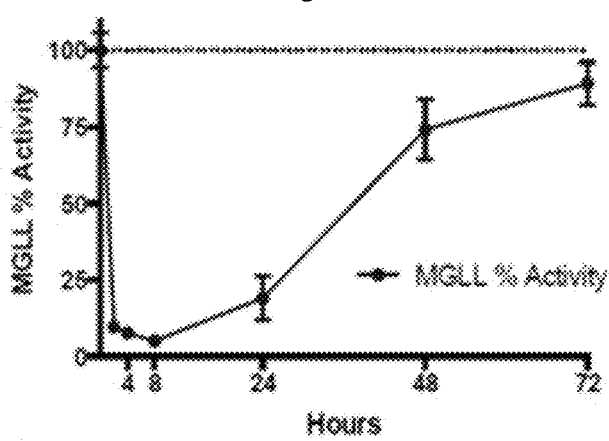
FIG. 2A shows the time course effects following a single dose of Compound 1 in rats on MGLL activity.
Figure 2B:
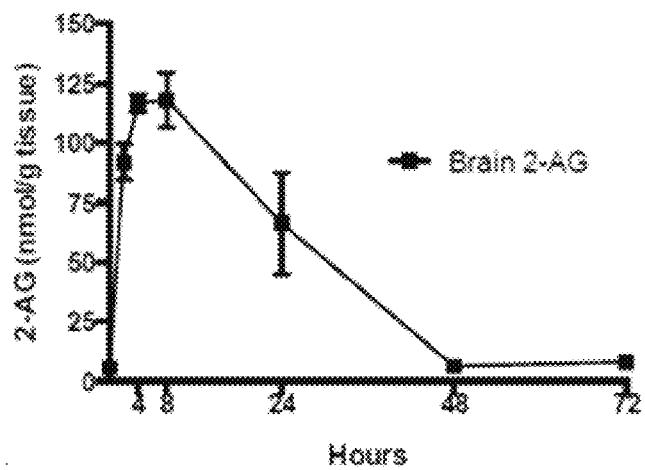
FIG. 2B shows the time course effects following a single dose of Compound 1 in rats on brain 2-AG concentrations.
Figure 2C:
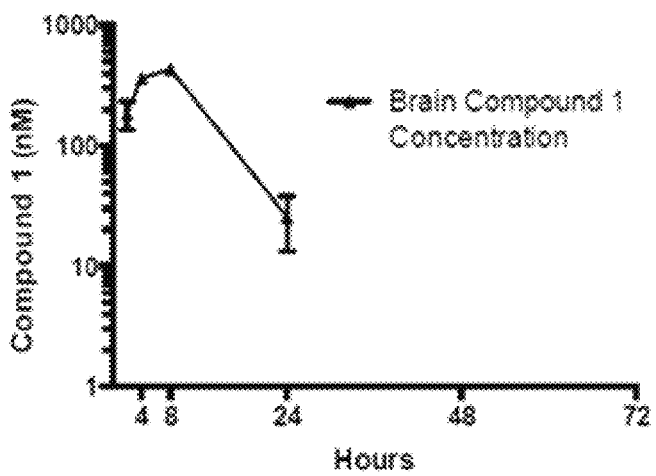
FIG. 2C shows the time course effects following a single dose of Compound 1 in rats on Compound 1 concentrations in the brain.

B. Time Course of Compound 1 Concentrations, MGLL Inhibition, and 2-AG Concentrations and Recovery of MGLL Activity Time-course effects of a single dose of Compound 1 (0.5-10 mg/kg, up to 144 hour postdose, n=3, 3 independent experiments) were evaluated in rats. In the rat brain, Compound 1 displayed time-dependent effects on MGLL activity. Compound concentrations of Compound 1 were positively correlated with inhibition of MGLL activity and levels of 2-AG (see FIG. 2A-C). Near-maximal MGLL inhibition and 2-AG accumulation was observed 4 hours after dosing, supporting the use of a 4-hour timepoint for behavioral studies.

Figure 2D:
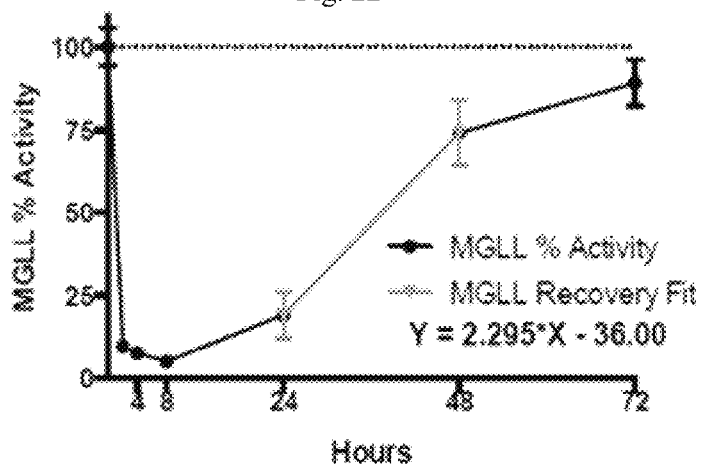
FIG. 2D shows the time course effects following a single dose of Compound 1 in rats on MGLL activity recovered at an average rate of approximately 2%/h after Compound 1 concentrations fell below detection.

After elimination of Compound 1 from the rat brain (i.e., to levels below the limit of quantitation [BLQ]), MGLL activity recovered at an average rate of approximately 2% per hour (see FIG. 2D). The recovery rate of MGLL activity in the rat brain is similar to that observed following covalent MGLL inhibition in other rat tissues and in cultured human cells. Once MGLL activity in the rat brain recovered to approximately 50% of pre-treatment activity, brain 2-AG concentrations returned to basal levels (see FIG. 2B).

Similar time-dependent effects on brain MGLL activity, 2-AG concentrations, and Compound 1 concentrations were observed following single dose Compound 1 in mice.

C. Efficacy in Rodent Models of Pain

The rat formalin paw test was used as the primary preclinical model to assess the PK/PD relationship for Compound 1 and inform human dose prediction. The formalin paw test is a model of pain induced by local injection of formalin into the hind paw producing an early response due to direct stimulation of nociceptors and a delayed response driven by inflammation and central sensitization. In studies performed with Compound 1, nociception was tracked by scoring the duration and frequency of paw licking using an automated system.

Figure 3A:
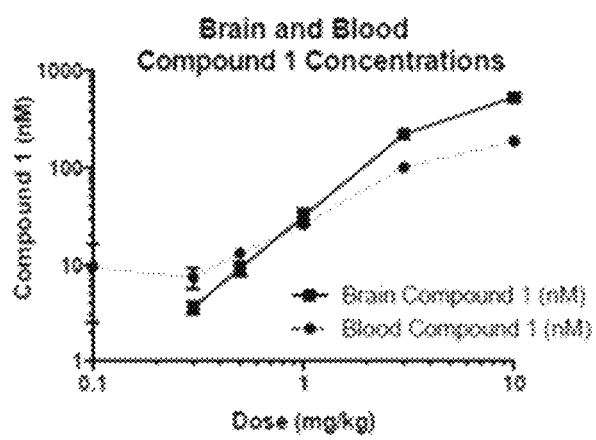
FIG. 3A shows Compound 1 concentrations in brain and blood following single-dose Compound 1 administration (0.1-10 mg/kg, PO, 4-4.75 hours, n=10)
Figure 3B:
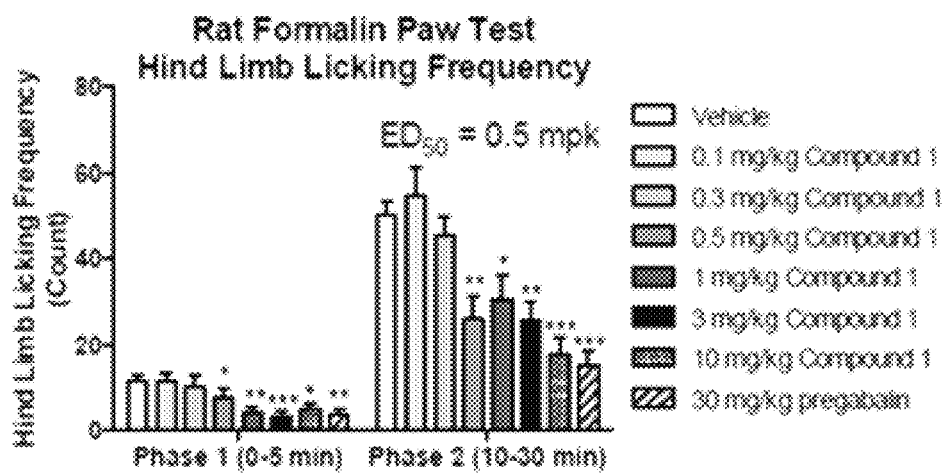
FIG. 3B shows nociceptive paw licking behavior following single-dose Compound 1 administration (0.1-10 mg/kg, PO, 4-4.75 hours, n=10).
Figure 3C:
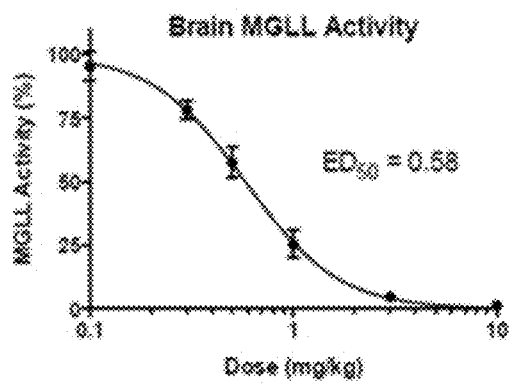
FIG. 3C shows brain MGLL activity following single-dose Compound 1 administration (0.1-10 mg/kg, PO, 4-4.75 hours, n=10).
Figure 3D:
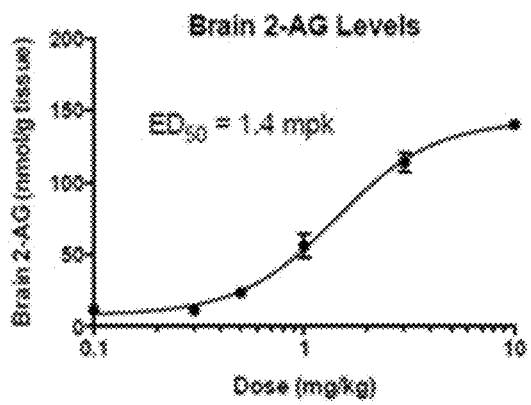
FIG. 3D shows brain 2-AG concentrations following single-dose Compound 1 administration (0.1-10 mg/kg, PO, 4-4.75 hours, n=10).

Single-dose administration of Compound 1 (up to 10 mg/kg, PO, 4 hours pre-test, n=10, 2 independent experiments) caused dose-dependent antinociceptive effects in formalin-challenged rats and reduced paw licking behavior in both the early (Phase 1) and delayed (Phase 2) phases (see FIG. 3B). The Phase 2 $ED_{50}$ of 0.5 mg/kg was used to assess the PK/PD relationship. Similar antinociceptive responses were observed with a single dose of the alpha-2, delta-1 calcium channel blocker pregabalin (30 mg/kg, PO, n=10), which is a clinically effective analgesic agent used for the treatment of neuropathic pain. The PK/PD relationship for Compound 1 in the rat formalin model is depicted in FIG. 3A-D, along with brain MGLL activity and 2-AG concentrations. This relationship demonstrates that Compound 1 achieves efficacy in the rat formalin test at doses that partially inhibit MGLL in the brain and cause sub-maximal increases in brain 2-AG concentrations. The $ED_{50}$ of 0.5 mg/kg in Phase 2 of the rat formalin test corresponds to brain Compound 1 concentrations of 5 nM, blood Compound 1 concentrations of 7 nM, approximately 40% inhibition of brain MGLL activity, and approximately 3-fold elevations in brain 2-AG concentrations.

The effects of multiple-dose administration of Compound 1 (0.5-10 mg/kg, 5 days QD, n=10) in the rat formalin model were investigated in a single study. Single and repeated administration of Compound 1 at a dose that partially inhibited MGLL (1 mg/kg) numerically reduced pain behaviors to a similar extent, though effects in the repeat dose group were not statistically different from vehicle.

The $ED_{50}$ for Compound 1 exposure associated with efficacy in the rat formalin nocifensive model was 0.4 μM·hr. Single oral $ED_{50}$ doses for efficacy (nocifensive paw licking behavior) and target engagement (by ex vivo activity-based protein profiling) were of similar magnitude. The $ED_{50}$ dose for nocifensive efficacy was also a minimally-efficacious dose. At the $ED_{50}$ dose in rats, and at oral doses 20-fold higher (the highest dose of Compound 1 evaluated in the formalin challenge model), overt behavioral or locomotor perturbations apart from the observed anti-nocifensive behaviors were not apparent. Rat brain 2-AG concentrations became measurably elevated only once MGLL activity is inhibited by greater than approximately 40-50%.

Example 3. Determination of MGLL Inhibition in Rat PBMCs and Plasma 2-AG Levels with Compound 1

Figure 4A:
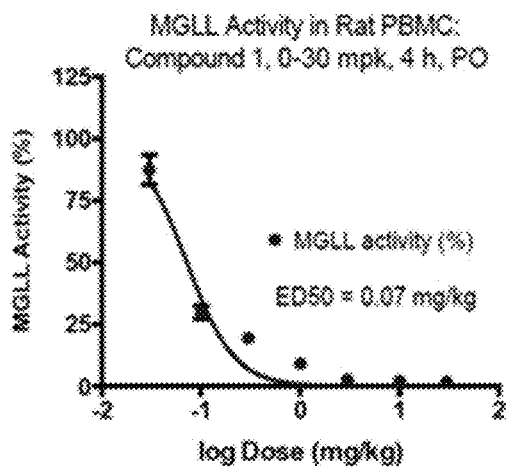
FIG. 4A shows inhibition of MGLL activity in rat PBMC following single-dose administration of Compound 1 (0.03-30 mg/kg, PO, 4 h, n=3 rats per dose).
Figure 4B:
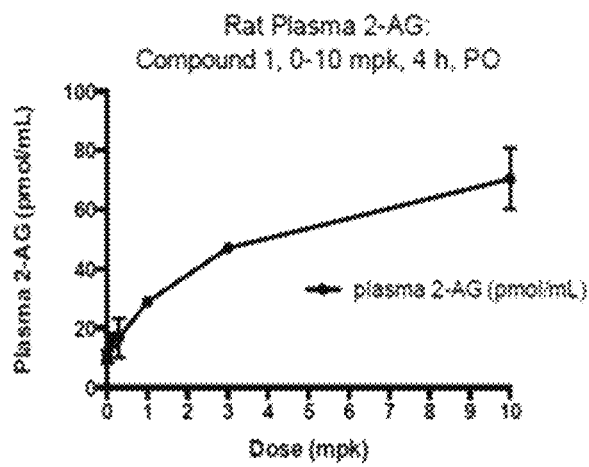
FIG. 4B elevation of rat plasma 2-AG concentrations following single-dose administration of Compound 1 (0.1-10 mg/kg, PO, 4 h, n=2 rats per dose).

Rats were administered single PO doses of Compound 1 (up to 30 mg/kg, 4 h, n=2-3). MGLL activity in rat PBMCs decreased dose-dependently with a median effective dose ($ED_{50}$) of 0.07 mg/kg and plasma 2-AG levels increased by up to 7-fold (see FIG. 4A-B). MGLL activity was assessed by ABPP analysis in PBMC lysates and plasma 2-AG concentrations were measured by liquid chromatography tandem mass spectrometry (LC-MS/MS).

Example 4. Determination of MGLL Inhibition in Human PBMCs with Compound 1

Figure 5A:
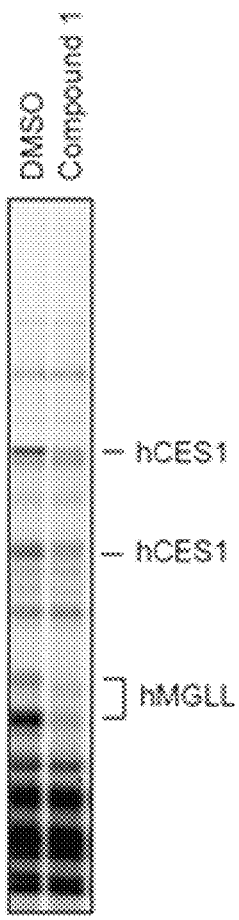
FIG. 5A shows inhibition of MGLL activity in human PBMC by Compound 1 (10 µM, 30 min, 37° C.) wherein MGLL activity was observed in human PBMC by activity-based protein profiling (ABPP) with the fluorophosphonate-rhodamine activity probe.
Figure 5B:
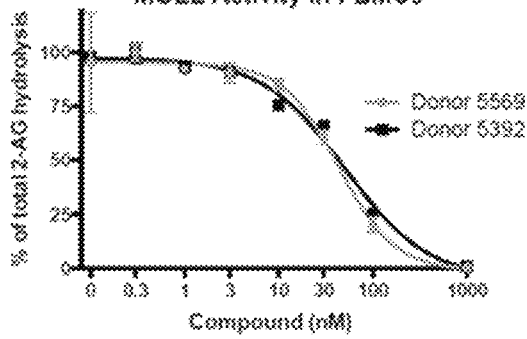
FIG. 5B shows inhibition of MGLL activity in human PBMC by Compound 1, wherein MGLL activity was measured by 2-AG hydrolysis in PBMC lysates isolated from human whole blood from two human donors 5569 and 5392 treated with Compound 1 (0.3-1000 nM, 30 min, 37° C., n=2 replicates per concentration per donor).

MGLL activity in human PBMCs can be readily assessed by ABPP analysis (see FIG. 5A) or by a mass spectrometry-based 2-AG substrate assay that measures the formation of AA product (see FIG. 5B). Incubation of Compound 1 (0.0003-1000 nM, 30 min, 37° C.) in human whole blood obtained from two healthy human donors inhibits MGLL activity in isolated PBMCs with an $IC_{50}$ of 47 nM (see FIG. 5B).

Example 5. Capsule Formulation

The hydrochloride salt of Compound 1 is formulated as powder-filled, gelatin capsules containing 2.14, 10.72, and 53.60 mg of hydrochloride salt which are equivalent to 2, 10, and 50 mg of Compound 1, respectively (salt factor=1.07). The gelatin capsule shells used are size 2 and the color of both cap and body is Swedish Orange.

The excipients used in the capsule formulation are: microcrystalline cellulose, croscarmellose sodium, magnesium stearate (vegetable origin), and gelatin capsule shells. The capsule shells are comprised of gelatin, red iron oxide, and titanium dioxide. All excipients meet EP/USP/NF specifications.

Matched placebo capsules (placebo for Compound 1 hydrochloride capsules) contain the same excipients. In the placebo formulation, the hydrochloride of Compound 1 is replaced with microcrystalline cellulose.

Stability studies have indicated that such Compound 1 hydrochloride capsules are stable for up to 2 months at 40° C./75% relative humidity accelerated storage conditions. Further stability studies have indicated that such Compound 1 hydrochloride capsules are stable for up to 6 months at 40° C./75% relative humidity accelerated storage conditions. Stability studies in the bulk container (30 ct/45 cc bottle) at long-term and accelerated storage conditions are run concurrently with a Phase I trial.

Stability studies of the matched placebo capsules at long-term and accelerated storage conditions are also run concurrently with a Phase I trial.

Example 6. A Single- and Multiple-Dose Study to Evaluate the Safety, Tolerability, Pharmacokinetics and Pharmacodynamics of the Hydrochloride Salt of Compound 1

General Design and Methodology: The purpose of this study is to assess the initial safety, tolerability, pharmacokinetics, and pharmacodynamics of Compound 1 (administered as Capsules of the hydrochloride salt of Compound 1) in healthy adults. In Part 1 of the study, individual subjects are administered single oral doses of the hydrochloride salt of Compound 1 (or matching placebo) in up to 4 treatment periods. In Part 2 of the study, individual subjects are administered daily oral doses of the hydrochloride salt of Compound 1 (or matching placebo) for up to 14 days. Data from this study is used to select doses and dose regimens for subsequent clinical studies.

This is a randomized, double-blind, placebo-controlled study to investigate the safety, tolerability, pharmacokinetics (PK) and pharmacodynamics (PD) of ascending single oral doses (Part 1, Panels A and B) and of ascending multiple daily oral doses (Part 2, Panels C-G) of the hydrochloride salt of Compound 1 in healthy adult subjects.

In Part 1, Panels A and B consist each of eight healthy male adult subjects (randomized to receive single ascending doses of either the hydrochloride salt of Compound 1 or matching placebo in a 3:1 ratio, respectively) in up to 4 treatment periods (Periods 1 to 4), conducted in an alternating fashion. The effect of a high-fat breakfast on the pharmacokinetics of the hydrochloride salt of Compound 1 is assessed in Panel A.

In Part 2, Panels C through G consist each of eight healthy adult subjects (randomized to receive either the hydrochloride salt of Compound 1 or matching placebo in a 3:1 ratio, respectively) once a day for up to 14 days. In Part 2, Panels are dosed sequentially.

Since this is a Phase 1 assessment of the hydrochloride salt of Compound 1 in humans, and given that pharmacokinetic, pharmacodynamic and safety profiles of the compound are still being evaluated, this protocol is written with some flexibility to accommodate the inherent dynamic nature of Phase 1 clinical trials.

Objectives:

Part I, Primary objective: To evaluate the safety and tolerability of Compound 1 after administration of single ascending oral doses of the hydrochloride salt of Compound 1 to healthy male adult subjects.

Part 1, Secondary objective: (1) To obtain preliminary plasma pharmacokinetics (e.g., $C_{max}$, $T_{max}$, $AUC_{0-t}$, $AUC_{0-inf}$, $t_{1/2}$) of the hydrochloride salt of Compound 1 following administration of single ascending oral doses to healthy male adult subjects. Hypothesis: At one or more well-tolerated single oral dose(s) of the hydrochloride salt of Compound 1, the geometric mean $AUC_{0-inf}$ of Compound 1 is at least 0.4 µM·hr. (2) To compare the effects of a high-fat breakfast on the plasma pharmacokinetics of the hydrochloride salt of Compound 1 following administration of single ascending oral doses to healthy male adult subjects to those in the fasted state. Estimation: The effect of a standardized high-fat breakfast on the plasma pharmacokinetics (e.g., $C_{max}$, $T_{max}$, $AUC_{0-inf}$) of the hydrochloride salt of Compound 1 after oral administration of a single dose of the hydrochloride salt of Compound 1 to healthy male adult subjects are estimated. (3) To obtain preliminary data on urinary excretion of intact drug following administration of single ascending oral doses of the hydrochloride salt of Compound 1 to healthy male adult subjects.

Part 2, Primary Objective: To evaluate the safety and tolerability of the hydrochloride salt of Compound 1 administered as multiple daily oral doses for up to 14 consecutive days to healthy adult subjects.

Part 2, Secondary Objective: (1) To assess the single-dose and steady-state time-plasma concentration profile, and pharmacokinetic parameter values (e.g., $C_{max}$, $T_{max}$, $AUC_{0-24h}$, $AUC_{0-tau}$, $t_{1/2}$, accumulation ratio) of the hydrochloride salt of Compound 1 following administration of multiple daily oral doses of the hydrochloride salt of Compound 1 for up to 14 consecutive days to healthy adult subjects. Hypothesis: At one or more well-tolerated daily oral dose(s) of the hydrochloride salt of Compound 1, the steady-state geometric mean $AUC_{0-24h}$ of Compound 1 is at least 0.4 µM·hr. (2) (If measured) To obtain preliminary data on urinary excretion of intact drug following administration of multiple daily oral doses of the hydrochloride salt of Compound 1 to healthy adult subjects.

Number of Subjects (Planned):

Part 1: Sixteen healthy adult male subjects between the ages of 18 and 55 years are enrolled in Part 1 of the study. Eight different subjects (randomized to receive hydrochloride salt of Compound 1 or matching placebo) participate in each panel of the study (Panels A and B).

Part 2: Up to forty healthy adult subjects (males, or females of non-childbearing potential) between the ages of 18 and 55 years are enrolled in Part 2 of the study. Eight different subjects (randomized to receive hydrochloride salt of Compound 1 or matching placebo) participate in each panel of the study (Panels C through G).

Criteria for Inclusion:

A) Subject understands the study procedures and agrees to participate in the study by giving written informed consent.

B) Part 1: Subject is male, 18 to 55 years of age at the pre-study/screening visit.

C) Part 2: Subject is male, or female (not of reproductive potential) 18 to 55 years of age at the pre-study/screening visit; further:

(1) If subject is a postmenopausal female: subject is without menses for at least 1 year and has a documented follicle stimulating hormone (FSH) level in the postmenopausal range at pretrial (screening).

(2) If subject is a surgically sterile female: subject is status post hysterectomy, bilateral oophorectomy, or tubal ligation. (Hysterectomy may be confirmed by ultrasound or other imaging technique if documentation is not available. Oophorectomy and tubal ligation must be confirmed by documentation).

D) Subject has a Body Mass Index (BMI)>18 to ≤30 kg/m² at the pre-study/screening visit. BMI=weight (kg)/height (m)² (BMI calculation should be rounded to the nearest whole number).

E) Subject is judged to be in good health based on medical history, physical examination, and vital sign measurements, and laboratory safety tests obtained at pre-study/screening, and within 24 hours prior to first administration of study drug.

F) Subject has no clinically significant abnormality of electrocardiography (ECG) performed at pre-study/screening, and prior to first administration of study drug.

G) Subject is a nonsmoker and/or has not used nicotine or nicotine-containing products (e.g., nicotine patch) for at least approximately 3 months.

H) Subject is willing to comply with the study restrictions.

I) Part 1: Subject is willing to eat the protocol-specified high-fat breakfast.

Criteria for Exclusion:

A) Subject is under the age of legal consent.

B) Subject has a personal history of a clinically significant psychiatric disorder (including severe affective disorder, psychotic tendencies and drug-induced psychoses). Subjects who have had situational depression or anxiety in the past may be enrolled at the discretion of the investigator.

C) Subject has a first-degree family history of schizophrenia, major affective disorder, or other psychosis.

D) Subject is mentally or legally incapacitated, has significant emotional problems at the time of pre-study/screening visit or is expected to have potential for mental incapacitation during the conduct of the study.

E) Subject has a history of any illness that, in the opinion of the study investigator, might confound the results of the study or pose an additional risk to the subject by virtue of their participation in the study.

F) Subject has an estimated creatinine clearance (CrCl) of ≤80 mL/min based on the Cockcroft-Gault equation. An actual creatinine clearance, as measured using a 24-hour urine collection, may be used in place of, or in conjunction with the Cockcraft-Gault calculation. Subjects with an actual or calculated creatinine clearance that is in the range of 72-79 mL/min (i.e., within 10% of 80 mL/min) may be enrolled in the study at the discretion of the investigator. Cockcraft-Gault Equation:

$$CrCl=(140-age\ [yr])*(body\ weight\ [kg])/(72)serum\ creatinine\ [mg/dL])$$

Note: For female subjects, multiply by 0.85 to obtain creatinine clearance.

G) Subject has a history of stroke, chronic seizures, or major neurological disorder.

H) Subject has a history of clinically significant endocrine, gastrointestinal, cardiovascular, peripheral vascular, hematological, hepatic, immunological, renal, respiratory, or genitourinary abnormalities or diseases. Subjects with a history of uncomplicated kidney stones (defined as spontaneous passage and no recurrence in the last 5 years), or childhood asthma may be enrolled in the trial at the discretion of the investigator.

I) Subject has a history of clinically significant neoplastic disease, with the exception of adequately treated localized or in situ non-melanoma carcinoma of the skin (i.e., basal cell carcinoma) or the cervix.

J) Subject has a history of significant multiple and/or severe allergies (e.g., food, drug, latex allergy), or has had an anaphylactic reaction or significant intolerability to prescription or non-prescription drugs (including marijuana or other cannabis-containing drugs) or food.

K) Subject has had major surgery, donated or lost 1 unit (approximately 500 mL) of blood, or has participated in another investigational trial within 4 weeks prior to the pre-study/screening visit. The 4 week window is derived from the date of the last trial medication and/or blood collection in a previous trial and/or adverse event (AE) related to trial drug to the pretrial/screening visit of the current trial. For subjects who have participated in an investigational trial where no trial drug was administered or invasive procedure performed the interval may be revised to include no interval requirement.

L) Subject has had (within 8 weeks of pre-study/screening visit) or plans to have a preventive vaccination during the course of the study (i.e., up to the post-study visit).

M) Subject is unable to refrain from or anticipates the use of any medication, including prescription and non-prescription drugs or herbal remedies (such as St. John's Wort [*Hypericum perforatum*]) beginning approximately 2 weeks (or 5 half-lives) prior to administration of the initial dose of study drug, throughout the study (including washout intervals between treatment periods), until the post-study visit. There may be certain medications that are permitted.

N) Subject consumes excessive amounts of alcohol, defined as >3 servings of alcoholic beverages per day (1 serving is approximately equivalent to: 300 mL [10 ounces] of beer, 125 mL [4 ounces] of wine, 25 mL [1 ounce] of distilled spirits). Subjects that consume no more than 4 servings of alcoholic beverages per day may be enrolled at the discretion of the investigator.

O) Subject consumes excessive amounts of caffeine, defined as >6 servings of coffee, tea, cola, or other caffeinated beverages per day (1 serving is approximately equivalent to 120 mg of caffeine).

P) Subject is currently (defined as within approximately 3 months of the pre-study/screening visit) a regular user (including "recreational use") of any illicit drugs (including marijuana) or has a history of drug (including alcohol) abuse within approximately 6 months of the pre-study/screening visit.

Q) For male subjects: Subject is unwilling or unable to use a condom with female sexual partners from the time of first administration of study drug through three months after the final dose of study drug.

R) For male subjects: Subject is unwilling to refrain from sperm donation from the time of first administration of study drug through three months after the final dose of study drug.

S) Subject has a family history of long QT syndrome.

T) Subject has a QTc interval of >450 msec (based on mean of triplicate ECGs obtained at baseline).

U) The investigator has concerns regarding the safe participation of the subject in the study or for any other reason the investigator considers the subject inappropriate for participation in the study.

Investigational product, dosage and mode of administration: Investigational drug product, hydrochloride salt of Compound 1, Capsules and matching placebo are supplied to the clinical research unit as formulated dry powder 2-, 10-, and 50-mg (free base equivalents) capsules for oral administration. Study drug is provided to the clinic site in appropriately labeled bulk packaging. An unblinded pharmacist (or designee under the direct supervision of the unblinded pharmacist) at the clinical site, who is otherwise not connected with the conduct of the study, dispenses blinded study drug for administration to subjects according to the provided allocation schedule. For Part 2, study drug to support dosing of individual subjects for up to the entire dosing duration (i.e., 14 days) may be repackaged at the clinical site by the unblinded pharmacist (or designee under the direct supervision of the unblinded pharmacist). These repackaged blinded clinical supplies are administered to subjects at the clinical site only.

Duration of Treatment:

Part 1: In Part 1, total study participation is approximately 84 days (including a 28 day screening period). There is a minimum washout period of at least 7 days between treatments in Part 1.

Part 2: In Part 2, total study participation is approximately 56 days (including a 28 day of screening period).

Reference Therapy, Dosage and Mode of Administration.

Part 1: In Panels A and B, each subject receives single ascending oral doses of the hydrochloride salt of Compound 1 or matching placebo in up to 4 treatment periods separated by a minimum 1-week washout interval between doses. There is a minimum 72-hour period between administration of study drug in Panels A and B. In addition, there is a minimum 2-week washout between Panel B Period 2 and Panel A Period 3 in order to evaluate available preliminary pharmacokinetic data along with safety and tolerability data from the preceding doses before proceeding with dosing in Periods 3 and 4. All doses are administered orally, together with approximately 240 mL of water. Water is otherwise restricted from 1 hour prior to, and for 1 hour after administration of study drug. In each treatment period, with the exception of Panel A Period 4 (food effect treatment period); study drug is administered after an overnight fast (for approximately 8 hours).

Panel A: Subjects receive single 2-, 18-, 100- and 18-mg (with food) doses of the hydrochloride salt of Compound 1 (n=6) or matching placebo (n=2) in Periods 1 through 4. The allocation schedule for Periods 2 and 4 (fasted versus fed) are the same such that the same subjects receive active drug or matching placebo in the respective treatment periods.

In Panel A Period 4, study drug are administered after consumption of a high-fat breakfast. The composition of the high-fat breakfast is: 2 fried or scrambled eggs, 2 strips bacon, 2 slices toast with 2 pats butter, 4 oz (113 gram) hash browns (fried potato), 240 mL whole milk (nutritional content approximately 55.6 gram fat, 55 gram carbohydrate, 31.1 gram protein; total calories=500.4 as fat, 220 as carbohydrate, 124.4 as protein). In this food-effect treatment period, subjects also fast from all food and drink, except water, for approximately 8 hours prior to study drug administration. However, approximately 30-minutes prior to study drug administration, subjects begin to consume the high-fat breakfast as described above. This meal should be consumed in its entirety over a 20-minute duration. Approximately 10 minutes after consuming the meal, subjects are administered their dose of study drug with approximately 240 mL water, and water is otherwise restricted for a further 1 hour after study drug administration.

Panel B: Subjects receive single 6-, 50-, 200-, and 400-mg doses of the hydrochloride salt of Compound 1 (n=6) or matching placebo (n=2) in Periods 1 through 4.

The suggested doses of the hydrochloride salt of Compound 1 for dose escalation in Part 1 (Panels A and B) are provided in Table 2.

TABLE 2

| Panel:[a),b),c)] | Period 1 | Period 2 | Period 3 | Period 4 |
|---|---|---|---|---|
| Panel A | 2 mg | 18 mg[d)] | 100 mg | 18 mg (fed)[e)] |
| Panel B | 6 mg | 50 mg | 200 mg | 400 mg |

[a)]Subjects are randomized to receive single oral doses of the hydrochloride salt of Compound 1 (n = 6) or matching placebo (n = 2).
[b)]Different subjects participate in each panel.
[c)]The stated doses c be adjusted downwards based on evaluation of safety, tolerability, and/or pharmacokinetic data form previous panels or treatment periods.
[d)]For Panel A subjects, the assigned treatment in Period 4 are identical to that in Period 2 such that the same subjects receive placebo in these two treatment periods.
[e)]Hydrochloride salt of Compound 1 to be administered with high-fat breakfast; dose of the hydrochloride salt of Compound 1 is repeated per subject based on the dose received in Period 2.

Note that the doses proposed here may be adjusted downwards based on preliminary pharmacokinetic, safety and tolerability data from preceding Panels or Periods.

Preliminary pharmacokinetic data from subjects in this study guide dose escalation to the higher doses. A pharmacokinetic pause occurs after Period 2 in Panel B, in order to assess available pharmacokinetic data along with safety and tolerability data prior to further dose escalation in Period 3 in Panel A. The planned doses may be adjusted downward based on evaluation of safety, tolerability, and/or pharmacokinetic data from previous panels or treatment periods.

Part 2: In Panels C through G, each subject receives daily oral doses of the hydrochloride salt of Compound 1 or matching placebo for up to 14 days. All doses are administered orally, together with approximately 240 mL of water. Water is otherwise restricted from 1 hour prior to, and for 1 hour after administration of study drug. Part 2 only initiates once preliminary pharmacokinetic, safety and tolerability data are available from Part 1 Panel A Period 3 (100 mg dose). Prior to dosing in the first Panel in Part 2 (i.e., Panel C), a dose selection memo/interim report is provided to the Investigator and to the Ethics Review Committee (ERC)/Institutional Review Board (IRB). Dosing in Panel C does not proceed until the Investigator has received approval of the dose selected for Panel C from the ERC/IRB. Panels are conducted sequentially: dosing in a subsequent Panel only commences after preliminary evaluation of safety and tolerability data from the dosing phase of the preceding Panel has been evaluated (no less than one week between the first dose in Panels D, E, F, and G and the final dose in Panels C, D, E, and F respectively). In each treatment period, study drug is administered after an overnight fast (for approximately 8 hours).

Panel C: Subjects receive daily oral 10-mg doses of the hydrochloride salt of Compound 1 (n=6) or matching placebo (n=2) for up to 14 days.

Panel D: Subjects receive daily oral 20-mg doses of the hydrochloride salt of Compound 1 (n=6) or matching placebo (n=2) for up to 14 days.

Panel E: Subjects receive daily oral 40-mg doses of the hydrochloride salt of Compound 1 (n=6) or matching placebo (n=2) for up to 14 days.

Panel F: Subjects receive daily oral 80-mg doses of the hydrochloride salt of Compound 1 (n=6) or matching placebo (n=2) for up to 14 days.

Panel G: Subjects receive daily oral 160-mg doses of the hydrochloride salt of Compound 1 (n=6) or matching placebo (n=2) for up to 14 days.

Note that the doses proposed here may be adjusted downwards based on preliminary pharmacokinetic, safety and tolerability data from preceding Panels or Treatment Periods.

For all single-doses (i.e., all doses in Part 1) and for the first (Day 1) and last (Day 14) doses administered in Part 2, all subjects fast for a minimum of approximately 4-hours post-dose (except for water, which is permitted starting 1 hour after dosing). A standardized lunch is administered approximately 4 hours post-dose, a standardized dinner at approximately 10 hours post-dose, and snacks may be offered at 7 and 13 hours post-dose. For the purposes of this study, "standardized" means that the caloric content and composition should be similar across treatment periods and panels. For non-dosing days (Part 1) and for non-dosing days and dosing days 2 through 13 (Part 2), meals do not need to be standardized.

The suggested doses of the hydrochloride salt of Compound 1 for dose escalation in Part 2 (Panels C through G) are provided in Table 3.

TABLE 3

| | [a),i),ii)]Panel: | | | | |
|---|---|---|---|---|---|
| | Panel C | Panel D | Panel E | Panel F | Panel G |
| Dose of hydrochloride salt of Compound 1 | 10 mg | 20 mg | 40 mg | 80 mg | 160 mg |

[a)]Subject is randomized to receive single oral doses of hydrochloride salt of Compound 1 (n = 6) or matching placebo (n = 2).
[i)]Different subjects participate in each panel.
[ii)]The stated doses may be adjusted downwards based on evaluation of safety, tolerability, and/or pharmacokinetic data from previous panels or treatment periods.

Criteria for Evaluation:
Pharmacokinetics/Pharmacodynamics:
Blood and urine for determination of Compound 1 plasma and urine concentrations.

The urine is potentially analyzed for qualitative metabolite characterization.

In Part 1, urine samples for the determination of urinary Compound 1 concentrations are collected predose, and up to 48 hours post-dose in a selected treatment period in Part 1, as appropriate (at the highest expected dose (SAD), and in one treatment period only).

Urine samples are collected for up to 48 hours after the final dose of study drug on Day 14 of each treatment panel (in two collection aliquots: 0-24 h and 24-48 h). The decision to assay these urine samples for Compound 1 quantification and urinary excretion characterization, and potentially for qualitative metabolite characterization, is made based on preliminary urinary PK data from Part 1. Based on these Part 1 urinary PK data, no, some, or all urine PK samples collected in Part 2 are assayed. In addition, based on preliminary data, urine collection in later Panels may be discontinued. If necessary, and to increase the sensitivity of detection, urine samples from subjects in a given Panel may be pooled prior to analysis.

Safety: The safety and tolerability of the hydrochloride salt of Compound 1 is monitored by clinical assessment of adverse events and by repeated measurements of vital signs, physical examination, weight, neurological examinations, 12-lead electrocardiograms (ECGs), and by the standard clinical laboratory safety tests (hematology, chemistry, and urinalysis).

Adverse event inquiry occurs at 0 hour (pre-dose) and at each visit throughout the study, up to and including the post study visit (at least 14 days after the last dose of study drug).

Statistical Methods:

Sample Size/Power: Sample size for initial human safety studies are limited and chosen based on customary values. Power calculations for comparison of adverse event rates are too imprecise to be clinically meaningful because the actual rates are not even approximately known. However, if an adverse event occurs at a rate of 1% or 10% then the probability of observing such an adverse event among the 6 subjects receiving that dose is 6% or 47%, respectively. If no AE of a given type is observed in any of the 6 subjects at a given dose then, with 80% (90%) confidence, the true incidence of the adverse event at that dose is at most 24% (32%).

Randomization: Subjects are randomized within a cohort according to a computer-generated random code.

Statistical Methods:

PK: Descriptive statistics are provided by treatment (Part 1) and by treatment and day (Part 2). Minimum, median, maximum and CV are provided for all PK parameters. Arithmetic mean and standard deviation based on the raw scale are provided for AUC and $C_{max}$. In addition, the percent CV of AUC and $C_{max}$ is also provided and calculated according to the following formula: $100 \times \mathrm{sqrt}(\exp(s2)-1)$, where s2 is the observed variance on the natural log-scale. Harmonic mean and jack-knife SD is provided for half-life. Time to steady-state, and evaluation of PK linearity are evaluated in an exploratory fashion.

Pharmacodynamics:

Part 1

Single-dose 2-AG concentrations and MGLL TE percentages are listed and summarized by time point and treatment using descriptive statistics. For each subject and each post-baseline time point, percent of baseline is calculated. Baseline is defined as the level in the last sample before test treatment of each period. Percent of baseline is computed via back-transformation from log-scale summary statistics. Other PD readouts may be summarized similarly.

Part 2

Multiple-dose 2-AG concentrations and MGLL TE percentages are listed and summarized by day and treatment using descriptive statistics. For each subject and each post-baseline time point, percent of baseline are computed via back-transformation from log-scale summary statistics. Other PD readouts may be summarized similarly.

Part 1 (Single Ascending Dose, Panels A and B) Results

Seventeen healthy male subjects had received at least one dose of study drug in Part 1. When administered in the fasting state, single oral doses up to 200 mg of Compound 1 HCl were not associated with any vital sign, safety laboratory, or electrocardiographic findings of note.

Compound 1 plasma concentrations were detectable at the 2-mg dose level, and increased with increasing dose. A summary of preliminary mean PK data is shown in Table 4. At the highest dose level administered (200 mg), mean $C_{max}$=109 ng/mL, mean $T_{max}$=3.0 hr, median $t_{1/2}$=3.61 hr, and mean $AUC_{inf}$=766 ng·hr/mL.

TABLE 4

| Dose (mg) | $C_{max}$ (ng/mL)* | SD $C_{max}$ | $T_{max}$ (hr)* | SD $T_{max}$ | $AUC_{inf}$ (hr · ng/mL)* | SD $AUC_{inf}$ | $T_{1/2}$ (hr)# |
|---|---|---|---|---|---|---|---|
| 2 | 2.90 | 1.15 | 1.50 | 0.54 | 15.9 | 5.18 | 1.51 |
| 6 | 10.2 | 5.33 | 1.67 | 0.51 | 47.0 | 7.83 | 2.23 |
| 18 | 23.5 | 14.7 | 2.00 | 1.1 | 109 | 75.2 | 3.02 |
| 50 | 59.8 | 19.5 | 1.80 | 0.44 | 296 | 121 | 3.44 |
| 100 (A3) | 45.7 | 40.0 | 3.17 | 2.56 | 289 | 185 | 5.82 |
| 100 (B4) | 76.0 | 41.7 | 1.83 | 0.40 | 512 | 355 | 3.76 |
| 200 | 109 | 62.9 | 3.00 | 2.45 | 766 | 383 | 3.61 |

*Mean;
Median;
A3 = Panel A, Period 3;
B4 = Panel B, Period 4;
SD = Standard Deviation As shown in Table 4, there was a difference in the mean and SD of plasma PK parameter values for the two treatment periods (Panel A, Period 3; Panel B, Period 4) in which the 100 mg dose was administered: the values for Period A3 were lower than those for Period B4, and also were not consistent with the dose-related increases observed across all other doses administered in the fasted state in Part 1 of the study. As described below, the peripheral blood mononuclear cell (PBMC) MGLL target engagement (TE) data indicated similar TE in Periods A3 and B4, that was greater than, and distinct from that in Period B2 in which a 50 mg dose was administered. These data suggest that the plasma PK data for Period A3 are anomalous. An evaluation of the laboratory procedures associated with the bioanalysis of these PK samples did not reveal a cause for this apparent anomaly, and values for both treatment periods are reported here for completeness.

Figure 6:
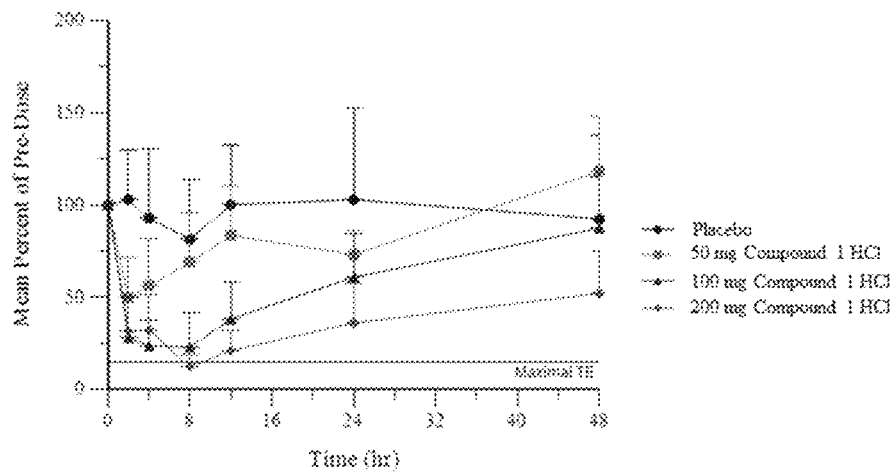
FIG. 6 shows the time and dose dependent inhibition of MGLL activity following oral administration of Compound 1 to human subjects using exogenous 2-AG as a substrate to assay ex vivo MGLL-mediated hydrolysis in PBMC.

Peripheral Blood Mononuclear Cell (PBMC) aliquots were collected from subjects in order to evaluate in an exploratory fashion the dose- and time-dependence of Compound 1 mediated inhibition of MGLL, also referred to as MGLL target engagement (TE). Preliminary data from selected treatment periods are shown in FIG. 6 wherein the activity of MGLL is assayed in PBMC fractions by a hydrolysis assay in which exogenous 2-arachidonylglycerol (2-AG) is added to the PBMC pellet and the generation of arachidonic acid (AA) quantitated by mass spectroscopy. The hydrolytic activity at baseline (i.e., predose) is set at 100%. Inhibition of MGLL results in decreased hydrolysis of 2-AG in a time- and dose-dependent manner as indicated here. MGLL accounts for the majority of 2-AG hydrolysis under these conditions, however there is an MGLL-independent component, the magnitude of which is indicated on the graph by the maximal TE line, which represents the hydrolysis of 2-AG in PBMC pellets that have been pre-incubated with an excess of Compound 1.

As indicated in FIG. 6 oral administration of Compound 1 HCl was associated with a time- and dose-dependent inhibition of MGLL hydrolytic activity. Following the 50 mg dose, mean maximal inhibition of MGLL activity occurred at approximately 2 hours postdose, whereas after the 100 mg and 200 mg doses, mean maximum inhibition occurred at approximately 4-8, and 8 hours respectively. The 200 mg dose of Compound 1 HCl was associated with complete inhibition of MGLL in PBMC at approximately 8 hours postdose, followed by a gradual return towards baseline activity. The 50 mg dose of Compound 1 HCl was associated with approximately 46% mean maximum reduction in total PBMC 2-AG hydrolytic activity, which corresponds to a mean-maximum MGLL-inhibition of approximately 54% after this dose.

Part 2 (Multiple Ascending Dose, Panels C-D) Results

There were no adverse events leading to the discontinuation of any subjects in Panel C (10 mg QD×14 days) or Panel D (20 mg QD×14 days) and no clinically significant changes in vital signs, laboratory test values, or ECGs.

Figure 7:
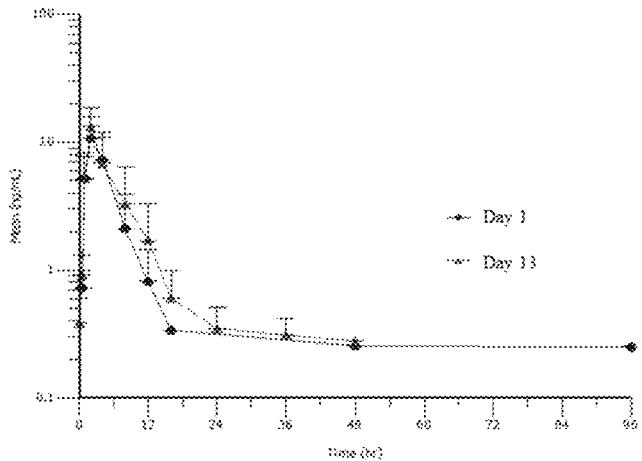
FIG. 7 shows mean Compound 1 plasma concentrations measured on Days 1 and 13 in Panel C (10 mg QD×14 days).
Figure 8:
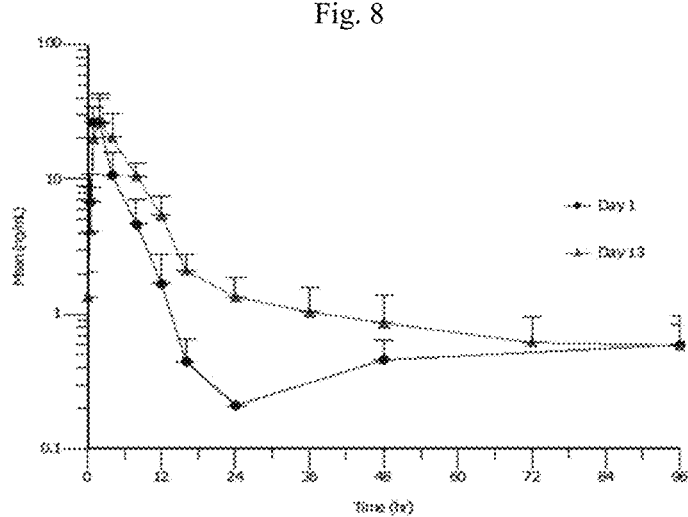
FIG. 8 shows mean Compound 1 plasma concentrations measured on Days 1 and 13 in Panel D (20 mg QD×14 days).

For Panels C and D, the mean Compound 1 plasma PK profiles measured on days 1 and 13 of dosing are shown in FIG. 7 and FIG. 8 respectively. The preliminary PK data from these partial Panels, indicate Compound 1 plasma $AUC_{0-24h}$ accumulation ratios (Day 13/Day 1) of ~1.2 and ~1.7, and plasma $C_{max}$ accumulation ratios (Day 13/Day 1) of ~1.2 and ~1.2 for Panels C and D respectively. All daily doses of study drug in Part 2 were administered in the fasted state.

Figure 9:
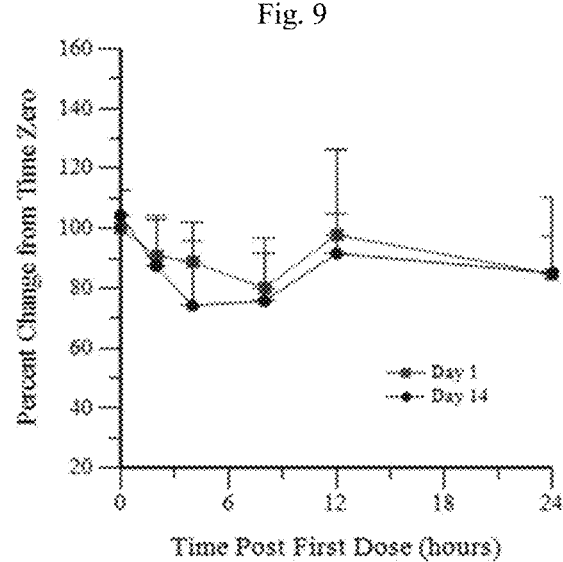
FIG. 9 shows mean percent of Day 1 pre-dose baseline PBMC-mediated hydrolysis of 2-AG versus time post-dose in Placebo recipients (Panels C and D combined).
Figure 10:
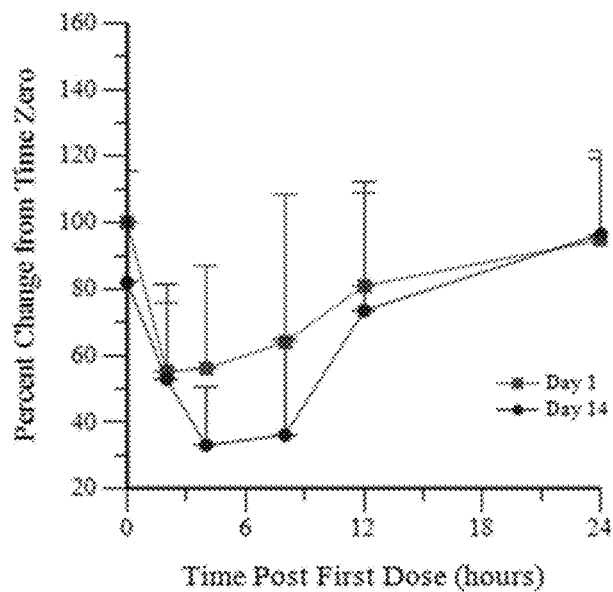
FIG. 10 shows mean percent of Day 1 pre-dose baseline PBMC-mediated hydrolysis of 2-AG versus time post-dose in Panel C (10 mg QD×14 days).
Figure 11:
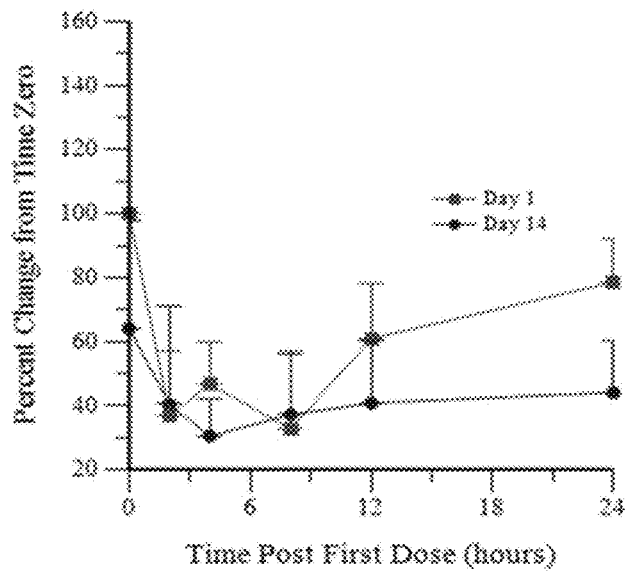
FIG. 11 shows mean percent of Day 1 pre-dose baseline PBMC-mediated hydrolysis of 2-AG versus time post-dose in Panel D (20 mg QD×14 days).

Preliminary biomarker (PBMC MGLL Target Engagement as measured by PBMC-mediated hydrolysis of 2-AG) data from the fourteen subjects who have completed dosing in Panels C and D (seven subjects in each of the two Panels) are shown with the relevant preliminary PBMC target engagement data for Placebo recipients (Panels C and D combined), Compound 1 HCl 10 mg QD (Panel C), and 20 mg QD (Panel D) in FIG. 9, FIG. 10, and FIG. 11 respectively. These preliminary data from partially-completed Panels, suggest that after 14 days of Compound 1 HCl daily doses of 20 mg, MGLL in PBMC remains substantially inhibited at the end of the 24 hour dosing interval (FIG. 11). At the 10 mg QD dose, mean MGLL inhibition at the end of the dosing interval is similar on dosing Days 1 and 14, suggesting that MGLL hydrolytic activity is able to recover fully by 24 hours after dosing of Compound 1 HCl at 10 mg QD (FIG. 10).

Example 7. A Single-Dose, Randomized, Placebo Controlled, Two Period Crossover Study of the Effects of Compound 1 Hydrochloride Salt on Gastric Accommodation and Nutrient Volume Tolerance The primary objective of this study is to assess the effect of Compound 1 HCl on gastric accommodation in patients with functional dyspepsia (FD).

Assess the effect of Compound 1 HCl on nutrient volume tolerance compared to placebo;

Assess safety and tolerability of Compound 1 HCl in FD subjects;

Assess changes in IGP, nutrient volume tolerance, satiety (Satiety Scale, Appendix F) and epigastric symptoms (VAS for Epigastric Symptoms, Appendix G) as related to Compound 1 HCl plasma concentrations (e.g., $C_{max}$, $AUC_{0-4}$, $AUC_{0-24}$) and monoacylglycerol lipase (MGLL) enzyme activity in peripheral blood mononuclear cells (PBMC).

Patients: Twelve adult male or female patients with functional dyspepsia, and with previously identified impaired gastric accommodation, between the ages of 18 and 65 years will be enrolled.

Criteria:

Inclusion Criteria:

Patient has functional dyspepsia, defined by the Rome III criteria (Appendix E). The patient must have either the cardinal symptom of bothersome postprandial fullness or early satiation for the last 3 months, with symptom onset at least 6 months prior to screening and in the absence of organic, metabolic or systemic diseases that can explain these symptoms.

Patient has, upon clinical review, evidence of impaired gastric accommodation based on a barostat test, a nutrient volume tolerance test with intragastric pressure measurement, or by other, similar evaluations. The evidence for this abnormality will be recorded.

Patient's Rome III Questionnaire results indicates that the intensity of co-existing epigastric pain and/or epigastric burning may be present, but have the same or lesser intensity than the evaluations of postprandial fullness or early satiety (i.e. epigastric pain and burning are not the prominent symptoms of the patient's functional dyspepsia).

Patient recall of symptoms of gastrointestinal reflux (e.g. heartburn, regurgitation) over the past 8 weeks has no more than 2 episodes per week of heartburn or regurgitation considered mild in intensity. (The Reflux Disease Questionnaire (RDQ) will collect these symptoms)

Patient is willing to discontinue specific drugs that affect gut motility for at least 2 weeks prior to each treatment period. Restricted drugs include opioids (e.g. loperamide), dopamine antagonists (e.g. metoclopramide, domperidone, alizapride), other prokinetic agents (e.g. cispride, tegaserod), acid secretion (e.g. H2 antagonists and proton pump inhibitors such as omeprazole, esomeprazole, lansoprazol, pantoprazol), and erythromycin.

Patient understands the study procedures and agrees to participate in the study by giving written informed consent.

Patient is a male or female between 18 and 65 years of age at the pre-study/screening visit; further:

If subject is a male, he is willing to use a condom with female sexual partners from the time of first administration of study medication and for 3 months following the last dose of study medication.

Subject is willing to refrain from sperm donation from the time of first administration of study medication and for 3 months following the last dose of study medication.

If subject is a postmenopausal female: subject is without menses for at least 1 year and has a documented follicle stimulating hormone (FSH) level in the postmenopausal range at the pre-study/screening visit.

If subject is a surgically sterile female: subject is status-post hysterectomy, bilateral oophorectomy, or tubal ligation. (Hysterectomy may be confirmed by ultrasound or other imaging technique if documentation is not available. Oophorectomy and tubal ligation must be confirmed by documentation).

If subject is a woman of child bearing potential (WOCBP), she agrees to use two methods of barrier contraception which may include cervical cap with spermicide, diaphragm with spermicide, condom with spermicide, or intrauterine device (IUD) from time of screening through the last study visit. In addition, WOCBP will have a negative urine pregnancy test at screening and before being dosed with study medication. WOCBP who are using injectable contraceptives, implanted contraceptives, medicated ring contraceptives or oral contraceptive methods may participate, but must use one method of barrier contraception such as cervical cap with spermicide, diaphragm with spermicide, or condom with spermicide.

Patient has a Body Mass Index (BMI)>18 to ≤30 kg/m² at the pre-study/screening visit.

BMI=weight (kg)/height (m)² (BMI calculation should be rounded to the nearest whole number).

Patient is judged to have no unmanaged significant disease or disorder based on medical history, physical examination, vital sign measurements, and laboratory safety tests (see Appendix B for interpretation of laboratory findings) obtained at pre-study/screening, and within 24 hours prior to first administration of study drug.

Patient has no clinically significant abnormality of ECG performed at pre study/screening, and prior to first administration of study drug.

Patient is a nonsmoker or is a social smoker using no more than 2 cigarettes per day, and is willing to abstain from smoking and nicotine containing products before reporting to the clinical research unit until discharge at the completion of study procedures.

Patient is willing to comply with the study restrictions.

Patient is willing to undergo the nutrient volume tolerance tests.

Exclusion Criteria:

Patient is under the age of legal consent.

Female patients who are pregnant or breastfeeding.

Patient has a personal history of a clinically significant psychiatric disorder (including severe affective disorder, anxiety disorder, post-traumatic stress disorder, psychotic disorder or drug-induced psychoses). Patients who have had adjustment disorder with anxious or depressive features in the past may be enrolled at the discretion of the Investigator.

Patient has a first-degree family history of schizophrenia, severe affective disorder, severe anxiety disorder, or other psychosis.

Patient is taking antidepressants including SSRIs, SNRIs, tricyclic antidepressants, or atypical antidepressant medications such as bupropion, mirtazapine, trazodone or agomelatine. Patients taking these or other types of medicine for anxiety are also excluded. Patients who have discontinued antidepressants more than 6 months ago may be enrolled at the discretion of the Investigator. Patients who are taking gabapentin or pregabalin or buspirone are also excluded.

Patient is mentally or legally incapacitated, has significant emotional problems at the time of pre-study/screening visit or is expected to have potential for mental incapacitation during the conduct of the study.

Patient has a history of any illness that, in the opinion of the study Investigator, might confound the results of the study or pose an additional risk to the subject by virtue of their participation in the study.

Patient has had any gastrointestinal surgery. Those having undergone appendectomy more than 1 year prior to the pre-study/screening visit may participate.

Patient has had any acute gastrointestinal illness in the past 3 months.

Patient has an estimated creatinine clearance (CrCl) of ≤80 mL/min based on the Cockcroft-Gault equation. An actual creatinine clearance, as measured using a 24-hour urine collection, may be used in place of, or in conjunction with the Cockcroft-Gault calculation. Subjects with an actual or calculated creatinine clearance that is in the range of 72-79 mL/min (i.e., within 10% of 80 mL/min) may be enrolled in the study at the discretion of the Investigator.

CrCl=(140−age [yr])*(body weight [kg])/(72)serum creatinine [mg/dL])    Cockcraft-Gault Equation:

For female subjects, multiply by 0.85 to obtain creatinine clearance

Subject has an active or prior history of neurological disorder, including but not limited to seizure disorder, epilepsy, stroke, neurological disease, cognitive impairment, head trauma with prolonged loss of consciousness (>10 minutes), or migraine headaches.

Patient is unable to refrain from or anticipates the use of any medication, including prescription and non-prescription drugs or herbal remedies (such as St. John's Wort [*Hypericum perforatum*]) beginning approximately 1 week prior to administration of the initial dose of study drug, throughout the study (including washout intervals between treatment periods), until the second treatment period. There may be certain medications that are permitted.

Patient has a history of clinically significant neoplastic disease, with the exception of adequately treated localized or in situ non-melanoma carcinoma of the skin (e.g., basal cell carcinoma) or the cervix.

Patient has a history of significant multiple and/or severe allergies (e.g., food, drug, latex allergy), or has had an anaphylactic reaction or significant intolerability to prescription or non-prescription drugs (including marijuana or other cannabis-containing drugs) or food.

Patient has had major surgery, donated or lost 1 unit (approximately 500 mL) of blood, or has participated in another investigational trial within 4 weeks prior to the pre-study/screening visit. The 4 week window will be derived from the date of the last trial medication and/or blood collection in a previous trial and/or adverse event (AE) related to trial drug to the pretrial/screening visit of the current trial. For patients who have participated in an investigational trial where no trial drug was administered or invasive procedure performed the interval may be revised to include no interval requirement.

Patient has had (within 8 weeks of pre-study/screening visit) or plans to have a preventive vaccination during the course of the study (e.g., up to the post-study visit).

Patient consumes excessive amounts of alcohol, defined as >3 servings of alcoholic beverages per day (1 serving is approximately equivalent to: 300 mL [10 ounces] of beer, 125 mL [4 ounces] of wine, 25 mL [1 ounce] of distilled spirits). Subjects that consume no more than 4 servings of alcoholic beverages per day may be enrolled at the discretion of the Investigator.

Patient consumes excessive amounts of caffeine, defined as >6 servings of coffee, tea, cola, or other caffeinated beverages per day (1 serving is approximately equivalent to 120 mg of caffeine).

Patient is currently (defined as within approximately 3 months of the pre-study/screening visit) a regular user (including "recreational use") of any illicit drugs (including marijuana) or has a history of drug (including alcohol) abuse within approximately 6 months of the pre-study/screening visit. Further, patient is unwilling to refrain from the use of cannabis products during this study.

Subject has a family history of long QT syndrome.

Subject has a QTc interval of >450 msec (male subjects) or >470 msec (female subjects).

The Investigator has concerns regarding the safe participation of the patient in the study or for any other reason the Investigator considers the subject inappropriate for participation in the study.

Subjects/patients will be randomized to a crossover treatment sequence A or B according to a computer-generated random code.

|  | Period 1 | Period 2 |
|---|---|---|
| Sequence A: | Placebo | Compound 1 HCl |
| Sequence B: | Compound 1 HCl | Placebo |

Blinding: Compound 1 HCl or matching placebo will be prepared using the randomization allocation schedule by an unblinded pharmacist without other responsibilities for the collection of safety or efficacy data.

Duration of Treatment: Total study participation will be approximately 83 days, including a 60 day screening period. There will be a minimum washout period of at least 7 days between two single day treatments. Efforts should be made to complete the second treatment within 4 weeks of the first treatment. WOCBP not using hormonal contraception should be studied at each of the two treatment periods at the same point in their menstrual cycle.

The primary endpoint is the change in IGP over time during nutrient meal infusion (gastric accommodation) comparing Compound 1 versus placebo. For each subject this is computed from the area between the pressure time curve and the zero line (with values above zero contributing negatively) from the beginning of the nutrient drink infusion until it ceases.

Other endpoints include the Satiation Score and VAS for Epigastric Symptoms measured over time during the nutrient volume tolerance test, and in the period after the nutrient volume tolerance test until the pressure transducer is removed.

Example 8: Phase 2 Single Site, Randomized, Double-Blind, Placebo Controlled Trial of Compound 1 in Subjects With Alzheimer's Disease The purpose of this study is to evaluate the safety and efficacy of Compound 1 HCl in the treatment of Alzheimer's Disease.

Patients: Eligible subjects will be men and women 40 years to 95 years of age.

Criteria:
Inclusion Criteria:
NINCDS/ADRDA criteria for probable AD
MMSE between 12-27
Treatment with a cholinesterase inhibitor or an NMDA (N-methyl-D-asparate) antagonist with stable dose for at least 12 weeks
Home monitoring available for supervision of medications
Caregiver available to accompany patient to all visits and willing to participate in study as informant
Fluent in English or Spanish
Medical stability for this study as confirmed by review of records, internist's physical exam, neurological exam, and laboratory tests
Stable doses of non-excluded medication
No evidence of hepatic insufficiency
Able to swallow oral medications
Ability to participate in the informed consent process Exclusion Criteria:
History of Diabetes Mellitus (OGTT criteria) requiring treatment with an excluded antidiabetic medication (see below) or history of hypoglycemia
Active hepatic or renal disease
Cardiac disease including history of congestive heart failure or current treatment for CHF; history of recent myocardial infarction
Use of another investigational drug within the past two months
History of clinically significant stroke
History of seizure or head trauma with disturbance of consciousness within the past two years
Major mental illness including psychotic disorders, bipolar disorder, or major depressive episode within the past two years Medication Exclusion
Current use of oral hypoglycemic agents including sulfonylureas and meglintinides
Current or past treatment with insulin for longer than two weeks
Current use of drugs with significant anticholinergic or antihistaminic properties
Study Design:
Allocation: Randomized
Intervention Model: Parallel Assignment
Masking: Double Blind (Subject, Investigator)
Primary Purpose: Treatment
Primary Outcome Measures:
Change in Alzheimer's Disease Assessment Scale—Cognitive Subscale (ADAS-Cog) Score [Time Frame: Over 6 months, measured at visits 2 (week 2), 6 (week 12), 8 (week 24)] [Designated as safety issue: No]
A psychometric instrument that evaluates memory, attention, reasoning, language, orientation, and praxis.
Secondary Outcome Measures:
Change in Alzheimer's Disease Cooperative Study Clinician's Global Impression of Change (ADCS-CCGIC) Score [Time Frame: Over 6 months, measured at visits 2 (week 2), 6 (week 12), 8 (week 24)] [Designated as safety issue: No]. A systematic method for assessing clinically significant change in a clinical trial as viewed by an independent skilled and experienced clinician. The ADCS-CGIC focuses on clinician's observations of change in the subject's cognitive, functional, and behavioral performance since the beginning of a trial. It relies on both direct examination of the subject and an interview of an informant. Unlike a targeted symptom scale, it takes into account a subject's overall function in the cognitive, behavioral, and functional activity domains.
Change in Mini-Mental State Examination (MMSE) Score [Time Frame: Over 6 months, measured at visits 2 (week 2), 6 (week 12), 8 (week 24)] [Designated as safety issue: No]. A frequently used screening instrument for Alzheimer's disease drug studies. It evaluates orientation, memory, attention, concentration, naming, repetition, comprehension, and ability to create a sentence and to copy two intersecting polygons.
Change in Alzheimer's Disease Cooperative Study Activities of Daily Living Inventory (ADCS-ADL) Score [Time Frame: Over 6 months, measured at visits 2 (week 2), 6 (week 12), 8 (week 24)][Designated as safety issue: No]. ADCS-ADL assesses functional performance in subjects with Alzheimer's disease. In a structured interview format, informants are queried as to whether subjects attempted each item in the inventory during the prior 4 weeks and their level of performance. The ADCS-ADL scale discriminates well between normal controls and mild AD patients. It has good test-retest reliability. The ADCS-ADL includes some items from traditional basic ADL scales (e.g., grooming, dressing, walking, bathing, feeding, toileting) as well as items from instrumental activities of daily living scales (e.g., shopping, preparing meals, using household appliances, keeping appointments, reading).

Change in Neuropsychiatric Inventory (NPI) Score [Time Frame: Over 6 months, measured at visits 2 (week 2), 6 (week 12), 8 (week 24)] [Designated as safety issue: No]. The NPI is a well-validated, reliable, multi-item instrument to assess psychopathology and behavior in AD based on interview with the informant.

Changes in AD Biomarkers [Time Frame: Blood collected at visits 2 (week 2), 6 (week 12), 8 (week 24)] [Designated as safety issue: No]. Plasma beta-amyloid proteins will be collected from blood samples obtained at visit 2 (week 2), visit 6 (week 12), and visit 8 (week 24).

APO-E genotyping [Time Frame: Collected at visit 2 (week 2)][Designated as safety issue: No] APOe e4 is an important genetic risk factor for AD. In this trial, as in many studies of AD and memory and cognition in aging, the APOe e4 allele will be analyzed as a predictor of clinical change over time.

| Arms | Assigned Interventions |
| --- | --- |
| Experimental: Compound 1 HCl Subjects with Alzheimer's Disease Intervention: Drug: Compound 1 HCl | Drug: Drug: Compound 1 HCl A natural product, found in many foods and plants with mild insulin sensitizing effects |
| Placebo Comparator: Placebo Subjects with Alzheimer's Disease Intervention: Drug: Placebo | Drug: Placebo Subjects with Alzheimer's Disease placebo comparator |

Example 9: Investigation of Compound 1 HCl in Patients with Functional Chest Pain About 200,000 new cases of Functional Chest Pain (FCP) are diagnosed annually in USA. FCP is associated with poor quality of life and high health care expenditure. Gastroesophageal reflux disease (GERD), esophageal motility disorders, and psychological disorders may cause FCP. However, the mechanism(s) for FCP continue to be explored and include central and peripheral hypersensitivity as well as biomechanical dysfunction of the esophageal wall. CB 1 receptor activation in synaptic clefts fine tunes neuronal firing and may in fact quell the over excitation associated with hypersensitivity. The purpose of this study is to evaluate the safety and efficacy of Compound 1 HCl in the treatment of Functional Chest Pain.

Patients: Eligible subjects will be men and women 18 years to 75 years of age.

Criteria:

Inclusion Criteria:

At least one episode of chest pain a week in the past month. Previous negative cardiac evaluation (EKG+ non invasive stress test+coronary angiogram). Negative esophageal evaluation for a motility disorder (eg: achalasia) and GERD (normal endoscopy, normal 24 hr pH study, or unresponsive to 6 weeks of BID PPI therapy)

Exclusion Criteria:

Subjects requiring narcotics or other pain medications

Subjects with known GERD (unless responsive to PPI therapy and on a stable dose), esophagitis, Barrett's esophagus or peptic stricture on endoscopy Subjects with previous upper gastrointestinal surgery Pregnancy Subjects with diabetes, neuromuscular disorders, cardiac disorders, or other severe co-morbidities (Cardiovascular, respiratory, renal, hepatic, hematologic, endocrine, neurologic) History of seizure or head trauma with disturbance of consciousness within the past two years Subjects with upper airway symptoms (such as hoarseness, wheezing or laryngospasm)

Medications such as baclofen, sucralfate and prokinetic agents or any agent considered a sedative, hypnotic, or psychoactive drug Known history of substance abuse Subject unable to consent Patient has history of comorbid psychiatric conditions including mania and schizophrenia. Patients will also be excluded who currently have a diagnosis of depression or undergoing treatment for depression Study Design:

Allocation: Randomized

Endpoint Classification: Safety/Efficacy Study

Intervention Model: Parallel Assignment

Masking: Double Blind (Subject, Investigator)

Primary Purpose: Treatment

Primary Outcome Measures:

Chest Pain [Time Frame: Daily assessment for 12 weeks] [Designated as safety issue: No]. Patient will fill out a Chest Pain Questionnaire and symptom diary daily of symptoms which will be normalized to a numerical value for comparison among groups Secondary Outcome Measures:

Chest Pain Intensity [Time Frame: Daily assessment for 12 weeks][Designated as safety issue: No]. Patient will fill out a Chest Pain Questionnaire and symptom diary daily of symptoms which will be normalized to a numerical value for comparison among groups.

GERD Symptom Checklist [Time Frame: Baseline, 2, 4, 8, and 12 weeks][Designated as safety issue: No] [Time Frame: Over 6 months, measured at visits 2 (week 2), 6 (week 12), 8 (week 24)] [Designated as safety issue: No]. Patients will fill out a questionnaire pertaining to GERD symptoms which will be normalized to a numerical value for comparison among groups.

Short Form 36 [Time Frame: Baseline, 2, 4, 8, and 12 weeks] [Designated as safety issue: No]A general health-related quality of life questionnaire that examines 8 domains: Physical Functioning, Role Functioning Physical, Role Functioning Emotional, Mental Health, Vitality, Bodily Pain, General Health, and Social Functioning.

Esophageal Hypersensitivity and Distention [Time Frame: Baseline, 4, 8, and 12 weeks][Designated as safety issue: No]. Sensory thresholds for first sensation, discomfort, and pain in the esophagus. Frequency, amplitude, area under the curve (AUC) of reactive esophageal contractions.

| Arms | Assigned Interventions |
|---|---|
| Experimental: Compound 1 HCl Patients who receive Compound 1 HCl, every other night, orally | Drug: Compound 1 HCl Compound 1 HCl, every other night, orally |
| Placebo Comparator: Placebo Patients who receive placebo, every other night, orally | Drug: Placebo Placebo--no drug |

Example 10: Phase 3 Clinical Study of Compound 1 HCl for Multiple Sclerosis Pain and Spasticity The purpose of this study study is to assess the efficacy and safety of Compound 1 HCl compared with placebo on the reduction of pain severity in participants with central neuropathic pain and moderate to severe spasticity due to Multiple Sclerosis.

Patients: Eligible subjects will be men and women 18 years to 75 years of age.

Criteria:
Inclusion Criteria:
Have central neuropathic pain due to multiple sclerosis (MS) based on the disease diagnostic criteria
Adult males or females
Have a score of 4 or greater on the daily 24-hour average pain score
Females must test negative for pregnancy at study entry
Complete the daily diaries for at least 70% of the days of the study
Participants may continue other prescription and nonprescription analgesic pain medications as long as the dose has been stable for 1 month prior to study entry, and they agree to maintain that stable dose throughout the study Disease Diagnostic Criteria:
Diagnosis of MS at least 1 year prior to study entry
No MS flares or change in disease treatment for the 3 months prior to study entry
Daily pain due to MS for a minimum of 3 months prior to study entry
Exclusion Criteria:
Are currently in a clinical trial of MS disease-modifying therapy
Have pain that cannot be clearly differentiated from causes other than MS
Any current or historical diagnosis of mania, bipolar disorder, psychosis, or schizoaffective disorder
History of substance abuse or dependence
Are pregnant or breast-feeding
Study Design:
Allocation: Randomized
Endpoint Classification: Safety/Efficacy Study
Intervention Model: Parallel Assignment
Masking: Double Blind (Subject, Investigator)
Primary Purpose: Treatment
Primary Outcome Measures:
Change From Baseline in the Weekly 24-Hour Average Pain Scores at Week 6 (Acute Phase) [Time Frame: Baseline, 6 weeks] [Designated as safety issue: No]. 24-hour average pain severity scores recorded daily on an 11-point Likert scale, evaluated as a weekly mean, with scores ranging from 0 (no pain) to 10 (worst possible pain). Participants should complete electronic diary each day upon awakening. The 11-point Likert scale was used for assessment of 24-hour average pain and evaluated as weekly means. Scores range from 0 (no pain) to 10 (worst possible pain). The Least Squares Mean (LS Mean) Value was adjusted for investigative site and baseline severity.

Change From Baseline in Spasticity NRS score at Week 6 [Time Frame: Baseline, 6 weeks][Designated as safety issue: No]. The spasticity Numeric Rating Scale is a 0 to 10 patient reported scale of spasticity severity, with 0 being no spasticity and 10 being worst possible spasticity.

Secondary Outcome Measures:
Change From Baseline in the Weekly 24-Hour Average Pain Scores up to Week 6 (Acute Phase) [Time Frame: Baseline, 6 weeks] [Designated as safety issue: No]. This is a nominal outcome reflecting whether or not a clinically-important efficacy outcome (≥30% or ≥50% pain reduction from baseline) was achieved at endpoint. It is based on a comparison between baseline and endpoint scores on an ordinal scale with scores from 0 (no pain) to 10 (worst possible pain). Used were the weekly mean of the scores of the average pain severity over the last 24 hours. The weekly averages were based on daily assessments recorded by participants in their diaries.

Change From Baseline in Ashworth Spasticity Score at Week 6 [Time Frame: 6 weeks][Designated as safety issue: No]. The Ashworth spasticity score is a physician assessed rating of spasticity using a five point score from 0 to 4 for each muscle group tested.

Patient Global Impressions of Improvement Scale (PGI-I) at 6 Weeks [Time Frame: 6 weeks][Designated as safety issue: No]. A scale that measures the participant's perception of improvement at the time of assessment compared with the start of treatment. The score ranges from 1 (very much better) to 7 (very much worse). The Least Squares (LS) Mean Value was adjusted for investigative site and baseline severity.

Change From Baseline in the Brief Pain Inventory Severity and Interference Scores (BPI-S/BPI-I) at Week 6 (Acute Phase) [Time Frame: Baseline, 6 weeks] [Designated as safety issue: No]. Measures pain severity and interference on function. Severity scores: 0 (no pain) to 10 (severe pain) on each question assessing worst, least, and average pain in past 24 hours, and pain right now. Interference scores: 0 (does not interfere) to 10 (completely interferes) on each question assessing pain interference in past 24 hours, such as general activity, mood, normal work, relations with other people, and sleep. Average interference=average of non-missing scores of individual interference items. Least Squares (LS) Mean Value was adjusted for investigative site and baseline severity.

Change From Baseline in the Weekly Mean of Night Pain Scores at Week 6 (Acute Phase) [Time Frame: Baseline, 6 weeks] [Designated as safety issue: No]. Weekly mean of the night pain severity scores recorded daily on an 11-point Likert scale, an ordinal scale ranging from 0 (no pain) to 10 (worst possible pain). Participants should complete the electronic diary each day upon awakening. The Least Squares (LS) Mean Value was adjusted for investigative site and baseline severity.

| Arms | Assigned Interventions |
| --- | --- |
| Experimental: Compound 1 HCl | Drug: Drug: Compound 1 HCl<br>Participants received 30 mg Compound 1 HCl (po, QD) for 1 week followed by 5 weeks at 60 mg in the acute placebo-controlled period. If the participant completes the double-blind portion of the trial, the participant will be offered the option to participate in the open-label extension period (given 10, 20, or 40 mg QD for 12 weeks). |
| Placebo Comparator: Placebo | Drug: Placebo<br>Participants received placebo oral (po), once daily (QD) for 6 weeks (acute phase). If the participant completes the 6-week double-blind portion of the trial, the participant will be offered the option to participate in the open-label extension period (given 10, 20, or 40 milligrams [mg] QD for 12 weeks). |

Example 11: Use of Compound 1 HCl for the Treatment of Inflammatory Bowel Disease (IBD)

The purpose of this study study is to examine in a double blind placebo controlled fashion the effect of Compound 1 HCl on disease activity in patients with IBD.

Patients: Eligible subjects will be men and women 20 years to 80 years of age.
Criteria:
Inclusion Criteria:
Patients with a diagnosis IBD at least 3 months before recruitment will be eligible to the study.
Patients with active disease who are resistant to either 5 ASA, steroids or immunomodulators
Disease activity index of either CDAI of more then 200 in Crohn's disease or Mayo score above 3 in UC.
Age above 20
Exclusion Criteria:
Patients with a known mental disorder
Pregnant women
Patients who are sensitive to any of the ingredients of the study medication.
Patients who are unable to give informed consent.
Patients who may need surgery in the near future.
Study Design:
Allocation: Randomized
Endpoint Classification: Safety/Efficacy Study
Intervention Model: Parallel Assignment
Masking: Double Blind (Subject, Investigator)
Primary Purpose: Treatment
Primary Outcome Measures:
Reduction of 70 points in CDAI [Time Frame: 8 weeks] [Designated as safety issue: No].
Secondary Outcome Measures:
Change change in quality of life during the study [Time Frame: 8 weeks][Designated as safety issue: No]
Any adverse events during study period [Time Frame: 8 weeks][Designated as safety issue: Yes]

| Arms | Assigned Interventions |
| --- | --- |
| Experimental: Compound 1 HCl | Drug: Compound 1 HCl<br>Compound 1 HCl, twice a day, orally |
| Placebo Comparator: Placebo | Drug: Placebo<br>Placebo, twice a day, orally |

Example 12: Randomized, Double-Blind, Placebo-Controlled, Parallel Group, Dose-Response Study to Evaluate the Efficacy and Safety of Compound 1 HCl in the Prophylaxis of Migraine The purpose of this study is to evaluate the safety and efficacy of three doses of Compound 1 HCl (10 mg, 20 mg, and 40 mg taken daily) compared with placebo in the prevention of migraine.

Patients: Eligible subjects will be men and women 18 years to 65 years of age.
Criteria:
Inclusion Criteria:
Medical history consistent with migraine with or without aura according to the International Headache Society (IHS) for at least 6 months prior to the study
Between 3 to 12 migraine periods and no greater than 15 headache days (migraine and non-migraine) per month during the Baseline Phase
No clinically significant abnormalities on neurological exams, electrocardiogram (ECG) or clinical laboratory test results at baseline
Female patients must be postmenopausal for at least 1 year, surgically incapable of childbearing, practicing abstinence, or practicing an acceptable method of contraception (requires negative pregnancy test)
Exclusion Criteria:
Patients with headaches other than migraine
Patients with episodic tension or sinus headaches
Onset of migraine after age of 50 years
Patients who have failed more than two adequate regimens for migraine prophylaxis
Patients who overuse pain medications or certain other medications
Study Design:
Allocation: Randomized
Endpoint Classification: Safety/Efficacy Study
Intervention Model: Parallel Assignment
Masking: Double Blind (Subject, Investigator)
Primary Purpose: Treatment
Primary Outcome Measures:
Changes in length of time between the onset and cessation of painful migraine symptoms (migraine period) from the baseline. Safety evaluations conducted throughout the study.
Secondary Outcome Measures:
Proportion of patients responding to the treatment. Changes from baseline to double-blind phase in number of monthly migraine attacks, monthly migraine days, number of days/month requiring rescue medication, and Health-Related Quality of Life measures.

This is a randomized, double-blind, placebo-controlled, parallel-group, multi-center study to evaluate the effectiveness and safety of three different doses of Compound 1 HCl (10 mg, 20 mg, and 40 mg daily) in migraine prophylaxis. The study consists of five phases: baseline (determination of whether patients meet the eligibility criteria and tapering of any migraine medication patients are already taking); initial titration and double-blind phase (8 weeks) which begins with 5 mg/daily increasing to the assigned (10, 20, and 40 mg/day Compound 1 HCl); followed by a maintenance period at the target dose (18 weeks); tapering transition phase (up to 7 weeks); doses are adjusted to maximize effectiveness and minimize side effects. The primary study hypothesis is that one or more of the three doses of Compound 1 HCl (10, 20, and 40 mg/day) will be superior to placebo in the prophylaxis of migraine based on the change in monthly (28 day) migraine period rate from the prospective baseline period to the double-blind phase and that Compound 1 HCl treatment is well tolerated. During the titration period (8 weeks), doses are increased to target dose of daily Compound 1 HCl (10, 20, and 40 mg) or placebo, taken twice daily by mouth. Doses are continued for 18 weeks, adjusted over 7 weeks, and continued for up to 6 months during the Open-Label Extension.

Example 13: Study of Compound 1 HCl in the Treatment of Patients with Acute Pain from Bunionectomy The purpose of this study is to evaluate the effect of Compound 1 HCl on pain in bunionectomy.

Patients: Eligible subjects will be men and women over 20-80 years of age.

Criteria:

Inclusion Criteria:

Patients who are undergoing primary unilateral first metatarsal bunionectomy that includes a distal Chevron osteotomy only with or without the Akin procedure Healthy or medically stable on the basis of clinical laboratory tests performed at screening. If results are outside the normal reference ranges, the patient may be included only if the investigator judges the abnormalities or deviations from normal to be not clinically significant or to be appropriate and reasonable for the population under study Women must be postmenopausal, surgically sterile, abstinent, or practicing or agree to practice an effective method of birth control if they are sexually active before entry and throughout the study. Women of childbearing potential must have a negative serum 3 human chorionic gonadotropin pregnancy test at screening and a negative urine pregnancy test before surgery If a male and sexually active, agrees to use an approved method of birth control to prevent pregnancy in his female partner and not to donate sperm from the day of first study drug intake until 3 months after the day of last study drug intake. To qualify for entry into the double-blind treatment period, the following criteria must be met:

Qualifying baseline pain intensity (PI) must be rated as greater than or equal to 4 on an 11-point (0 to 10) PI numerical rating scale (NRS), recorded within 30 minutes before randomization Qualifying PI must occur no earlier than 10 hours after the first surgical incision Qualifying baseline PI must occur within 9 hours after termination of the systemic analgesia during the postoperative surgical period Exclusion Criteria:

History of seizure disorder or epilepsy suggested by the presence of mild or moderate traumatic brain injury, stroke, transient ischemic attack, or brain neoplasm within 1 year of screening, and/or severe traumatic brain injury, episode(s) of unconsciousness of more than 24 hours duration, or posttraumatic amnesia of more than 24 hours duration within 15 years of screening History of malignancy within the past 2 years before the start of the study Evidence of active infections that may spread to other areas of the body or a history of human immunodeficiency virus 1 or 2

Clinical laboratory values reflecting severe renal insufficiency

Moderately or severely impaired hepatic function, or patients with abnormal alanine aminotransaminase or aspartate aminotransferase Clinical laboratory values outside acceptable limits for surgery in the opinion of the investigator A clinically significant disease that in the investigator's opinion may affect efficacy or safety assessments Treated with anticonvulsants, monoamine oxidase inhibitors, tricyclic antidepressants, neuroleptics, or serotonin norepinephrine reuptake inhibitor within 2 weeks before randomization Systemic steroid therapy, excluding inhalers or topical steroids, within the 4 weeks before screening Women who plan to become pregnant during the study, or who are breast feeding Study Design:

Allocation: Randomized

Endpoint Classification: Efficacy Study

Intervention Model: Parallel Assignment

Masking: Double Blind (Subject, Investigator)

Primary Purpose: Treatment

Primary Outcome Measures:

Sum of Pain Intensity Differences (SPID) Over 48 Hours [Time Frame: 48 hours] Intensity (PI) is assessed on an 11-point numerical rating scale from 0=no pain to 10=pain as bad as you can imagine. PID is the difference between baseline PI (prior to the first dose) and current PI at assessment. SPID is calculated as the time-weighted Sum of PID scores over 48 hours. Total score ranges from −480 (worst) to 480 (best) for SPID48. A higher value of SPID indicates greater pain relief.

Secondary Outcome Measures:

Time to First Rescue Medication Use [Time Frame: Up to 48 hours]

[Designated as safety issue: No]

Reduction in Pain Intensity From Baseline at 12, 24, 48, and 72 Hours [Time Frame: Baseline (Day 1) and 12, 24, 48, and 72 hours] [Designated as safety issue: No]

This is a randomized, double-blind (neither physician nor patient knows the name of the assigned drug), placebo-controlled, parallel-group, multicenter study to evaluate the efficacy and safety of Compound 1 HCl 25 mg and 50 mg in patients who are undergoing bunionectomy (a surgical procedure to remove a bunion). The study will be divided into screening period, surgical period, qualification period, and a double-blind treatment period. The study length, including the screening period, will be up to a maximum duration of 32 days. Eligible patients will be randomly assigned to 1 of 3 treatment groups (Compound 1 HCl 25 mg, Compound 1 HCl 50 mg or placebo) in a 1:1:1 ratio. Efficacy and safety assessments will be performed during the study.

Example 14: Opioids with or without Compound 1 HCl in Treating Patients with Moderate to Severe Cancer Pain The purpose of this study is to see how well opioids work when given together with or without Compound 1 HCl in treating patients with moderate to severe cancer pain.

Patients: Eligible subjects will be men and women 18-70 years of age.

Criteria:
Moderate to severe cancer pain
Pain score ≥7/10 (0-10 numeric pain rating scale)
Requires strong opioids (step 3) for pain control or are already on stable doses of step 3 opioids
Opioid induced cognitive dysfunction or cognitive impairment
Life expectancy ≥3 months
Normal renal function
Not pregnant or nursing
Negative pregnancy test
Must have a telephone
Able to complete patient questionnaires alone or with assistance
No delirium
No hepatic dysfunction
No nursing home patients
No intractable nausea or vomiting
No true allergy or intolerance to opioids
No gastrointestinal pathology that influences absorption of opioids
No drug seeking behavior or recent substance abuse history
No major depression
No respiratory compromise
No evidence of severe or uncontrolled systemic disease (e.g., unstable or uncompensated respiratory, cardiac, hepatic, or renal disease)
No evidence of any other significant clinical disorder or laboratory finding that makes it undesirable for the patient to participate in the study
More than 1 month since prior radiotherapy, chemotherapy, or radionuclides
More than 1 month since prior bisphosphonates
No prior surgery that influences absorption of opioids
No concurrent therapeutic procedures or treatments that influence pain
No concurrent active radiation or antineoplastic therapies
No concurrent retroviral therapies
No concurrent drugs that interfere with CYP34A, CYP1A2, or CYP2D6
No concurrent drugs that interfere with morphine metabolism
No concurrent medications that will influence the disposition of morphine or methadone
No other concurrent antiemetics, antianxiety, or neuroleptic agents Study Design:
Allocation: Randomized
Masking: Double Blind (Subject, Investigator)
Primary Purpose: Supportive Care
Primary Outcome Measures:
Two-point pain improvement from baseline (0-10 numeric pain rating scale) [Designated as safety issue: No].
Secondary Outcome Measures:
Comparison of active treatment vs placebo [Designated as safety issue: No]
Effect of Compound 1 HCl on opioid adverse effects [Designated as safety issue: No]
Relationships between endpoints [Designated as safety issue: No]

| Arms | Assigned Interventions |
|---|---|
| Active Comparator: Arm I Patients receive oral opioid and oral placebo once daily for 4 weeks. | Other: placebo Given orally |
| Experimental: Arm II Patients receive oral opioid and 50 mg oral Compound 1 HCl once daily for 4 weeks. | Drug: Compound 1 HCl Given orally |
| Experimental: Arm III Patients receive oral opioid and 100 mg oral Compound 1 HCl once daily for 4 weeks. | Drug: Compound 1 HCl Given orally |

Example 15: Study of Compound 1 HCl to Treat Osteoarthritis Pain

The purpose of this study is to evaluate the effect of Compound 1 HCl on osteoarthritis pain of the hip or knee.

Patients: Eligible subjects will be men and women over 40 years of age.

Criteria:
Inclusion Criteria:
Primary diagnosis of Functional Class I-III OA of the hip or knee with documented osteoarthritis flare at baseline
Chronic user of nonsteroidal anti-inflammatory drugs (NSAIDs) and/or acetaminophen for OA pain
Discontinued all analgesic therapy at screening
For women of child-bearing potential: a woman who is not pregnant and not nursing, and who is practicing an acceptable method of birth control
Exclusion Criteria:
Requires continuous use of opioid or opioid combination products to control OA pain of the knee or hip
Clinically significant unstable cardiac, respiratory, neurological, immunological, hematological, or renal disease
Significant difficulties swallowing capsules or unable to tolerate oral medication
Previous participation in another clinical study of Compound 1 HCl or received any investigational drug or device or investigational therapy within 30 days before screening
Study Design:
Allocation: Randomized
Endpoint Classification: Safety/Efficacy Study
Intervention Model: Parallel Assignment
Masking: Double Blind (Subject, Investigator)
Primary Purpose: Treatment
Primary Outcome Measures:
Change From Baseline to Week 12 After Trial Entry in Osteoarthritis Pain Measured on the Western Ontario and McMaster Universities Osteoarthritis Index (WOMAC) Pain Subscale Score. [Time Frame: Baseline to Week 12/Early Termination]

[Designated as safety issue: No]. The pain in subjects with osteoarthritis is measured using the Western Ontario and McMaster Universities Osteoarthritis Index (WOMAC) pain subscale score. The WOMAC pain subscale score is calculated as the average of the visual analogue scale (VAS) scores from 5 pain subscale questions. Subjects mark the VAS, which is a horizontal line 100 mm in length, with a single vertical line to indicate their pain level over the last 24 hours, with 0 mm representing "No Pain" and 100 mm representing "Extreme Pain". The WOMAC pain subscale score difference is calculated as the WOMAC pain subscale score assessed at Week 12 minus the WOMAC pain subscale score assessed at baseline.

Secondary Outcome Measures:
Change From Baseline to Week 2 After Trial Entry in Osteoarthritis Pain Measured on the Western Ontario and McMaster Universities Osteoarthritis Index (WOMAC) Pain Subscale Score Change From Baseline to Week 6 After Trial Entry in Osteoarthritis Pain Measured on the Western Ontario and McMaster Universities Osteoarthritis Index (WOMAC) Pain Subscale Score Change From Baseline to the Average of Weeks 2, 6, and 12 After Trial Entry in Osteoarthritis Pain Measured on the Western Ontario and McMaster Universities Osteoarthritis Index (WOMAC) Pain Subscale Score

| Arms | Assigned Interventions |
| --- | --- |
| Experimental: Compound 1 HCl 25 mg bid | Drug: Compound 1 HCl 25 mg bid |
| Experimental: Compound 1 HCl 25 mg tid | Drug: Compound 1 HCl 25 mg tid |
| Placebo Comparator: Placebo | Drug: Placebo |

Example 16: Phase 3 Study Comparing 2 Doses of Compound 1 HCl Vs. Placebo for Treatment of Rheumatoid Arthritis The purpose of this study is to evaluate the effect of Compound 1 HCl on improving signs and symptoms and physical function in rheumatoid arthritis patients.

Patients: Eligible subjects will be men and women over 40 years of age.

Criteria:
Inclusion Criteria:
The patient has a diagnosis of RA based upon the American College of Rheumatology (ACR) 1987 Revised Criteria.

The patient has active disease at both Screening and Baseline, as defined by both: ≥6 joints tender or painful on motion; and ≥6 joints swollen; and fulfills 1 of the following 2 criteria at Screening: 1. ESR (Westergren method)>28 mm in the local laboratory. 2. CRP >7 mg/L in the central laboratory Patient had an inadequate response to at least one DMARD (traditional or biologic) due to lack of efficacy or toxicity.

No evidence of active or latent or inadequately treated infection with *Mycobacterium tuberculosis*.

Patient has washed out of all DMARDs other that antimalarials

Exclusion Criteria:
Blood dyscrasias including confirmed: 1. Hemoglobin <9 g/dL or Hematocrit <30%; 2. White blood cell count <3.0×109/L; 3. Absolute neutrophil count <1.2×109/L; 4. Platelet count <100×109/L History of any other autoimmune rheumatic disease other than Sjogren's syndrome No malignancy or history of malignancy.

History of infection requiring hospitalization, parenteral antimicrobial therapy, or as otherwise judged clinically significant by the investigator, within the 6 months prior to the first dose of study drug.

Study Design:
Allocation: Randomized
Endpoint Classification: Safety/Efficacy Study
Intervention Model: Parallel Assignment
Masking: Double Blind (Subject, Investigator)
Primary Purpose: Treatment Primary Outcome Measures:
Percentage of Participants Achieving American College of Rheumatology 20% (ACR20) Response at Month 3 [Time Frame: Month 3] [Designated as safety issue: No]. ACR20 response: greater than or equal to (>=) 20 percent (%) improvement in tender joint count; >=20% improvement in swollen joint count; and >=20% improvement in at least 3 of 5 remaining ACR core measures: participant assessment of pain; participant global assessment of disease activity; physician global assessment of disease activity; self-assessed disability (disability index of the Health Assessment Questionnaire [HAQ]); and C-Reactive Protein (CRP).

Change From Baseline in Health Assessment Questionnaire-Disability Index (HAQ-DI) Score at Month 3 [Time Frame: Baseline, Month 3] [Designated as safety issue: No]. HAQ-DI: participant-reported assessment of ability to perform tasks in 8 functional categories of daily living activities: dress/groom; arise; eat; walk; reach; grip; hygiene; and common activities over past week. Each item scored on 4-point scale from 0 to 3: 0=no difficulty; 1=some difficulty; 2=much difficulty; 3=unable to do. Overall score was computed as the sum of domain scores and divided by the number of domains answered. Total possible score range 0-3, 0=least functional difficulty and 3=extreme functional difficulty.

Percentage of Participant With Disease Activity Score Using 28-Joint Count and Erythrocyte Sedimentation Rate (4 Variables) (DAS28-4 [ESR]) Less Than 2.6 at Month 3 [Time Frame: Month 3] [Designated as safety issue: No]. DAS28-4 (ESR) calculated from swollen joint count (SJC) and tender/painful joint count (TJC) using 28 joint count, erythrocyte sedimentation rate (ESR) (millimeters per hour [mm/hour]) and patient's global assessment (PtGA) of disease activity (transformed score ranging 0 to 10; higher score indicated greater affectation due to disease activity). Total score range: 0 to 9.4, higher score indicated more disease activity. DAS28-4 (ESR) less than or equal to (=<) 3.2 implied low disease activity, greater than (>) 3.2 to 5.1 implied moderate to high disease activity and less than (<) 2.6=remission.

Secondary Outcome Measures:
Percentage of Participants Achieving American College of Rheumatology 20% (ACR20) Response at Week 2, Month 1 and 2 [Time Frame: Week 2, Month 1 and 2][Designated as safety issue: No].

Percentage of Participants Achieving American College of Rheumatology 20% (ACR20) Response at Month 4, 5, and 6 [Time Frame: Month 4, 5, and 6][Designated as safety issue: No].

Percentage of Participants Achieving American College of Rheumatology 50% (ACR20) Response at Week 2, Month 1 and 2 [Time Frame: Week 2, Month 1 and 2][Designated as safety issue: No].

Percentage of Participants Achieving American College of Rheumatology 50% (ACR20) Response at Month 4, 5, and 6 [Time Frame: Month 4, 5, and 6][Designated as safety issue: No].

| Arms | Assigned Interventions |
|---|---|
| Experimental: Compound 1 HCl 10 mg | Drug: Compound 1 HCl 10 mg Compound 1 HCl BID PO for 6 months |
| Experimental: Compound 1 HCl 25 mg | Drug: Compound 1 HCl 25 mg Compound 1 HCl BID PO for 6 months |
| Placebo Comparator: Placebo Sequence 1 | Drug: Placebo Placebo patients advance to 10 mg Compound 1 HCl BID at Month 3 visit |
| Placebo Comparator: Placebo Sequence 2 | Drug: Placebo Placebo patients advance to 25 mg Compound 1 HCl BID at Month 3 visit |

Example 17: Effect of Compound 1 HCl in the Treatment of Patients with Chemotherapy Induced Peripheral Neuropathy The purpose of this study is to evaluate the effect of to test the effect of Compound 1 HCl on peripheral neuropathy scores after 6 weeks treatment and is based on the separate assessment of pain and dysesthesia scores.

Patients: Eligible subjects will be men and women over 18-80 years of age.

Criteria:

Inclusion Criteria:

Have signed an Informed Consent to participate to the trial before any study related procedure has taken place.

Be >18 years and if a female with adequate contraception if of child bearing potential.

Have paclitaxel (or other taxane) induced peripheral neuropathy assessed by the presence of a NCI-CTC version 2 neuropathy sensory grade >/=2.

Peripheral neuropathy as clinically diagnosed during the neurological examination including sensitivity, motor function and deep tendon reflex assessments With Neuropathic pain as assessed by the presence of measurable pain perception (previous 24 h) on the Likert numerical rating scale >/=4 points at the screening visit and confirmed on DN4 with a score >/=4 and/or dysesthesia as assessed by the presence of measurable dysesthesia (previous 24 h) on the Likert numerical rating scale >/=4 points at the screening visit Persistent neuropathy for at least 3, but no more than 12 months after the end of chemotherapy.

Be either pain treatment naive or have important side effects or inadequate relief from their current pain medication (stable over last month).

Exclusion Criteria:

Have a documented neuropathy or risk factors of neuropathy which might interfere with the assessment of the severity of pain (eg, including, but not limited to, type 2 diabetes, peripheral vascular disease, B12 Vitamin deficiency, thyroid dysfunction, post surgical neuropathic pain, post-traumatic neuropathy, or neuropathy in relation with disease progression).

Have other neurological diseases that may produce weakness, sensory loss, or autonomic symptoms, or laboratory test abnormality.

Refractory to treatment defined as not improved, according to the Investigator, by 3 or more treatments prescribed for the current PN symptoms.

HIV positive serology.

History of, or current cardiac dysrhythmias and/or a history of cardiovascular disease, including myocardial infarction, except patients with only well controlled hypertension.

Have had prior (within the past 6 months) or have concurrent neurotoxic drugs (e.g., but not limited to, cisplatin, vincristine, vinblastine, cytarabine, thalidomide, bortezomib, or procarbazine, capecitabine, navelbine).

Have a current medication of lipid lowering agents other than statins.

Have a recent history (within the previous 6 months) or current evidence of alcohol or drug abuse.

Have concurrent unstable disease involving any system (eg, advanced carcinoma other than carcinoma justifying the recent treatment with taxanes, myocardial infarction, clinical or ECG signs of myocardial ischemia, cardiac insufficiency, anginal symptoms, current symptoms of CAD, renal impairment, or any other condition that in the opinion of the Investigator would make the patient unsuitable for study participation)

Be pregnant female or lactating.

Have renal impairment defined as blood creatinine >1.5× upper limit of normal (ULN)

Hemostasis disorders or current treatment with oral anticoagulants.

Have hepatic impairment hepatic function as follows: liver enzymes (ALT and AST)>2×ULN or >3.5×ULN in case of liver metastasis Participated in any other investigational drug or therapy study with a non approved medication, within the previous 3 months.

Any other condition which, in the opinion of the investigator would impede competence or compliance or possibly hinder completion of the study Study Design:

Allocation: Randomized

Endpoint Classification: Safety/Efficacy Study

Intervention Model: Parallel Assignment

Masking: Double Blind (Subject, Investigator)

Primary Purpose: Treatment

Primary Outcome Measures:

Percentage of responders defined as patients with a minimum decrease of 50% of their maximum neuropathic pain dimension (either pain or dysesthesia) present at baseline. [Time Frame: The mean pain score during the last 7 days of the treatment period will be compared to the mean score of the last 7 days of the screening score period.][Designated as safety issue: No].

Secondary Outcome Measures:

Assessment with respect to placebo of the effect of Compound 1 HCl on Neuropathic Pain Inventory Score (total and by dimension) [Time Frame: Screening visit; V0; V1; V2; V3; V4; V5] [Designated as safety issue: No]

Assessment with respect to placebo of the effect of Compound 1 HCl on Short-Form BPI [Time Frame: Screening visit; V0; V1; V2; V3; V4; V5] [Designated as safety issue: No]

Assessment with respect to placebo of the effect of Compound 1 HCl on Quality of life questionnaire (CIPN 20) [Time Frame: V0; V3; V5] [Designated as safety issue: No]

Assessment with respect to placebo of the effect of Compound 1 HCl on Dysgueusia questionnaire [Time Frame: V0; V3; V5] [Designated as safety issue: No]

Assessment with respect to placebo of the effect of Compound 1 HCl on Quantitative Sensory Testing [Time Frame: V0; V3; V5] [Designated as safety issue: No]

Assessment with respect to placebo of the effect of Compound 1 HCl on ENMG [Time Frame: V0; V3; V5] [Designated as safety issue: No]

Assessment with respect to placebo of the effect of Compound 1 HCl on the use of rescue medication [Time Frame: Screening visit; V0; V1; V2; V3; V4; V5] [Designated as safety issue: No]

Assessment with respect to placebo of the effect of Compound 1 HCl on safety profile [Time Frame: Screening visit; V0; V1; V2; V3; V4; V5] [Designated as safety issue: Yes]

Assessment with respect to placebo of the effect of Compound 1 HCl on Global Impression of change as assessed by Investigator [Time Frame: V1; V2; V3; V4; V5] [Designated as safety issue: No]

Assessment with respect to placebo of the effect of Compound 1 HCl on Global Impression of change as assessed by patient [Time Frame: V1; V2; V3; V4; V5] [Designated as safety issue: No]

Assessment with respect to placebo of the effect of Compound 1 HCl on Hospital Anxiety and Depression scale [Time Frame: V0;V3;V5] [Designated as safety issue: No]

| Arms | Assigned Interventions |
| --- | --- |
| Experimental: Compound 1 HCl (40 mg) once a day | Drug: Compound 1 HCl Compound 1 HCl (40 mg) once a day |
| Placebo Comparator: Control Placebo once a day | Drug: Placebo Control Placebo once a day |

What is claimed is:

1. A method of treating vasoocclussive painful crises in sickle cell disease in a patient in need thereof, comprising administering to the patient in need thereof an effective dose of 1,1,1,3,3,3-hexafluoropropan-2-yl 4-(2-(pyrrolidin-1-yl)-4-(trifluoromethyl)benzyl)piperazine-1-carboxylate (Compound 1), or a pharmaceutically acceptable salt thereof.

2. The method of claim 1, wherein the effective dose is from about 1 mg to about 100 mg.

3. The method of claim 1, wherein at least 30% of MGLL in PBMCs from the patient are covalently modified after administration of the effective dose.

4. The method of claim 1, wherein the steady state plasma $AUC_{0-24}$ of Compound 1 is at least 0.05 μM·hr after administration of the effective dose.

5. The method of claim 1, wherein the effective dose is from about 1 mg to about 50 mg.

6. The method of claim 1, wherein the effective dose is from about 2 mg to about 25 mg.

7. The method of claim 1, wherein the effective dose is from about 1 mg to about 15 mg.

8. The method of claim 1, wherein the effective dose is from about 10 mg to about 20 mg.

9. The method of claim 1, wherein Compound 1 is administered orally.

10. The method of claim 1, wherein the effective dose is administered to the patient once per day.

11. The method of claim 1, wherein the effective dose is administered to the patient twice per day.

* * * * *